(12) United States Patent
Kol et al.

(10) Patent No.: US 9,493,587 B2
(45) Date of Patent: Nov. 15, 2016

(54) METAL COMPLEXES OF SALAN-TYPE LIGANDS AND USES THEREOF AS CATALYSTS FOR POLYMERIZATION OF ALPHA-OLEFINS

(75) Inventors: Moshe Kol, Ramat Gan (IL); Konstantin Press, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 431 days.

(21) Appl. No.: 13/980,920

(22) PCT Filed: Jan. 19, 2012

(86) PCT No.: PCT/IB2012/050267
§ 371 (c)(1),
(2), (4) Date: Jul. 22, 2013

(87) PCT Pub. No.: WO2012/098521
PCT Pub. Date: Jul. 26, 2012

(65) Prior Publication Data
US 2013/0310529 A1    Nov. 21, 2013

Related U.S. Application Data

(60) Provisional application No. 61/434,449, filed on Jan. 20, 2011.

(51) Int. Cl.
| | | |
|---|---|---|
| C08F 4/76 | (2006.01) | |
| B01J 27/24 | (2006.01) | |
| C07C 215/50 | (2006.01) | |

(Continued)

(52) U.S. Cl.
CPC .................. *C08F 4/76* (2013.01); *B01J 27/24* (2013.01); *C07C 215/50* (2013.01); *C07F 7/00* (2013.01); *C07F 7/006* (2013.01); *C08F 10/00* (2013.01); *C07C 2103/74* (2013.01); *C08F 110/06* (2013.01)

(58) Field of Classification Search
None
See application file for complete search history.

(56) References Cited

U.S. PATENT DOCUMENTS

| | | |
|---|---|---|
| 6,632,899 B2 | 10/2003 | Kol et al. |
| 6,686,490 B1 | 2/2004 | Kol et al. |

(Continued)

FOREIGN PATENT DOCUMENTS

| | | |
|---|---|---|
| WO | WO 02/36638 | 5/2002 |
| WO | WO 03/091292 | 11/2003 |

(Continued)

OTHER PUBLICATIONS

Communication Relating to the Results of the Partial International Search Dated Apr. 19, 2012 From the International Searching Authority Re. Application No. PCT/IB2012/050267.

(Continued)

*Primary Examiner* — Ling Choi
*Assistant Examiner* — Catherine S Branch

(57) ABSTRACT

Use of homogeneous catalytic systems which include as a pre-catalyst a complex of a group 4 metal and a Salan ligand in the polymerization of alpha-olefins, is disclosed. The Salan ligand is characterized by a sequential diamino-containing skeleton unit which is non-symmetric, and the pre-catalysts can also be such that are devoid of a symmetry element. The disclosed polymerization results in alpha-olefin polymers such as polypropylene which are characterized by high levels of tacticity. Also disclosed are novel Salan ligands and novel complexes thereof with group 4 metals.

13 Claims, 12 Drawing Sheets

(51) Int. Cl.
 C07F 7/00 (2006.01)
 C08F 10/00 (2006.01)
 C08F 110/06 (2006.01)

(56) References Cited

U.S. PATENT DOCUMENTS 7,241,714 B2 7/2007 Boussie et al.
2005/0227860 A1 10/2005 Green et al.

FOREIGN PATENT DOCUMENTS

WO WO 2009/027516 3/2009
WO WO 2011/158241 12/2011
WO WO 2012/098521 7/2012

OTHER PUBLICATIONS

Corrected International Search Report and the Written Opinion Dated Sep. 25, 2012 From the International Searching Authority Re. Application No. PCT/IB2012/050267.
International Search Report and the Written Opinion Dated Jun. 19, 2012 From the International Searching Authority Re. Application No. PCT/IB2012/050267.
Busico et al. "Block Copolymers of Highly Isotactic Polypropylene Via Controlled Ziegler-Natta Polymerization", Macromolecules, 37(22): 8201-8203, 2004.
Busico et al. "Design of Stereoselective Ziegler-Natta Propene Polymerization Catalysts", Proc. Natl. Acad. Sci. USA, PNAS, 103(42): 15321-15326, Oct. 17, 2006.
Busico et al. "Living Ziegler-Natta Polymerization: True or False?", Macromolecules Symposium, 226: 1-16, 2005.
Busico et al. "Mimicking Ziegler-Natta Catalysts in Homogeneous Phase, 1. C2-Symmetric Octahedral Zr(IV) Complexes With Tetradentate [ONNO]-Type Ligands", Macormolecules Rapid Communications, 22(17): 1405-1410, 2001.
Busico et al. "Reactivity of Secondary Metal-Alkyls in Catalytic Propene Polymerization: How Dormant Are 'Dormant Chains'?", Journal of the Ameican Chemical Society, 127(6): 1608-1609, 2005.
Busico et al. "The First Molecularly Characterized Isotactic Polypropylene-BlockPolyethylene Obtained Via 'Quasi-Living' Insertion Polymerization", Macromolecules, 31(11): 3806-3808, 2003.
Ciancaleone et al. "Activation of A Bis(Phenoxy-Amine) Precatalyst for Olefin Polymerization: First Evidence for an Outer Sphere Ion Pair With the Methylborate Counterion", Dalton Transactions, p. 8824-8827, 2009.
Ciancaleone et al. "Stucture-Activity Relationship in Olefin Polymerization Catalysis: Is Entropy the Key?", Journal of the American Chemical Society, JACS, 132: 13651-13653, 2010.
Cipullo et al. "Improving the Bahvior of Bis(Phenoxyamine) Group 4 Metal Catalysts for Controlled Alkene Polymerization", Macromolecules, 42: 3869-3872, 2009.
Cohen et al. "C1-Symmetric Zirconium Complexes of [ONNO']-Type Salan Ligands: Accurate Control of Catalyst Activity, Isospecificity, and Molecular Weight in 1-Hexene Polymerization", Organometallics, XP055024087, 28(5): 1391-1405, Feb. 9, 2009.
Cohen et al. "Construction of C1-Symmetric Zirconium Complexes by the Design of New Salan Ligands. Coordination Chemistry and Preliminary Polymerisation Catalysis Studies", Chemical Communication, p. 2149-2151, 2008.
Cohen et al. "Same Ligand, Different Metals: Diiodo-Salan Complexes of the Group 4 Triad in Isospecific Polymerization of 1-Hexene and Propylene", Macromolecules, 43: 1689-1691, 2010.
Egami et al. "Fe(Salan)-Catalyzed Asymmetric Oxidation of Sulfides With Hydrogen Peroxide in Water", Journal of the American Chemical Society, 129(29): 8940-8941, 2007.
Egami et al. "Nb(Salan)-Catalyzed Asymmetric Epoxidationof Allylic Alcohols With Hydrogen Peroxide", Angewandte Chemie, International Edition, 47: 5171- 5174, 2008.
Egami et al. "Oxidation Catalysis of Nb(Salan) Complexes: Asymmetric Epoxidation of Allylic Alcohols Using Aqueous Hydrogen Peroxide as an Oxidant", Journal of the American Chemical Society, JACS, 132: 5886-5895, 2010.
Egami et al. Enantioenriched Synthesis of C1-Symmetric BINOLs: Iron-Catalyzed Cross-Coupling of 2-Naphthols and Some Mechanistic Insight, Journal of the American Chemical Society, JACS, 132: 13633-13635, 2010.
Gendler et al. "Titanium and Zirconium Complexes of Robust Salophan Ligands. Coordination Chemistry and Olefin Polymerization Catalysis", Journal of the American Chemical Society, JACS, 130: 2144-2145, 2008.
Groysman et al. "Salophan Complexes of Group IV Metals", European Journal of Inorganic Chemistry, p. 2480-2485, 2005.
Kondo et al. "A µ-Oxo-µ-η2:η2-Peroxo Titanium Complex as A Reservoir of Active Species in Asymmetric Epoxidation Using Hydrogen Peroxide", Angewandte Chemie, International Edition, 47: 10195-10198, 2008.
Lamberti et al. "Mechanism of Stereospecific Polymerization of α-Olefins by Late-Transition Metal and Octahedral Group 4 Metal Catalysts", Coordination Chemistry Reviews, 253: 2082-2097, 2009.
Manna et al. "Markedly Different Cytotoxicity of the Two Enantiomers of C2-Symmetrical Ti(IV) Phenolato Complexes; Mechanistic Implications", Dalton Transactions, 39: 1182-1184, 2010.
Matsumoto et al. "Asymmetric Catalysis of Metal Complexes With Non-Planar ONNO Ligands: Salen, Salalen and Salan", Chemical Communications, p. 3619-3627, 2007.
Matsumoto et al. "Asymmetric Epoxidation of Olefins Catalyzed by Ti(Salan) Complexes Using Aqueous Hydrogen Peroxide as the Oxidant", Pure Applied Chemistry, 80(5): 1071-1077, 2008.
Matsumoto et al. "Highly Enantioselective Epoxidation of Styrenes Catalyzed by Proline-Derived C1-Symmetric Titanium(Salan) Complexes", Angewandte Chemie, International Edition, XP055024094, 48(40): 7432-7435, Sep. 21, 2009. Fig.2, Scheme 2, Ligands 4, 5.
Meker et al. "Major Impact of N-Methylation on Cytotoxicity and Hydrolysis of Salan Ti(IV) Complexes: Sterics and Electronics Are Intertwined", Dalton Transactions, 40: 9802-9809, 2011.
Sawada et al. "Titanium-Salan-Catalyzed Asymmetric Epoxidation With Aqueous Hydrogen Peroxide as the Oxidant", Angewandte Chemie, International Edition, 45: 3478-3480, 2006.
Segal et al. "Isospecific Polymerization of Vinylcyclohexane by Zirconium Complexes of Salan Ligands", Macromolecules, 41: 1612-1617, 2008.
Segal et al. "Zirconium and Titanium Diamine Bis(Phemolate) Catalysts for α- Olefin Polymerization: From Atactic Oligo(1-Hexene) to Ultrahigh-Molecular-Weight Isotactic Poly(1-Hexene)", Organometallics, 24: 200-202, 2005.
Sergeeva et al. "Satan Ligands Assembled Around Chiral Bipyrrolidine: Predetermination of Chirality Around Octahedral Ti and Zr Centres", Chemical Communications, p. 3053-3055, 2009.
Strianese et al. "A Comparative Study on the Polymerization of α-Olefins Catalyzed by Salen and Salan Zirconium Complexes", Macromolecular Chemistry and Physics, 209: 585-592, 2008.
Talarico et al. "Origin of the Regiochemistry of Propene Insertion at Octahedral Colums 4 Polymerization Catalysts: Design or Serendipity?", Journal of the American Chemical Society, JACS, 125(24): 7172-7173, 2003.
Tshuva et al. "Tsospecific Living Polymerization of 1-Hexene by a Readily Available Nonmetallocene C2-Symmetrical Zirconium Catalyst", Journal of the American Chemical Society, JACS, 122: 10706-10707, 2000.
Tshuva et al. "Single-Step Synthesis of Salans and Substituted Salans by Mannich Condensation", Tetrahedron Letters, 42: 6405-6407, 2001.

(56) References Cited

OTHER PUBLICATIONS

Yeori et al. "Cyclopolymerization of 1,5-Hexadiene by Enantiomerically-Pure 'Zirconium Salan Complexes. Polymer Optical Activity Reveals α-Olefin Face Preference", Macromolecules, 40: 8521-8523, 2007.

Yeori et al. "Diastereoisomerically Selective Enantiomerically Pure Titanium Complexes of Salan Ligands: Synthesis, Structure, and Preliminary Activity Studies", Inorganic Chemistry, 44(13): 4466-4468, 2005.

Yeori et al. "Diastereomerically-Specific Zirconium Complexes of Chiral Salan Ligands: Isospecific Polymerization of 1-Hexene and 4-Methyl-l-Pentene and Cyclopolymerization of 1,5-Hexadiene", Journal of the American Chemical Society, JACS, 128: 13062-13063, 2006.

METAL COMPLEXES OF SALAN-TYPE LIGANDS AND USES THEREOF AS CATALYSTS FOR POLYMERIZATION OF ALPHA-OLEFINS

RELATED APPLICATIONS

This application is a National Phase of PCT Patent Application No. PCT/IB2012/050267 having International filing date of Jan. 19, 2012, which claims the benefit of priority under 35 USC §119(e) of U.S. Provisional Patent Application No. 61/434,449 filed on Jan. 20, 2011. The contents of the above applications are all incorporated by reference as if fully set forth herein in their entirety.

FIELD AND BACKGROUND OF THE INVENTION

The present invention, in some embodiments thereof, relates to chemical syntheses and, more particularly, but not exclusively, to novel processes of olefin polymerization, to catalyst systems which comprise, as pre-catalysts, metal complexes of group 4 Salan ligands which can be utilized in these processes, and to Salan ligand precursors for preparing these complexes.

The huge plastics industry produces a broad variety of polymeric materials having a broad range of properties. These plastic materials are derived from a small group of building blocks—monomers—including ethylene and propylene. The properties of the polymeric materials depend on the nature of these building blocks and on the process employed to assemble these building block. Most of these processes rely on catalytic polymerization.

The nature of the catalyst has a crucial role in determining the microstructure of the polymer thus determining the physical properties of the resulting plastic. The microstructural characteristics of polymers and copolymers of propylene include: molecular weight, molecular weight distribution (Mw/Mn; or PDI), and above all, the type and degree of stereoregularity (tacticity) and regioregularity (head-to-tail enchainment). These microstructural characteristics influence the properties of the resulting polymer. For example, three familiar forms of polypropylene are: isotactic in which all methyl side groups are pointing in the same direction in the stretched chain; syndiotactic in which the methyl side groups point at opposite directions alternatingly; and atactic in which the methyl groups are pointing randomly in the two directions. A higher degree of stereoregularity (and regioregularity) tends to lead to higher crystallinity and melting points. In particular, polypropylene having a very high degree of isotacticity has a melting transition of $T_m=165°$ C. whereas an atactic polypropylene, if it has a melting point, is typically much lower.

The type and degree of tacticity are also influenced by the catalyst systems employed. Other properties influenced by the catalyst system include the polymer chain-lengths and chain-length distributions, possible backbone rearrangement, regio-regularity, ability to incorporate different monomers, etc. Successful catalysts also need to be sufficiently active under industrially-relevant conditions.

Many of the industrial catalytic processes employed in ethylene and propylene polymerizations and copolymerizations rely on heterogeneous catalysis processes, and most of which, on heterogeneous Ziegler-Natta type catalysts. Ziegler-Natta catalysts are group 4 metal complexes activated with alkyl-aluminum co-catalysts, which were invented in the 1950's. Recent generations of such catalysts include titanium chloride adsorbed on magnesium chloride and have various combinations of internal and external donors. More recent Ziegler-Natta catalysts are very active and can produce highly isotactic polypropylene (having a melting point of about 165° C.). Yet, these catalysts result in polymers having a broad molecular weight distribution ($PDI=M_w/M_n>3.5$), and their activity towards higher olefins is considerably lower.

The next generation catalysts, both homogeneous and heterogeneous, to be developed, are referred to as metallocenes. These catalysts are based upon transition metals (such as group 4 metals) having at least one group 4 cyclopentadienyl-type (Cp) rings as spectator ligands (groups that do not detach from the metal during the catalytic process). Systems that include two Cp rings are generally referred to as "bis-Cp" metallocenes, and systems that include a single Cp ring are referred to as "mono-Cp" metallocenes or "half" metallocenes. Cp-containing systems often require co-catalysts for their activation, such as alumoxanes (e.g., methyl aluminoxane) or various boron-based activators (often combined with aluminum based quenchers or scavengers). When alumoxane is employed as co-catalyst, a usually taken in large excess relative to the pre-catalyst—the common range being 1000-10000:1 MAO:pre-catalyst.

A specific class of half metallocenes termed "constrained geometry catalysts" was found to incorporate high-olefins readily and has found commercial applications in copolymerization of ethylene and high-olefins to produce linear low density polyethylene (LLDPE).

Metallocenes have been investigated very intensively during the past three decades and numerous scientific articles and patents describing various structural modifications and their applications in propylene and other olefin polymerizations have appeared. Correlations between the symmetries of the catalysts and the tacticities of the resulting polymers were established (Ewen's Rules). Of the metallocenes, some of the most studied were the zirconocenes. Yet the commercial applications of the metallocenes are limited: the price of the successful metallocenes is high relative to the Ziegler-Natta heterogeneous catalysts, and the isotacticity degree of the resulting polypropylene is often inferior.

In the past 15 years, there has been interest in development of "cyclopentadienyl-free systems", e.g., pre-catalysts devoid of a cyclopentadienyl ring. Such modified catalysts are hoped to lead to polymers of new or improved properties. These non-metallocene systems include all kinds of transition metals, and still, the most promising systems in terms of activities and stereospecificities are tend to be based on the group 4 metals. Some of these catalysts have shown remarkable activities including living polymerization of high olefins at room temperature, highly active polymerization of ethylene, and the combination of living and isospecific polymerization of high olefins. Yet, except for scarce cases, the tacticity induction in propylene polymerization by non-metallocenes is inferior in comparison to the best metallocenes and to the latest generation heterogeneous Ziegler-Natta catalysts.

Salans are sequential tetradentate dianionic {ONNO}-type ligands that include two neutral amine-type N-donors and two anionic phenolate-type O-donors. Group 4 complexes of Salan ligands that exhibited isospecific polymerization of 1-hexene were first introduced by one of the present inventors (see, Kol et al., *J. Am. Chem. Soc.* 2000, 122, 10706-10707; and U.S. Pat. Nos. 6,632,899 and 6,686, 490).

Group 4 complexes of Salan ligands as highly active catalysts in alpha-olefin polymerization were also disclosed in WO 03/091292. According to the teachings of WO 03/091292, propylene polymerization using the disclosed catalysts yielded a viscous liquid or a sticky solid of low molecular weight, rather than isotactic polypropylene of high molecular weight.

WO 2009/027516 discloses block-copolymers as compatibilizers that were prepared by previously published Salan complexes.

Since the year of 2,000, numerous scientific papers pertaining to group 4 catalysts based on Salan ligands and their applications in different types of polymerizations and copolymerizations of alpha-olefins and dienes, have been published.

However, none of the Salan catalysts described thus far was able to lead to practical catalysts for commercially relevant applications, such as highly active isospecific polymerization of propylene to yield high molecular weight polypropylene with a high melting point. Thus, none of the Salan catalysts was found to act in propylene polymerization as both a highly active catalyst that produces polymers with high tacticities.

For example, a zirconium catalyst of a symmetric Salan ligand that features a 1-adamantyl group in the ortho positions of both phenolate rings led to polypropylene with an isotacticity degree [mmmm] of 98.5% and melting point of 152° C. However, the activity of this catalyst was low: 4.8 grams polypropylene$\times$mmol$^{-1}\times$[$C_3H_6$]$^{-1}\times$h$^{-1}$ (Busico et al. *Proc. Nat. Acad. Sci.* 2006, 103, 15321).

A hafnium analogue of this catalyst led to higher tacticities, however, its activity was more than 10 times lower, so the molecular weight of the polymer obtained after 20 hours was only 7,200 gram/mol, corresponding to less than 200 repeat units, which is too low to give a meaningful melting transition (Cipullo et al. *Macromolecules* 2009, 42, 3869).

Zirconium catalysts of Salan ligands bearing halo-substituents (chloro or bromo) led to highly isotactic poly (vinylcyclohexane) (Segal et al. *Macromolecules* 2008, 41, 1612). However, the degree of isotacticity was reduced drastically when a "less bulky" monomer like 1-hexene was polymerized (Segal et al. *Organometallics* 2006, 24, 200).

A titanium catalyst of a symmetric Salan ligand that features the electron withdrawing iodo groups in the ortho, para positions of both phenolate rings showed a much higher activity of up to 390 grams polypropylene$\times$mmol$^{-1}\times$[$C_3H_6$]$^{-1}\times$h$^{-1}$, and a high molecular weight of $M_n$=240,000. However, its highest tacticity was [mmmm]=83% and correspondingly, the melting point was only 123° C. (Cohen et al. *Macromolecules* 2010, 43, 1689).

Attempts to produce $C_1$-symmetric catalysts by devising Salan ligands that include a phenolate ring with stereo-directing bulky groups and a phenolate ring including activity-enhancing electron-withdrawing groups led to average values of the activities of the catalysts and average values of the tacticities of the resulting polymers (Cohen et al. *Organometallics* 2009, 28, 1391).

In addition, metal complexes of chiral Salan ligands were employed as catalysts for other transformations such as asymmetric catalysis. These include Salan ligands in which both of the amine-type N-donors are secondary amines (namely, each has one hydrogen substituent).

Strianese et al., *Macromol. Chem. Phys.* 2008, 209, 585-592; and Lamberti et al., *Coord. Chem. Rev.* 2009, 253, 2082-2097 teach Salan ligands assembled around dinaphthyl-diamine skeleton and bearing hydrogen atoms on the N-donors, and further teach complexes of these ligands. The complexes possess a C2-symmetry and give low activity and practically atactic polypropylene.

Matsumoto et al., *Angew. Chem. Int. Ed.* 2009, 48, 7432-7435 teach a Salan ligand which is based on aminomethylpyrrolidine, for use in asymmetric catalysis. Other publications by the same research group [Sawada et al., *Angew. Chem. Int. Ed.* 2006, 45, 3478-3480; Matsumoto et al., *Chem. Commun.* 2007, 3619-3627; Egami et al., *J. Am. Chem. Soc.* 2007, 129, 8940-8941; Matsumoto et al., *Pure Appl. Chem.* 2008, 80, 1071-1077; Egami et al., *Angew. Chem. Int. Ed.* 2008, 47, 5171-5174; Kondo et al., *Angew. Chem. Int. Ed.* 2008, 47, 10195-10198; Egami et al., *J. Am. Chem. Soc.* 2010, 132, 5886-5895; and Egami et al., *J. Am. Chem. Soc.* 2010, 132, 13633-13635] teach Salan ligands built around chiral diamine skeletons, in which the substituents on both of the N-donors are hydrogen atoms. The ligands have a symmetry element and the preferred ligand wrapping mode around a group 4 element is fac-fac. All complexes were employed for asymmetric catalysis.

Manna et al., *Dalton Trans.* 2010, 39, 1182-1184 teach complexes of chiral Salan ligands featuring hydrogen substituents on the N-donors, and fac-fac wrapping mode around a group 4 element. These complexes were reported to exhibit cytotoxicity.

Additional references of interest include WO 2011/158241 and Meker et al., Dalton Trans 2011, 40, 9802.

SUMMARY OF THE INVENTION

There is a constant need to develop new catalytic systems for polymerizations and co-polymerizations of olefins such as ethylene, propylene, and higher olefins, since these catalysts can have substantial effect on the efficiency of the polymerization process and on the properties of the produced plastic materials.

The recurring unsuccessful attempts to produce a catalyst that will be sufficiently active on one hand, and will be capable of producing polypropylene with sufficiently high molecular weights and sufficiently high isotacticities on the other hand, such that a useful high-melting plastic will be produced, indicate that a new design motif in Salan catalysts is required.

The present inventors have devised and successfully prepared and practiced novel pre-catalysts for alpha-olefin polymerization that, following activation, give rise to highly-active catalysts that afford polymers with controllable, and preferably high, high isotacticities, and other desirable properties.

Without wishing to be bound by any particular theory, it is believed that the high activity and high isotacticity exhibited by the pre-catalysts disclosed herein is achieved by tuning the ligand structure such that the geometry of the pre-catalyst is non-conventional and lacks any element of symmetry, as described in more detail hereinafter. The pre-catalysts are characterized as a complex of a Salan ligand and a group 4 element, in which the Salan ligand is designed such that its sequential diamino-containing skeleton unit is non-symmetric (e.g., non-palindromic).

According to an aspect of some embodiments of the present invention there is provided a process of polymerizing an alpha-olefin, the process comprising contacting the alpha-olefin with a catalyst system which comprises:

(i) a pre-catalyst represented by general Formula II:

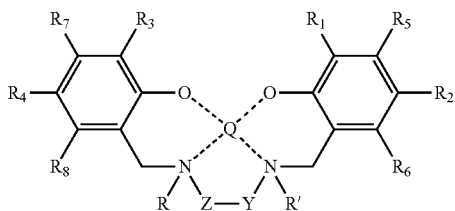

Formula II wherein:

Q is MXn, whereas M is a group 4 element; X is a labile group; and n is 0, 1, 2, 3 or 4;

Z and Y are each independently a substituted or unsubstituted alkylene chain being from 1 to 5 carbon atoms in length, such that Z and Y form together an alkylene chain that is 2 to 10 carbon atoms in length;

each of $R_1$-$R_8$ is independently selected from the group consisting of hydrogen, alkyl, cycloalkyl, aryl, halogen, alkoxy, aryloxy, heteroalicyclic, heteroaryl, and nitro, provided that at least one of $R_1$-$R_4$ is other than hydrogen; and each of R and R' is independently selected from the group consisting of hydrogen, alkyl, cycloalkyl and aryl, provided that (i) at least one of and R' is hydrogen; and/or (ii) if R and R' are the same, Y is different from Z; and (ii) a co-catalyst, thereby polymerizing the alpha-olefin.

According to some embodiments of the present invention, $R_1$-$R_4$ are each independently selected from the group consisting of halogen, alkyl and cycloalkyl.

According to some embodiments of the present invention, at least one of $R_1$-$R_4$ are each independently halogen.

According to some embodiments of the present invention, at least two of $R_1$-$R_4$ are each independently halogen.

According to some embodiments of the present invention, each of $R_1$-$R_4$ is independently halogen.

According to some embodiments of the present invention, at least one of $R_1$-$R_4$ is a bulky substituent.

According to some embodiments of the present invention, $R_1$ is the bulky substituent.

According to some embodiments of the present invention, each of $R_1$-$R_4$ is the bulky substituent.

According to some embodiments of the present invention, the bulky substituent comprises a bulky rigid group.

According to some embodiments of the present invention, the bulky rigid substituent is adamantyl.

According to some embodiments of the present invention, $R_1$ is adamanty; $R_2$ is alkyl, and at least one of $R_3$ and $R_4$ (or each) is halogen.

According to some embodiments of the present invention, Z and Y form together an alkylene chain being from 2 to 6 carbon atoms in length.

According to some embodiments of the present invention, Z is selected from the group consisting of (CRaRb), (CRaRb)(CRcRd) and (CRaRb)(CRcRd)(CReRf), and Y is selected from the group consisting of (CRgRh), (CRgRh)(CRiRj) and (CRgRh)(CRiRj)(CRkRp), wherein each of Ra-Rp is independently selected from the group consisting of hydrogen, alkyl, cycloalkyl, aryl, halogen, alkoxy, aryloxy, and/or at least two of Ra-Rp, R' and R form together a five- or six-membered, aromatic or non-aromatic ring.

According to some embodiments of the present invention, R' is hydrogen.

According to some embodiments of the present invention, R is alkyl.

According to some embodiments of the present invention, Y is (CRgRh).

According to some embodiments of the present invention, Z is (CRaRb).

According to some embodiments of the present invention, Ra, Rb, Rg and Rh are each hydrogen.

According to some embodiments of the present invention, Ra and R form together the ring.

According to some embodiments of the present invention, Rb, Rh and Rg are each hydrogen.

According to some embodiments of the present invention, Ra, Rb, Rg and Rh form together an aromatic ring.

According to some embodiments of the present invention, Y is (CRgRh)(CRiRj) and Z is (CRaRb).

According to some embodiments of the present invention, Ra, Rb and Rg-Rj are each hydrogen.

According to some embodiments of the present invention, R' is hydrogen.

According to some embodiments of the present invention, Rg-Rj form together an aromatic ring.

According to some embodiments of the present invention, R and R' are each independently selected from the group consisting of hydrogen and alkyl.

According to an aspect of some embodiments of the present invention there is provided a process of polymerizing an alpha-olefin, the process comprising contacting the alpha-olefin with a catalyst system which comprises:

(i) a pre-catalyst comprising a group 4 element being in coordination with a Salan ligand, the pre-catalyst being devoid of a symmetry element; and (ii) a co-catalyst, thereby polymerizing the alpha-olefin.

According to some embodiments of the present invention, the Salan ligand comprises two substituted or unsubstituted phenol moieties and a sequential diamino-containing skeleton unit linking the phenol moieties, wherein the sequential diamino-containing skeleton unit is non-symmetric.

According to an aspect of some embodiments of the present invention there is provided a process of polymerizing an alpha-olefin, the process comprising contacting the alpha-olefin with a catalyst system which comprises:

(i) a pre-catalyst comprising a group 4 element being in coordination with a Salan ligand, the Salan ligand comprising two substituted or unsubstituted phenol moieties and a sequential diamino-containing skeleton unit linking the phenol moieties, wherein the sequential diamino-containing skeleton unit is non-symmetric; and (ii) a co-catalyst, thereby polymerizing the alpha-olefin.

According to some embodiments of the present invention, the Salan ligand is capable of wrapping around the group 4 element in a fac-mer configuration.

According to some embodiments of the present invention, the co-catalyst is selected from the group consisting of an alumoxane, a non-coordinative anion, and any mixture thereof.

According to some embodiments of the present invention, the co-catalyst comprises methylaluminoxane.

According to some embodiments of the present invention, a ratio of the co-catalyst to the pre-catalyst ranges from 1:1 to 10000:1.

According to some embodiments of the present invention, the process is performed in solution phase.

According to some embodiments of the present invention, the process is performed in solventless phase.

According to some embodiments of the present invention, the process is performed at a temperature that ranges from 0° C. to 200° C.

According to some embodiments of the present invention, the alpha-olefin is selected from the group consisting of ethylene, propylene, 1-butene, 1-pentene, 4-methyl-1-pentene, 1-hexene, vinyl-cyclohexane, 1,5-hexadiene, 1-heptene, 1-octene, 1-nonene, 1-decene, 1-undecene, 1-dodecene and a mixture thereof.

According to some embodiments of the present invention, the alpha-olefin is propylene.

According to an aspect of some embodiments of the present invention there is provided a polymer or copolymer of an alpha-olefin, prepared by any of the processes described herein.

According to some embodiments of the present invention, the polymer or copolymer is characterized by an isotacticity degree of [mmmm] of at least 50%.

According to some embodiments of the present invention, the isotacticity degree is higher than [mmmm] of 90%.

According to some embodiments of the present invention, the isotacticity degree is higher than [mmmm] of 95%.

According to some embodiments of the present invention, the isotacticity degree is higher than [mmmm] of 99.0%.

According to some embodiments of the present invention, the polymer or copolymer is characterized by a molecular weight of at least $M_w$=300000 grams/mol.

According to some embodiments of the present invention, the polymer or copolymer is characterized by a molecular weight/molecular number value that ranges from 1.1 to 6.

According to some embodiments of the present invention, the polymer or copolymer has a heat fusion of from 1 to 200 J/gram.

According to an aspect of some embodiments of the present invention there is provided a Salan compound comprising two substituted or unsubstituted phenol moieties and a sequential diamino-containing skeleton unit linking the phenol moieties, the sequential diamino-containing skeleton unit being non-symmetric.

According to some embodiments of the present invention, the Salan compound is characterized as being capable of wrapping around a group 4 element is a fac-mer configuration.

According to some embodiments of the present invention, the Salan compound is represented by the general Formula I:

Formula I

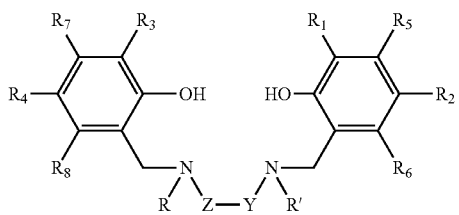

wherein:

Z and Y are each independently a substituted or unsubstituted alkylene chain being from 1 to 5 carbon atoms in length, such that Z and Y together form an alkylene chain that is 2 to 10 carbon atoms in length; each of $R_1$-$R_8$ is independently selected from the group consisting of hydrogen, alkyl, cycloalkyl, aryl, halogen, alkoxy, aryloxy, heteroalicyclic, heteroaryl, and nitro; and each of R and R' is independently selected from the group consisting of hydrogen, alkyl, cycloalkyl, and aryl, provided that (i) at least one of and R' is hydrogen; and/or (ii) if R and R' are the same, Y is different from Z.

According to some embodiments of the present invention, at least one of $R_1$-$R_4$ is halogen.

According to an aspect of some embodiments of the present invention there is provided a metal complex comprising the Salan ligand of any of claims 45-47, being wrapped around a group 4 element.

According to an aspect of some embodiments of the present invention there is provided a metal complex comprising a group 4 element and a Salan ligand being coordinatively attached to the group 4 element, wherein the Salan ligand is capable wrapping around the group 4 element in a fac-mer configuration and/or wherein the metal complex is devoid of a symmetry element.

According to an aspect of some embodiments of the present invention there is provided a metal complex comprising a group 4 element and a Salan ligand being coordinatively attached to the group 4 element, the Salan ligand comprising two substituted or unsubstituted phenol and a sequential diamino-containing skeleton unit linking the phenol moieties, wherein the sequential diamino-containing skeleton unit is non-symmetric.

According to some embodiments of the present invention, the metal complex is represented by the general formula II:

Formula II

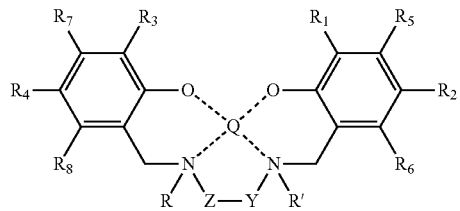

wherein:

Q is MXn, whereas M is a group 4 element; X is a labile group; and n is 0, 1, 2, 3 or 4;

Z and Y are each independently a substituted or unsubstituted alkylene chain being from 1 to 5 carbon atoms in length, such that Z and Y form together an alkylene chain that is 2 to 10 carbon atoms in length;

each of $R_1$-$R_8$ is independently selected from the group consisting of hydrogen, alkyl, cycloalkyl, aryl, halogen, alkoxy, aryloxy, heteroalicyclic, heteroaryl, and nitro, provided that at least one of $R_1$-$R_4$ is other than hydrogen; and each of R and R' is independently selected from the group consisting of hydrogen, alkyl, cycloalkyl and aryl, provided that (i) at least one of and R' is hydrogen; and/or (ii) if R and R' are the same, Y is different from Z.

The following embodiments concern Formulae I and II.

According to some embodiments of the present invention, Z and Y form together an alkylene chain being from 2 to 6 carbon atoms in length.

According to some embodiments of the present invention, Z is selected from the group consisting of (CRaRb), (CRaRb)(CRcRd) and (CRaRb)(CRcRd)(CReRf), and Y is selected from the group consisting of (CRgRh), (CRgRh)(CRiRj) and (CRgRh)(CRiRj)(CRkRp), wherein each of Ra-Rp are independently selected from the group consisting of hydrogen, alkyl, cycloalkyl, aryl, halogen, alkoxy, aryloxy, and/or at least two of Ra-Rp, R' and R form together a five- or six-membered, aromatic or non-aromatic ring.

According to some embodiments of the present invention, at least two of $R_1$-$R_4$ are each independently halogen.

According to some embodiments of the present invention, each of $R_1$-$R_4$ is independently halogen.

According to some embodiments of the present invention, at least one of $R_1$-$R_4$ is a bulky group.

According to some embodiments of the present invention, $R_1$ is the bulky group.

According to some embodiments of the present invention, each of $R_1$-$R_4$ is the bulky group.

According to some embodiments of the present invention, the bulky group is a rigid bulky group.

According to some embodiments of the present invention, the rigid bulky group is adamantyl.

According to some embodiments of the present invention, $R_1$ is 1-adamantyl.

According to some embodiments of the present invention, $R_2$ is alkyl.

According to some embodiments of the present invention, at least one of $R_3$ and $R_4$ is halogen.

According to some embodiments of the present invention, each of $R_3$ and $R_4$ is halogen.

According to some embodiments of the present invention, R' is hydrogen.

According to some embodiments of the present invention, R is alkyl.

According to some embodiments of the present invention, Y is (CRgRh).

According to some embodiments of the present invention, Z is (CRaRb).

According to some embodiments of the present invention, Ra, Rb, Rg and Rh are each hydrogen.

According to some embodiments of the present invention, Ra and R form together the ring.

According to some embodiments of the present invention, Rb, Rh and Rg are each hydrogen.

According to some embodiments of the present invention, Ra, Rb, Rg and Rh form together an aromatic ring.

According to some embodiments of the present invention, Y is (CRgRh)(CRiRj).

According to some embodiments of the present invention, Z is (CRaRb).

According to some embodiments of the present invention, Ra, Rb and Rg-Rj are each hydrogen.

According to some embodiments of the present invention, R' is hydrogen.

According to some embodiments of the present invention, Rg-Rj form together an aromatic ring.

According to some embodiments of the present invention, R and R' are each independently selected from the group consisting of hydrogen and alkyl.

According to an aspect of some embodiments of the present invention there is provided a catalyst system comprising the metal complex as described herein and a co-catalyst.

According to some embodiments of the present invention, the co-catalyst is an alumoxane.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
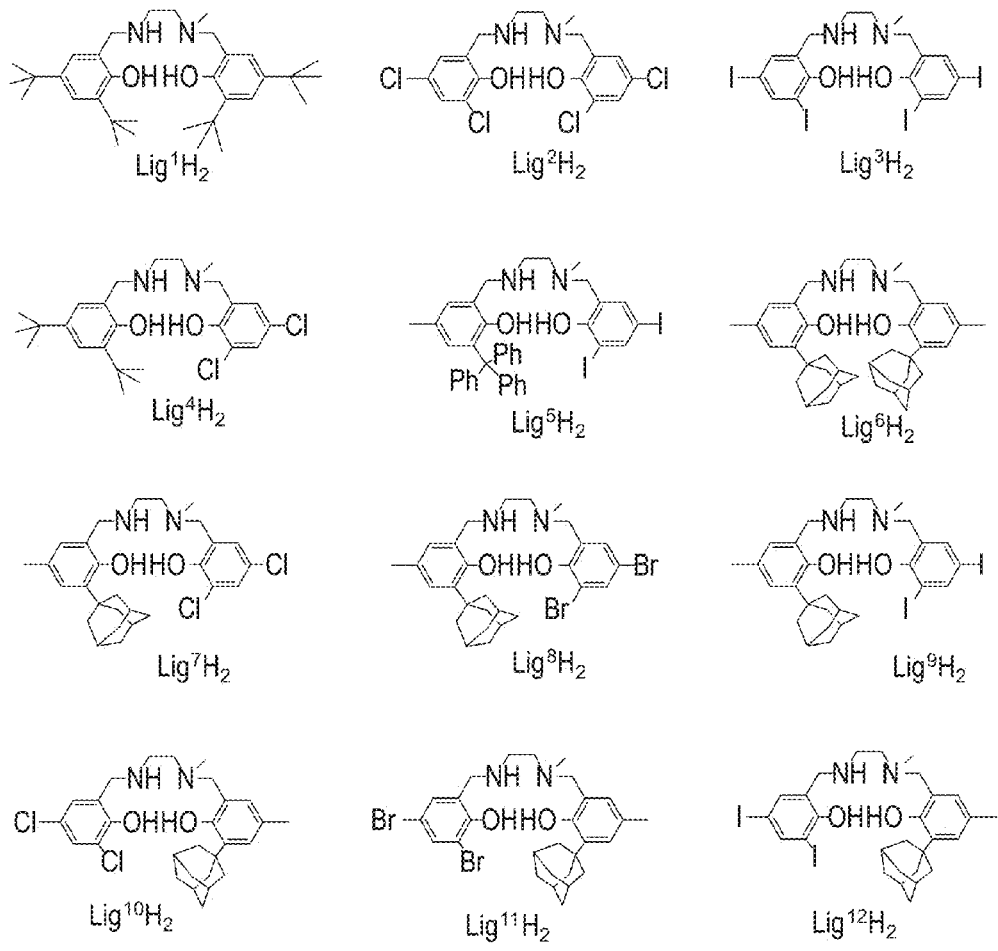
FIGS. 1A-B presents the chemical structures of exemplary Salan ligand precursors according to some embodiments of the present invention, based on an N-alkyl-ethylenediamine skeleton (wherein in FIG. 1A the N-alkyl is N-methyl, and in FIG. 1B the N-alkyl comprises an alkyl other than methyl) (Lig$^{1-17}$H$_2$)

The present invention, in some embodiments thereof, relates to chemical syntheses and, more particularly, but not exclusively, to novel processes of olefin polymerization, to catalyst systems which comprise, as pre-catalysts, metal complexes of Salan ligands which can be utilized in these processes, and to Salan ligand precursors for preparing these complexes.

Some embodiments of the present invention therefore relate to novel Salan-H$_2$ ligand precursors (or Salan compounds).

Some embodiments of the present invention relate to metal complexes of the type [(Salan)MX$_2$] wherein M is a group 4 element and X is a labile group, which serve as pre-catalysts.

Some embodiments of the present invention relate to catalyst systems comprising the pre-catalysts described herein and a co-catalyst.

Some embodiments of the present invention relate to processes of polymerizing alpha-olefins, which utilize the catalyst systems disclosed herein, and to polymers obtained by these processes.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Ample research efforts currently focus on a search for accessible catalysts that will lead to poly(alpha-olefin) polymers of well-defined properties, including high molecular weights, narrow molecular weight distributions and high stereoregularities (tacticities). In particular, highly active catalysts that will enable the controlled isospecific homopolymerization of propylene, and the copolymerization of propylene with other monomers such as ethylene are highly sought.

In general, isospecific catalysts are capable of discriminating between the two enantiotopic faces of an incoming olefin. This is achieved by the different interactions of these faces with the preferred conformation of the bound polymeryl chain oriented by its interactions with substituents in the vicinity of the chiral metal environment. C$_2$-symmetric catalysts are relatively accessible and their two coordination sites are homotopic, so their isospecificity induction is independent of possible epimerization events of the polymeryl chain. C$_1$-symmetric complexes are structurally more diverse, however, the directing abilities of their two diastereotopic sites are usually different. It has been recognized that isospecific C$_1$-symmetric catalysts should include a directional polymeryl chain migration to the more selective site [Busico et al., *Macromolecules* 1997, 30, 4786-4790].

The present inventors have now devised and successfully prepared and practiced a novel family of Salan-based ligand precursors, and a novel family of group 4 complexes of these novel Salan ligands. The present inventors have shown that these complexes act as pre-catalysts, which, upon activation with common co-catalysts (such as methylalumoxane, MAO), act as active catalysts, which, in the presence of an alpha-olefin monomer yield poly(alpha-olefin) polymers.

Salan-type ligands are "sequential" tetradentate dianionic ligands that include neutral amine donors and two anionic phenolate arms connected via a single carbon bridge to the two amine donors.

In contrast to the Salan-type complexes described in the art hitherto, the Salan ligands disclosed herein, when used for forming Salan-type pre-catalysts in catalyst systems, enable the required combination of high activity and high isospecificity in propylene polymerization.

The disclosed catalyst systems rely on Salan ligands that are designed so as to wrap around octahedral group 4 metals in a non-symmetric manner, described as fac-mer or cis-beta mode, which is not the common wrapping mode of previously described Salan ligands (which is fac-fac or cis-alpha for the octahedral pre-catalysts). This is attained by selection of substituents on the Salan ligand framework, as is further detailed hereinbelow.

The present inventors have envisioned that by utilizing Salan ligands which are characterized by a diamine skeleton, as defined herein, which is non-symmetric, for forming metal complexes with group 4 elements which are devoid of a symmetry element, different environments of the two labile groups in the complex would be achieved. It was further envisioned that these different environments may affect the activities and stereoregulating abilities of potential polymerization catalysts.

Without being bound by any particular theory, it was assumed that the non-symmetric skeleton of the Salan ligands results in a unique wrapping mode of Salan ligands around group 4 metals, presumably a fac-mer wrapping mode, which leads to the different environments of the labile groups in the metal complexes.

Thus, as a non-limiting example, in the Salan ligands disclosed herein, one of the N-alkyl units in a conventional Salan ligand is replaced with an N-H unit (or an N-D unit, wherein D is deuterium), thereby resulting in a non-symmetric skeleton of the Salan ligand and in Salan-type metal complexes that act as pre-catalysts in catalysts systems that are highly active and produce highly stereoregular polymers.

A variety of such ligand precursors (Salan compounds) that feature an N-H unit, and/or feature various other sequential diamino-containing skeleton units that link the two phenol moieties in the ligand, and/or various combinations of phenol substituents, is thus disclosed herein. The Salan ligand precursors can be employed in the formation of octahedral group 4 Salan-type metal complexes (titanium, zirconium, or hafnium). The complexes formed with these ligands (which serve as pre-catalysts in the processes disclosed herein) typically lack a symmetry element, as discussed in further detail hereinbelow.

While reducing the present invention to practice, group 4 metal complexes obtained with the Salan ligands as disclosed herein were prepared, and the application of such complexes in polymerization of various polyolefins was demonstrated.

Further while reducing the present invention to practice, it was demonstrated that the properties of the polymer can be tuned by selecting the appropriate [(Salan)MX$_2$]-type complex. In some examples, pre-catalysts of this family lead to exceptionally highly isotactic polypropylene (e.g., higher than 99%), as determined, for example, by $^{13}$C NMR, and can be appreciated from the obtained melting transitions T$_m$ (and heats of fusion ΔH (J/g)), which, in some example, were found to be higher than 160° C. and even as high as 168° C. These high isotacticities affect the physical properties of the polymer. Pre-catalysts of this family were also shown to be highly active catalysts, with exemplary activities being as high as 10000 g(polypropylene)·mmol$^{-1}$·h$^{-1}$. Pre-catalysts of this family also resulted in polypropylenes with exceptionally high molecular weights (e.g., higher than 300,000 grams/mol, and even higher than 1,000,000 grams/mol) and low PDI (e.g., Mw/Mn value lower than 3).

The Salan complexes were found to be suitable for polymerization of liquid propylene with 500 mol equivalents of MAO as co-catalyst. The Salan complexes of all tested group 4 metals, Ti, Zr and Hf, were found to exhibit high catalytic activities.

The Salan complexes disclosed herein were found to be active both in solventless polymerization and in polymerization in solution, at room temperature, and at lower and higher temperatures, indicating that the catalyst retains its activity and isospecificity under lower concentrations of the alpha-olefin.

It is to be noted that the catalyst systems described herein exhibit controlled-tacticity in polymerization of alpha-olefins, such that the degree and nature of stereoregularity can be pre-determined by the catalyst system of choice. These catalysts therefore can be utilized for producing isotactic polymers as well as elastomers of alpha-olefins, as desired.

It is to be further noted that the degree of chain elongation can be pre-determined by the catalyst system of choice. These catalysts therefore can be utilized for producing polymers of alpha-olefins with varying molecular weights.

It is to be further noted that the catalyst systems described herein show very high stereocontrol in polymerization of both higher olefin monomers such as 1-hexene and 1,5-hexadiene and of "slimmer" monomers such as ethylene and propylene.

The readily accessible family of Salan-group 4 metal complexes introduced herein in exemplary embodiments of the invention represents an isoselective homogeneous catalyst system, matching or even exceeding the latest generation Ziegler-Natta catalysts.

The Salan-Type Compound:

As discussed hereinabove, a novel family of Salan-type compounds has been designed and successfully prepared and practiced.

Herein, the phrase "Salan-type compound" describes a compound that includes two amine donors and two phenolic arms, each connected via a single carbon (one-carbon) linker to an amine donor.

The amine donors in Salan-type compounds are typically connected to one another via a bridging moiety, and form together the Salan skeleton, to which the phenolic arms are connected.

Thus, in other words, the phrase "Salan-type compound" describes a compound that comprises two substituted or unsubstituted phenol moieties and a sequential diamino-containing skeleton unit linking the phenol moieties.

The phrase "sequential diamino-containing skeleton unit" is used herein to describe a unit that comprises a one-carbon linker (e.g., methylene, or CH$_2$, or a single carbon substituted by one or more substituents, as defined herein for "alkyl") attached to one phenol moiety, one amino group (also referred to herein and in the art as N-donor or an amine donor) linked to the one-carbon linker, a bridging unit of two or more atoms (preferably including one or more carbon atom(s), optionally substituted and optionally interrupted by one or more heteroatoms) linked to one amino group at one end and to the other amino group at its other end, and another one-carbon linker connecting to the other amino group to the other phenol moiety. Thus, the sequential unit comprises the following sequence: (one-carbon linker1)-amine1-bridginng unit-amine2-(one-carbon linker2).

The phrase "sequential diamino-containing skeleton unit" is also referred to herein interchangeably simply as the skeleton of the Salan compound or ligand or as a "sequential skeleton unit" or "skeleton unit".

The Salan-type compounds described herein are also referred to herein, interchangeably, as "Salan compounds", "ligand precursors" or "Salan-type ligands" or "Salan ligand precursors", or as [Salan]H$_2$.

Salan-type compounds are known as sequential tetradentate dianionic ligands that readily form organometallic complexes with group 4 elements such as Ti, Zr and Hf, and with analogous elements, as defined herein.

The Salan compounds disclosed herein have been uniquely designed so as to include a non-symmetric (or non-palindromic) skeleton, as defined herein.

In some embodiments, the Salan ligands disclosed herein are designed so as to include a sequential diamino-containing skeleton unit, as defined herein, which is non-symmetric (or non-palindromic).

By "non-symmetric" it is meant that the sequential diamino-containing skeleton unit connecting the two phenol moieties of the Salan compound is observed differently when starting from one phenol and when starting from the other phenol.

Taking the sequential skeleton unit as defined above to be (one-carbon linker1)-amine1-bridginng unit-amine2-(one-carbon linker2), such a unit can be such that one-carbon linker1 is connected to phenol1 and one-carbon linker2 is connected to phenol2 or such that one-carbon linked is connected to phenol2 and one-carbon linker 2 is connected to phenol1. A symmetric unit would be the same if observed from phenol1 to phenol 2 and vice versa, from phenol 2 to phenol 1, since, for example, the two amines, amine1 and amine2 are the same. Such a symmetric unit can be seen as a palindromic unit. A non-symmetric unit would be differently observed when considered from phenol1 to phenol2 compared to from phenol2 to phenol1. Such a non-symmetric unit can therefore be regarded as "non-palindromic" since the sequence (one-carbon linker1)-amine1-bridging unit-amine2-(one-carbon linker2), and its inversed sequence (one-carbon linker2)-amine2-bridginng unit-amine1-(one-carbon linker1), when taken in that order (left-to-right), are not identical.

As used herein, the expression "palindromic" describes a sequence of moieties that can be read the same way in either direction. The expression "non-palindromic" thus describes a sequence of moieties, as in the sequential skeleton of the Salan compound described herein, which cannot be read the same way in either direction, namely, from one phenol moiety to another phenol moiety.

Salan-type compounds which have such a non-symmetric (or non-palindromic) skeleton unit can be readily determined by those skilled in the art, simply based on their 2-D chemical structure. Methods which can be used to determine Salan-type compounds that have such a non-symmetric skeleton unit include, but are not limited to, NMR measurements including $^1$H NMR and $^{13}$C NMR. While symmetric Salan-type compounds are characterized by having a lower number of absorptions since some groups in the molecule are related by symmetry elements, non-symmetric Salan-type compounds would be characterized by a higher number of absorptions in both their $^1$H NMR and $^{13}$C NMR spectra, and in addition, their 1H absorptions may be more complicated (e.g., multiplets instead of singlets), since loss of symmetry elements has resulted in the transformation of homotopic groups to diastereotopic groups).

Without being bound to any particular theory, it is suggested that the non-symmetric skeleton of the Salan ligand encourages a unique wrapping mode of the Salan ligands around group 4 elements (or analogous elements), which in turn, encourages different environment of the labile groups in the formed complexes, as is further detailed herein. It is suggested that the non-symmetric skeleton unit of the Salan ligand may lead to a fac-mer wrapping mode of the Salan ligand around the group 4 element.

According to an aspect of some embodiments of the present invention, there is provided a Salan ligand that is capable of wrapping around a group 4 element in a fac-mer configuration.

The uniquely designed Salan ligands disclosed herein can be collectively represented by general Formula I:

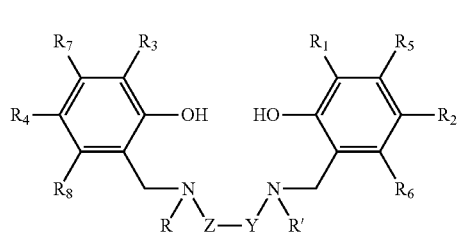

Formula I wherein:

Z and Y are each independently a substituted or unsubstituted alkylene chain being from 1 to 5 carbon atoms in length, such that Z and Y together form an alkylene chain that is 2 to 10 carbon atoms in length;

each of $R_1$-$R_8$ is independently selected from the group consisting of hydrogen, alkyl, cycloalkyl, aryl, halogen, alkoxy, aryloxy, heteroalicyclic, heteroaryl, and nitro; and each of R and R' is independently selected from the group consisting of hydrogen, alkyl, cycloalkyl, and aryl.

In Formula I, the moiety formed by —$CH_2$—(R)N—Z—Y—N(R')—$CH_2$— represents the sequential skeleton unit, as defined herein, of the Salan-type compounds. The ($CH_2$) moieties represent the one-carbon linkers described herein; N(R) and N(R') represent the two amines (or amine donors) described herein; and the submoiety "Z—Y" represents the bridging unit that connects the amine donors in the Salan moiety. This unit, Z—Y, is also referred to herein as "bridge", "bridging unit" or "bridging moiety", and all of these expressions are used interchangeably.

It is noted that the variable "Y" when used within the Formulae described herein does not represent the element Yttrium (often denoted "Y") but rather solely represents the possible groups or moieties as defined for this variable in each of the formulae described herein.

In some embodiments, the moiety formed by —$CH_2$—(R)N—Z—Y—N(R')—$CH_2$— (the sequential skeleton unit) is non-symmetric, or non-palindromic, as defined herein.

In some embodiments, the non-symmetry in the Salan skeleton is imparted by non-identical (different) substituents on the two N-donors; either one of the N-donors substituents (R or R') is hydrogen or deuterium and the other is alkyl, cycloalkyl or aryl.

Herein, the term "different" as used for R and R' in the Formulae herein, indicates that these substituents differ from each other by at least one atom or are different isomerically.

In some embodiments, the non-symmetry of the Salan skeleton is imparted, when both N-donors substituents (R and R') are hydrogen or are the same alkyl, cycloalkyl or aryl, and also when the two N-donors are identical, by a bridging moiety that connects the N-donors (denoted as Z—Y) which is non-symmetric (or non-palindromic, as defined herein).

A non-symmetric bridging moiety, denoted as Z—Y, is imparted by Z and Y being different.

Herein, the term "different" as used for Z and Y in the Formulae herein, indicates that these moieties differ from each other by at least one atom or are different isomerically.

When Z and Y form together the bridging moiety, Z would be considered as different from Y, in cases where dividing the Z—Y moiety to two equal portions, based on the number of atoms of the entire Z—Y moiety, results in two moieties that differ from each other by at least one atom or are different isomerically.

Thus, for example, in cases where Z—Y form a 2-carbon alkylene, dividing the Z-Y moiety into Z and Y would result in two single-carbon moieties. Such single-carbon moieties would be different if, for example they are differently substituted. In another example, in cases where Z and Y form a 3-carbon alkylene, dividing the Z—Y moiety would result in an axis that crosses the middle carbon. In such a case, the two artificially-formed moieties would be different if, for example, the remaining carbon atom in Y and the remaining carbon atom in Z are differently substituted.

In some embodiments, Z and Y are different in the sense they are non-palindromic within the sequential skeleton unit defined herein.

Thus, for example, replacing the expression "bridging unit" in the sequential unit as defined herein, by "Z—Y" as in Formula I, makes a sequential unit being one-carbon linker1)-amine1-Z—Y-amine2-(one-carbon linker2). If Z is different from Y, as defined herein, the sequence (one-carbon linker1)-amine1-Z—Y-amine2-(one-carbon linker2), and its inversed sequence with respect to Y and Z, (one-carbon linker1)-amine1-Y-Z-amine2-(one-carbon linker2), when taken in that order (left-to-right), are not identical, even if amine1=amine2 and one-carbon linker1=one-carbon linker2).

The moiety Z—Y can therefore be non-palindromic within the skeleton unit, as defined herein.

While currently known Salan-type compounds possess a skeleton in which the substituents on the two amine donors (R and R' in Formula I) are the same, and are each typically the same alkyl, in some embodiments, the Salan ligands disclosed herein include amine donors which are differently substituted, such that R and R' in Formula I are different from one another.

Thus, in some embodiments, at least one of R and R' is hydrogen.

As used herein, reference to "hydrogen" (or H) also encompasses hydrogen isotopes such as Deuterium (D).

Alternatively, R and R' are each hydrogen (or an isotope thereof).

Further alternatively, R and R' are both different from hydrogen and are the same.

In embodiments where R and R' are the same, Z and Y are selected such that the skeleton in non-symmetric, (or non-palindromic) as defined herein.

Thus, in some embodiments, in cases where both R and R' are the same (e.g., both R and R' are hydrogen or the same alkyl), Z is different from Y, as defined herein.

In some embodiments, Z and Y form together a substituted or unsubstituted alkylene chain being at least 2 carbon atoms in length.

In some embodiments, the alkylene chain is 2, 3, 4, 5, 6, 7, 8, 9 and even 10 carbon atoms in length.

By "in length" it is meant the number of carbon atoms that form the backbone of an alkylene chain.

In some embodiments, Z and Y form together a substituted or unsubstituted alkylene chain being from 2 to 6 carbon atoms in length.

Thus, in some embodiments, Z can be an alkylene chain being 1, 2 or 3 carbon atoms in length, and can be represented as (CRaRb), (CRaRb)(CRcRd) or (CRaRb)(CRcRd)(CReRf), respectively; and Y can be an alkylene chain being 1, 2 or 3 carbon atoms in length, and can be represented as (CRgRh), (CRgRh)(CRiRj) or (CRgRh)(CRiRj)(CRkRp), respectively, wherein each of Ra-Rp are independently selected from the group consisting of hydrogen, alkyl, cycloalkyl, aryl, halogen, alkoxy, aryloxy, and/or at least two of Ra-Rp, R' and R form together a five- or six-membered, aromatic or non-aromatic ring.

In some embodiments, Z and Y form together an alkylene chain being 2 carbon atoms in length. In these embodiments, the Salan ligand precursor has a 1,2-diaminoethane skeleton.

In these embodiments, Y can be represented as (CRgRh) and Z can be represented as (CRaRb), as defined herein.

In some embodiments, Ra, Rb, Rg and Rh are each hydrogen (such that Z and Y are identical).

In these embodiments, one of R and R' is hydrogen and the other is not hydrogen. In some embodiments, one of R and R' is hydrogen and the other is alkyl.

In any of the embodiments described herein, when R or R' is an alkyl, the alkyl can be, for example, methyl, ethyl, propyl, isopropyl, or a higher alkyl (e.g., of 4, 5, 6 or more carbon atoms), or can be an aralkyl (an alkyl substituted by an aryl, as defined herein) such as benzyl.

In some of these embodiments, the alkyl is methyl.

In some of these embodiments, R' is hydrogen.

In some of these embodiments, R' is hydrogen and R is alkyl (e.g., methyl).

In other embodiments, when Z and Y form together an alkylene chain being 2 carbon atoms in length, as described herein, one of R and R' form together a ring with one of the carbon atoms in the alkylene chain (e.g., with one of Ra, Rb, Rg and Rh).

In some embodiments, R and Ra (in Z) form together a ring. In such embodiments, R' can be as defined herein, and is preferably hydrogen.

The ring formed by R and Ra is a heterocyclic ring which includes the amine-nitrogen of the skeleton.

In some embodiments, R and Ra form together a 5-membered (substituted or unsubstituted) heteroalicyclic ring. In some embodiments, R and Ra form together a pyrrolidine (substituted or unsubstituted), such that the Salan ligand precursor has a skeleton of 2-aminomethyl-pyrrolidine, which imparts chirality to the ligand precursor. Alternatively, R and Ra can form a heterocyclic ring such as piperidine, morpholine, piperazine, tetrahydroazepine and the like, each being substituted or unsubstituted.

In some of the embodiments where R and Ra form together a ring, as described herein, Rb, Rh and Rg are each hydrogen.

In some of these embodiments, R' is hydrogen. Alternatively, R' is as defined herein, as long as it is different from R (namely, it does not form the same ring with, e.g., Rh).

In other embodiments, when Z and Y form together an alkylene chain being 2 carbon atoms in length, as described herein, at least two of Ra, Rb, Rg and Rh form together a ring. The ring can be a cycloalkyl, a heteroalicyclic, an aryl or an heteroaryl.

In some of these embodiments, at least one of R and R' is hydrogen.

In some of these embodiments, R' is hydrogen.

In some of these embodiments, R' is hydrogen and R is alkyl, as described herein.

In some embodiments, the ring is a cycloalkyl, such as cyclohexane, and in some embodiments, the ring is trans-cyclohexane, which imparts chirality to the skeleton.

In some embodiments, the ring is an aryl (an aromatic ring), such as phenyl.

Thus, in some of the embodiments where Z and Y form together an ethane bridge within the diamine skeleton of the Salan ligand, a chirality is imparted to the skeleton either by one of R and R' being hydrogen (preferably R' being hydrogen) and/or by a formation of a heterocylic ring by one of R and R' and one of the carbon atoms in the alkylene bridge.

In some embodiments, Z and Y form together an alkylene chain being 3 carbon atoms in length.

In these embodiments, Y can be represented as (CRgRh)(CRiRj) and Z can be represented as (CRaRb).

In some embodiments, Ra, Rb and Rg-Rj are each hydrogen.

In these embodiments, one of R and R' is hydrogen and the other is not hydrogen. In some embodiments, one of R and R' is hydrogen and the other is alkyl, as described herein.

In some of these embodiments, R' is hydrogen.

In some of these embodiments, R' is hydrogen and R is alkyl, as described herein (e.g., methyl).

In some embodiments, when Z and Y form together an alkylene chain being 3 carbon atoms in length, as described herein, at least two of Ra, Rb and Rg-Rj form together a ring. The ring can be a cycloalkyl, a heteroalicylic, an aryl or a heteroaryl.

In some of these embodiments, at least one of R and R' is hydrogen.

In some of these embodiments, R' is hydrogen.

In some of these embodiments, R' is hydrogen and R is alkyl, as described herein.

In some of these embodiments, R and R' are each hydrogen.

In some of these embodiments, R and R' are both other than hydrogen and can be the same or different.

In some of these embodiments, R and R' are both alkyl, as described herein.

In some of these embodiments, R and R' are the same alkyl (e.g., methyl).

In some embodiments, the ring is a cycloalkyl, such as cyclohexane, cyclopentane, and the like.

In some of these embodiments, the ring is an aryl (an aromatic ring), as defined herein, such as, for example, phenyl. Alternatively, the ring is a heteroaryl, as defined herein.

In some of these embodiments, the ring is formed by Rg-Rj, such that Y is phenyl.

Alternatively, the ring is formed by Ra, Rb, Rg and Rh.

Further alternatively, when Z and Y form together an alkylene chain being 3 carbon atoms in length, as described herein, R or R' form together a ring with one of Ra, Rb and Rg-Rj, as described herein for a ring formed by R and Ra.

In some of these embodiments, R and Ra form together a heterocylic (heteroalicyclic) ring, as described herein.

In some of these embodiments, Rg-Rj are each hydrogen.

Further in some of these embodiments, R' is hydrogen. Alternatively, R' is as defined herein.

In some of these embodiments, R' and Rj form together a heterocylic ring, as described herein for R and Ra. In some of these embodiments, Ra, Rb, Rg, Rh and Ri are each hydrogen.

Further in some of these embodiments, R is hydrogen. Alternatively, R is as defined herein.

Thus, in some of the embodiments where Z and Y form together an alkylene bridge of 3 carbon atoms within the diamino-containing sequential skeleton of the Salan ligand precursor, chirality is imparted to the skeleton either by one of R and R' being hydrogen (preferably R' being hydrogen) and/or by a presence of a ring within the skeleton, whereby the ring can include 2 of the 3 carbon atoms of the bridge between the amine donors or can include one of the amine donors and an adjacent carbon.

Similarly, in cases where Z and Y form together an alkylene bridge of 4, 5, 6 or more carbon atoms, chirality is imparted to the skeleton either by one of R and R'; being hydrogen and/or by a presence of a heterocylic ring that includes one of the amine donors and an adjacent carbon atom and/or by a presence of ring within the bridge (within Y or Z), as long as the number of carbon atoms between the ring and one amine donor is different from the number of carbon atoms between the ring and the other amine donor.

It is to be noted that in any of the embodiments described herein, the bridge formed by X and Y can include substituents other than those described in detail herein, as long as these substituents do not affect the performance of the corresponding Salan ligand or of a metal complex containing same.

As known in the art, the performance of an organometallic complex that includes a Salan ligand is affected by the electronic and steric nature of the substituents of the phenolate rings of the Salan ligand, denoted as $R_1$-$R_8$ in Formulae I and II herein. The performance is particularly affected by the electronic and steric nature of the substituents of the phenolate rings at positions ortho and para to the phenolate oxygens, denoted as $R_1$-$R_4$ in Formulae I and II herein.

Accordingly, in some embodiments, at least one of $R_1$-$R_4$ is other than hydrogen.

In some embodiments, each of $R_1$-$R_4$ is independently selected from the group consisting of hydrogen, alkyl (e.g., methyl, ethyl, propyl, isopropyl, butyl, isobutyl, tert-butyl, pentyl and isomers thereof, hexyl and isomers thereof, octyl, nonyl, dodecyl and the like, as well as aralkyls such as trityl, cumyl, benzyl and the like), halogen (e.g., chloro, fluoro, bromo or iodo), and cycloalkyl (e.g., cyclopentane, cyclopropyl, cyclohexane, cycloheptane, and bulkier cycloalkyls, such as bicyclic groups of 7 or more carbon atoms, including adamentyl as an example).

In some embodiments, $R_5$-$R_8$ are each hydrogen, although other substituents at these positions are also contemplated. In some embodiments, $R_5$-$R_8$ can each independently be hydrogen, or alkyl (e.g., methyl, ethyl, propyl, isopropyl, butyl, isobutyl, tert-butyl, pentyl and isomers thereof, hexyl and isomers thereof, octyl, nonyl, dodecyl and the like).

As demonstrated herein, it has been shown that Salan ligands possessing electron withdrawing substituents such as halogens and/or bulky substituents on one or more of the phenolate rings provide for improved performance of the metal complexes formed therewith.

In some embodiments, at least one of $R_1$-$R_4$ is halogen.

In some embodiments, at least one of $R_1$ and $R_2$ is halogen.

In some embodiments, at least one of $R_3$ and $R_4$ is halogen.

In some embodiments, at least two of $R_1$-$R_4$ are each independently halogen, the halogen being the same or different and is preferably the same.

In some embodiments, $R_1$ and $R_2$ are each halogen.

In some embodiments, $R_3$ and $R_4$ are each halogen.

In some embodiments, each of $R_1$-$R_4$ is independently halogen.

The halogen can be chloro, bromo, and iodo, and any combination thereof.

In some embodiments, each of $R_1$-$R_4$ is chloro, each of $R_1$-$R_4$ is bromo, or each of $R_1$-$R_4$ is iodo.

In some embodiments, each of $R_3$ and $R_4$ is chloro, each of $R_3$ and $R_4$ is bromo, or each of $R_3$ and $R_4$ is iodo.

In some embodiments, each of $R_1$ and $R_2$ is chloro, each of $R_1$ and $R_2$ is bromo, or each of $R_1$ and $R_2$ is iodo.

In some embodiments, whenever, one or more, but not all, of $R_1$-$R_4$ is halogen, the other substituent(s) can be, for example, a linear or branched alkyl and/or a bulky substituent, as defined herein.

In some embodiments, at least one of $R_1$-$R_4$ is a bulky substituent.

In some embodiments, at least $R_1$ is a bulky substituent, as defined herein.

In some embodiments, each of $R_1$-$R_4$ is said bulky group.

As used herein, the phrase "bulky" describes a group that occupies a large volume. A bulkiness of a group is determined by the number and size of the atoms composing the group, by their arrangement, and by the interactions between the atoms (e.g., bond lengths, repulsive interactions). Typically, lower, linear alkyls are less bulky than branched alkyls; bicyclic molecules are more bulky than cycloalkyls, etc.

In some embodiments, the bulky substituent is a branched and/or substituted alkyl or a cycloalkyl, each being of 7 carbon atoms or more.

Exemplary bulky branched alkyls include, but are not limited to, triphenylmethane (trityl) and cumyl. Other branched and/or substituted alkyls being 7 carbon atoms or more are also contemplated.

In some embodiments, the bulky substituent is a bulky rigid group.

In some embodiments, at least one of $R_1$-$R_4$ is a bulky rigid group.

As used herein, the phrase "bulky rigid group" describes a bulky group, as defined herein, with reduced number of free-rotating bonds. Such a group, unlike bulky alkyls, is rigid in terms of free rotation. Exemplary bulky rigid groups that are suitable for use in the context of embodiments of the invention include, but are not limited to, aryl, heteroaryl, cycloalkyl and/or heteroalicyclic, as defined herein.

In some embodiments, the rigid bulky group is an aryl, heteroaryl, cycloalkyl and/or heteroalicyclic, as defined herein, that has a total of 7 carbon atoms or more, each being substituted or unsubstituted.

In some embodiments, the bulky rigid group is a bicyclic group, comprising two or more of a cycloalkyl, aryl, heteroalicyclic or heteroaryl fused or linked to one another.

An exemplary bulky rigid group is adamantyl, for example, 1-adamantyl.

In some embodiments, $R_1$ is a bulky rigid (e.g., cyclic) group. In some embodiments $R_3$ is a bulky rigid group.

In some embodiments, $R_1$ and/or $R_3$ is adamantyl (e.g., 1-adamantyl).

In some embodiments, $R_1$ is adamantyl (e.g., 1-adamantyl).

In embodiments where at least one of $R_1$-$R_4$ is a bulky substituent, other substituents at these positions ($R_1$-$R_4$) can be for example, lower alkyl (e.g., methyl), another bulky substituent, as described herein, or one or more electron-withdrawing groups such as halogen.

In some embodiments, $R_1$ is adamantyl (e.g., 1-adamantyl), $R_2$ is alkyl (e.g., methyl) and one or both of $R_3$ and $R_4$ is halogen (e.g., chloro, bromo and/or iodo).

In some embodiments, $R_3$ is adamantyl (e.g., 1-adamantyl), $R_4$ is alkyl (e.g., methyl) and one or both of $R_1$ and $R_2$ is halogen (e.g., chloro, bromo or iodo).

The substituents on the phenol rings ($R_1$-$R_8$) can be modified by choice of the starting materials used for preparing the precursor ligand, as is further detailed hereinafter.

Further according to some embodiments the present invention, there are provided processes of preparing the Salan ligand precursors described herein.

The Salan ligand precursor can be prepared by any methods known in the art for preparing Salan-type compounds, using suitable starting materials for obtaining the desired asymmetry. An exemplary method is described in the Examples section that follows.

According to an aspect of some embodiments of the present invention, there is provided a process of preparing a Salan ligand precursor having the general Formula I, as described herein.

The process is effected by reacting a diamino compound having the formula R—NH—Z—Y—NR', wherein Z, Y, R and R' are as defined herein for Formula I, with a carbonyl-containing compound having the formula:

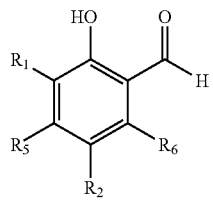

(a substituted salicylaldehyde or 2-hydroxybenzalaldehyde),
and/or with a compound having the formula:

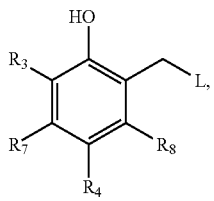

wherein L is a leaving group.

As used herein throughout, and is well known in the art, the phrase "leaving group" refers to a chemical moiety that can be easily replaced by a nucleophilic moiety in a nucleophilic reaction. Representative examples of leaving groups include, without limitation, halogen, alkoxy, aryloxy, thioalkoxy, thioaryloxy, sulfinyl, sulfonyl, carboxy and carbamyl, as these terms are defined hereinabove, with halogen and alkoxy being the presently most preferred. Additional examples of leaving groups include, without limitation, azide, sulfonamide, phosphonyl and phosphinyl.

In some embodiments, the leaving group L is halogen such as bromo.

In some embodiments, the process is effected by reacting the diamino compound with the substituted salicylaldehyde or 2-hydroxybenzalaldehyde to thereby obtain an imino-containing compound of the formula:

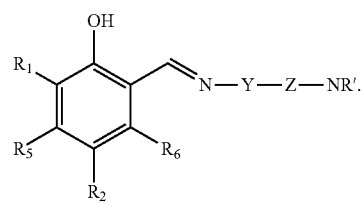

The reaction of forming the imine-containing compound is performed under conditions for performing a Schiff reaction, as known in the art.

Reacting the obtained imine-containing compound or of the starting diaimino compound, with the compound having the general Formula

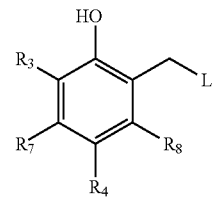

is performed under conditions suitable for performing a nucleophilic addition reaction, as known in the art.

Once the Schiff reaction is performed, a Salalen-type compound is obtained. This compound can be readily converted into a Salan-type compound by reducing the imine to amine. Any reducing agent and conditions can be used. In some embodiments, the reduction is performed in the presence of sodium borohydride as a reducing agent.

The substituents $R_1$-$R_8$ of the reactant determine the substitution pattern of the Salan ligand precursor and the metal complex formed therewith, described herein.

The Salan ligand precursors disclosed herein can therefore be synthesized by straightforward reaction sequences relying on either commercially available or easily-synthesized starting materials.

For example, the Salan ligand precursors possessing a secondary amine (R or R' in Formula I is hydrogen) and a 2-carbons or 3-carbons bridge are synthesized by a condensation of a primary amine of N(R)-diaminoethane or N(R)-diaminopropane (where R is as defined herein for Formula I) with a substituted salicylaldehyde, followed by nucleophilic attack of the secondary amine on a bromomethyl derivative of the appropriately substituted phenol, and finally a reduction of the imine to a secondary amine.

Salan ligand precursors possessing a secondary amine (R or R' in Formula I is hydrogen) and an aminomethylpyrrolidine (or e.g., other aminoalkylpyrrolidine) skeleton are prepared analogously from a respective aminoalkylpyrrolidine.

Salan ligand precursors possessing an aromatic ring within a 2-carbon atoms skeleton are obtained by analogous steps including condensation-substitution-reduction starting from a mono-N-substituted 1,2-diaminobenzene.

Salan ligand precursors an aromatic ring within a 3-carbon atoms or higher skeleton are obtained by condensing two equivalents of a substituted salicylaldehyde with a respective 2-aminoalkylaniline to form the corresponding bis(imine) compound, and reduction of the latter. Alternatively, a respective 2-aminoalkylaniline is reacted with two equivalents of a bromomethyl derivative of the appropriately substituted phenol.

Other synthetic pathways are also contemplated.

The methodology described herein can be further utilized for preparing any Salan-metal complex, including the Salan-group 4 metal complexes described herein.

Accordingly, in some embodiments, the process described herein further comprises reacting the compound having Formula I as prepared by the process described hereinabove, with a metallic reagent, as described herein. In some embodiments, such a process is used for preparing a metal complex having general Formula II, as described herein.

The Salan-Type Metal Complex (Pre-Catalyst):

Further according to an aspect of embodiments of the present invention, there are provided novel complexes of group 4 elements or of analogous elements. As discussed herein, such complexes can be efficiently used in catalytic systems, together with a co-catalyst, and are also referred to herein as pre-catalysts. The pre-catalysts comprise a group 4 element (or an analogous element) and a Salan ligand wrapped around the group 4 element. In some embodiments, these complexes are configured such that the Salan ligand is capable of wrapping around the group 4 element in a fac-mer configuration.

In the context of the present embodiments, the disclosed pre-catalyst is an organometallic complex of a group 4 element and a Salan ligand. However, while such complexes are typically characterized by a symmetric wrapping mode (configuration) of the ligand around the octahedral group 4 element, commonly described as fac-fac (where the two sets of donor groups, i.e., O1-N1-N2 and O2-N2-N1 are facial) or cis-alpha, the pre-catalysts disclosed herein are designed such that the complexes can adopt an asymmetric wrapping mode, which can be described as fac-mer (where one of the two sets of donor groups O1-N1-N2 and O2-N2-N1 is facial and the other is meridional) or cis-beta configuration.

In some embodiments, the pre-catalysts disclosed herein are devoid of a symmetry element, or, in other words, lack a symmetry element, as defined herein.

As used herein, the phrase "symmetry element" describes any of the known elements in molecular symmetry, namely, symmetry axis, symmetry plane, inversion center and rotation-reflection axis.

The phrase "devoid of a symmetry element" thus describes a compound which has none of the known elements of symmetry.

Without being bound to any particular theory, it is suggested that the lack of a symmetry element encourages an asymmetric fac-mer wrapping mode (configuration) of the Salan ligand around the center of the group 4 element.

The phrase "devoid of a symmetry element" thus describes an organometallic complex which has none of the known elements of symmetry, as defined herein.

A person skilled in the art would readily recognize those pre-catalysts in which the Salan ligand is capable of wrapping around a center of a group 4 metal in the fac-mer asymmetric mode. For example, a person skilled in the art would readily recognize that a Salan ligand has a non-symmetric sequential diamino-containing skeleton unit, as defined herein, is capable of wrapping around a group 4 element in a fac-mer wrapping configuration.

Thus, in some embodiments, the pre-catalyst comprises a Salan ligand that has a non-symmetric (or non-palindromic) sequential diamino-containing skeleton unit.

In some embodiments, the pre-catalyst is such that the Salan ligand is wrapping around the group 4 element in a fac-mer configuration.

A fac-mer wrapping mode of a Salan ligand around the group 4 element can be determined by methods known in the art, such as, for example, by determining the crystal structure of the pre-catalyst (e.g., by X-Ray crystallography).

The pre-catalyst is a metal complex of a group 4 metal and a Salan ligand. In some embodiments, the complex comprises one Salan ligand per one metal atom.

The expressions "a metal complex of a group 4 transition metal and a Salan ligand", "a Salan-group 4 metal complex" and "a group 4 metal atom having a Salan ligand complexed therewith" and other grammatical combinations of a metal and Salan, are used herein interchangeably.

In some embodiments, the group 4 metal is a group 4 transition metal such as titanium (Ti), zirconium (Zr) or Hafnium (Hf).

In some embodiments, the phrase "group 4 metal" also encompasses elements with a valence as in group 4 transition metals, which can be utilized within the pre-catalysts in a catalytic reaction (e.g., polymerization of alpha-olefins). Such elements are referred to herein as elements analogous to group 4 metals. Such analogous elements include, for example, scandium, yttrium and lanthanides with suitable valence (e.g., which can adopt an oxidation state of 0, 1, 2, 3 or 4).

In some embodiments, the metal complex can be represented as [Salan]MXn, wherein M is a group 4 element (or an analogous element) as described herein, X is a labile group and n is an integer of 0-4.

The oxidation state of the metal in the metal complex can be 0, 1 2, 3 or 4, and in some embodiments is 4. A Salan ligand is typically coordinated to the metal atom via two covalent bonds (via the phenolate oxygens) and two coordinative bonds (via the amine-nitrogens). Labile groups, denoted herein as X, and which are typically anionic groups, as well as neutral groups, may complete the coordination sphere of the metal.

Hence "n" is an integer that describes the number of labile groups that are attached to the metal atom, whereby additional groups can be present in case "n" labile groups do not complete the coordination sphere of the metal.

As used herein, the term "labile group" encompasses chemical groups which are attached to the metal atom, and which can be removed or replaced in the presence of a co-catalyst. Labile groups are typically univalent anionic groups. A "labile group" can be regarded as a ligand that participates in the catalytic reaction, as is sometimes referred to in the art as an "actor" ligand.

Exemplary labile groups include, but are not limited to, univalent anionic ligands such as a halide, a hydride, a saturated or unsaturated hydrocarbyl, an alkoxide, an aryloxide, a dialkylamide, or an arylamide, as well as divalent anionic ligands such as a cyclometallated hydrocarbyl.

In some embodiments, the oxidation state of the metal is 4, and the number of labile groups "n" is 2. In some embodiments, the oxidation state of the metal is 4, and the number of labile groups "n" is 1. In these embodiments, an additional group is attached to the metal.

The additional group(s) can be, for example, neutral univalent ligands such as, but not limited to, THF or toluene.

In some embodiments, the pre-catalyst is prepared from a Salan ligand precursor (Salan-H$_2$) as described herein (e.g., having general Formula I as described herein).

It is to be noted that the expression Salan-H$_2$ describes a ligand precursor, when not complexed to the group 4 element, whereby upon complexation, the phenolic functions are converted to phenolates (each loses a proton), so as to generate a Salan ligand.

According to some embodiments, the pre-catalysts disclosed herein can be collectively represented by the general formula II:

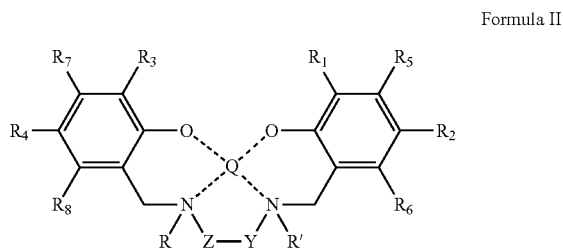

Formula II wherein:

Q is MXn, whereas M is a group 4 element (or an analogous element, as described herein); X is a labile group, as defined herein; and n is an integer ranging from 0 to 4;

and wherein all other variables are as described hereinabove for Salan ligand precursors having Formula I.

The pre-catalyst metal complex can be prepared by any methods known in the art. An exemplary method is described in the Examples section that follows. Alternatively, it can be prepared in situ, as described hereinbelow.

Further according to some embodiments of the invention there is provided a pre-catalyst comprising a group 4 element as described herein (e.g., as MXn) and any of the Salan ligands as described herein.

In some embodiment, a pre-catalyst is represented by general formula II as above, wherein M is Ti, Zr or Hf.

In some embodiments, M is Ti.

The oxidation state of the metal can be 0, 1, 2 3 or 4, and in some embodiments is 4. Labile groups, denoted as X in Formula I above, such as chloro, bromo, iodo, alkyl, alkoxy, etc., as well as neutral groups, may complete the coordination sphere of the metal.

The dashed lines represent the complexation between the metal atom and the Salan ligand. In some embodiments, the dashed lines represent covalent bonds formed between each of the phenolate oxygens and the metal atom and coordinative bonds between each of the nitrogen atoms and the metal atom.

In some embodiments, the Salan ligand is any of the Salan ligands described in Example 1 in the Examples section that follows, and/or presented in any of FIGS. 1-4.

In some embodiments, the R$_1$-R$_4$ substituents of the two phenolate groups are as described for Salan ligands that are useful in olefin polymerization, for example, as described in U.S. Pat. Nos. 6,632,899 and 6,686,490, which are incorporated by reference as if fully set forth herein).

The Catalyst System:

Further according to embodiments of the present invention there is provided a catalyst system comprising a pre-catalyst as described herein and a co-catalyst as described herein.

As used herein, the term "catalyst system" describes a chemical entity that functions as a catalyst for a polymerization reaction of an alpha-olefin. Herein, the chemical entity is comprised of a pre-catalyst and a co-catalyst which together form an active catalyst for e.g., a polymerization reaction.

Hereinafter, the term "pre-catalyst" refers to a chemical entity, in general, and to a chemical compound or complex, in particular, which, when activated by at least one "co-catalyst", becomes part of a catalyst system functional for catalytic polymerization of an alpha-olefin monomer, under proper polymerization reaction conditions. In general, without the presence of at least one co-catalyst, a pre-catalyst is ineffective for catalytic polymerization of an alpha-olefin monomer, and consequently exhibits essentially no catalytic activity for polymerization of an alpha-olefin monomer. Here, when referring to catalytic activity during a polymerization reaction, reference is with respect to the catalytic activity of a pre-catalyst, and it is to be understood that the pre-catalyst functions in concert with at least one co-catalyst for effecting catalytic polymerization of an alpha-olefin monomer.

In some embodiments, as described herein, the pre-catalyst comprises labile groups and activation of the pre-catalyst is effected by removing at least one of the labile groups.

In some embodiments, the pre-catalyst is any of the pre-catalysts described herein.

The term "co-catalyst", which is also referred to herein and in the art, interchangeably, as "activator" is defined to be any compound which can activate any one of the pre-catalyst compounds described herein by converting the neutral pre-catalyst compound to a catalytically active catalyst compound cation. Non-limiting activators, for example, include alumoxanes, aluminum alkyls, ionizing activators, which may be neutral or ionic, and conventional-type cocatalysts. Preferred activators typically include alumoxane compounds (such as methyl alumoxane; MAO), modified alumoxane compounds, and ionizing anion precursor compounds that abstract a reactive, σ-bound, metal ligand making the metal complex cationic and providing a charge-balancing noncoordinating or weakly coordinating anion.

In one embodiment, alumoxane activators are utilized as an activator in the catalyst composition. Examples of useful alumoxanes include, but are not limited to, methylalumoxane (MAO), modified methylalumoxane (MMAO), ethylalumoxane and isobutylalumoxane. When the activator is an alumoxane (modified or unmodified), some embodiments select the maximum amount of activator at a 5000-fold molar excess Al/M over the catalyst compound (per metal catalytic site). The minimum activator-to-catalyst-compound is a 1:1 molar ratio. Alternate preferred ranges include from 1:1 to 1:10000, or from m1:1 to 1:1000, or from 1:1 to 500:1, alternately from 1:1 to 200:1, alternately from 1:1 to 100:1, or alternately from 1:1 to 50:1.

Non-coordinating anions may also be used as co-catalysts herein. The term "non-coordinating anion" or "NCA" (also referred to as a "non-coordinating anion activator," or "NCAA") means an anion which either does not coordinate to a cation or which is only weakly coordinated to a cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Noncoordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) tetrakis (pentafluorophenyl) borate, a tris perfluorophenyl boron metalloid precursor, or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium, indium, or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof; preferred are alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. A preferred neutral stoichiometric activator is tris perfluorophenyl boron or tris perfluoronaphthyl boron. In some embodiments, a catalyst system as described herein comprises a pre-catalyst represented by Formula II as described herein and a co-catalyst as described herein.

In some embodiments, a catalyst system as described herein comprises a pre-catalyst represented by Formula II as described herein and a co-catalyst which is an alumoxane, such as methylalumoxane.

In some embodiments, a catalyst system as described herein comprises a pre-catalyst represented by Formula II as described herein and a co-catalyst which comprises which is an alumoxane, such as methylalumoxane, in combination with any of the other co-catalysts as described herein (e.g., a NCA).

Polymerization of Alpha-Olefins:

According to an aspect of some embodiments of the present invention there is provided a process of polymerizing an alpha-olefin, the process comprising contacting the alpha-olefin with a catalyst system, as defined herein.

In some embodiments, the process is effected by contacting the alpha-olefin with a catalyst system which comprises:

(i) a pre-catalyst comprising a group 4 element being in coordination with a Salan ligand, said Salan ligand having a non-symmetric (non-palindromic) sequential diamino-containing skeleton unit as described herein; and (ii) a co-catalyst, as described herein.

While some embodiments of invention relate to a pre-catalyst having general Formula II as above, it is to be noted that pre-catalysts having other Salan ligands, and which are devoid of a symmetry element are also contemplated. Pre-catalysts having other Salan ligands, and which exhibit a fac-mer wrapping mode around the group 4 element are also contemplated. In some embodiments, the co-catalyst is methylaluminoxane.

As discussed hereinabove, catalyst systems which comprise a pre-catalyst as disclosed herein, were shown to be active in polymerization of versatile alpha-olefins. The term "alpha-olefin" is used herein to generally describe unsaturated compounds having a terminal double bond, namely, on the alpha carbon, which can be represented, for example, as $H_2C=CRaRb$, wherein Ra and Rb can each independently be hydrogen, alkyl, alkenyl, cycloalkyl and aryl, as defined herein, or a saturated or unsaturated, substituted or unsubstituted hydrocarbon chain being 1-30 carbon atoms in length, including, but not limited to, methyl, ethyl, propyl, butyl, pentyl, heptyl, octyl, nonyl, decyl, undecyl, dodecyl, and substituted analogs thereof. In some embodiments, Ra is hydrogen and Rb is hydrogen, alkyl, alkenyl, cycloalkyl and aryl, as defined herein, or a saturated or unsaturated, substituted or unsubstituted hydrocarbon chain, as defined herein. Suitable substituents on the hydrocarbon chain include, without limitation, alkyl, cycloalkyl, as well as hydroxy, ether, keto, aldehyde, and halogen functionalities.

This term is used herein in the context of monomers used in the polymerization processes described herein, and is referred to herein interchangeably also as "alpha-olefin monomer" or simply as "monomer". For purposes of this invention and the claims thereto, ethylene is considered an alpha-olefin.

Exemplary alpha-olefin monomers that can be utilized include, but are not limited to, ethylene, propylene, 1-butene, 1-pentene, 1-hexene, vinyl-cyclohexane, 4-methyl-1-pentene, 1,5-hexadiene, 1-heptene, 1-octene, 1-nonene, 1-decene, 1-undecene, 1-dodecene, as well as higher olefins (containing more than 10 carbon atoms and being branched or unbranched) and aromatic olefins such as styrene.

Mixtures of alpha-olefins, such as, but not limited to, the alpha-olefins described herein, can be utilized in the process described herein, so as to produce co-polymers.

The term "polymerization" therefore encompasses both "homo-polymerization" and "co-polymerization".

In an exemplary embodiment, the olefin monomers comprise a mixture of propylene, and an additional alpha-olefin such as ethylene or an alpha-olefin of 4-12 carbon atoms in length (such as butene, pentene, heptene, octene, nonene, decene, undecene, dodecene, and mixtures thereof).

In an exemplary embodiment, the alpha-olefin monomer consists of propylene (without comonomer, e.g., comonomer is present at 0 wt %).

In some embodiments, the alpha-olefin is propylene.

In some embodiments, the process is utilized for producing tacticity-controlled polymerization of alpha-olefins.

Thus, by selecting a suitable pre-catalyst, highly stereoregular (e.g., highly isotactic) polymers can be produced, if so desired. Alternatively, the pre-catalyst of choice is such that produces less steroregular polymers, if so desired.

Similarly, the molecular weight of the polymer can be influenced by virtue of the pre-catalyst used.

The control on the polymer's characteristics can be made by virtue of either the Salan ligand precursor, the metal M and/or the labile groups X, guidelines for which are exemplified in the Examples section that follows.

By "contacting" it is meant bringing the pre-catalyst, the co-catalyst and the olefin in such proximity that enables electronic interactions between the metal and the olefin.

The reactants (including the alpha-olefin, the pre-catalyst, the co-catalyst, an optional solvent, and any optional scavengers) are typically combined in a reaction vessel at a temperature of 0° C. to 200° C. (or 20° C. to 160° C., or 20° C. to 100° C., or at room temperature) and a pressure of 0 MPa to 1000 MPa for a residence time as described herein.

In some embodiments, where the olefin is a gaseous olefin, the olefin pressure is typically greater than 5 psig (34.5 kPa); or, greater than 10 psig (68.9 kPa); or, greater than 45 psig (310 kPa). When a diluent is used with the gaseous olefin, the aforementioned pressure ranges may also be suitably employed as the total pressure of olefin and diluent. Likewise, when a liquid olefin is employed and the process is conducted under an inert gaseous atmosphere, then the aforementioned pressure ranges may be suitably employed for the inert gas pressure.

The quantity of the pre-catalyst that is employed in the herein described process is any quantity that provides for an operable polymerization reaction. In some embodiments, the ratio of moles of alpha-olefin monomers to moles of the pre-catalyst is greater than 10:1; or greater than 100:1; or greater than 1000:1; or greater than 10,000:1; or greater than 25,000:1; or greater than 50,000:1; or greater than 100,000:1.

In some embodiments, 0.00001 to 1.0 moles, or 0.0001 to 0.05 moles, or 0.0005 to 0.01 moles of pre-catalyst are charged to the reactor per mole of alpha-olefin or a mixture of alpha-olefins charged.

In some embodiments, the process is effected in the presence of a solvent, and the contacting encompasses contacting the indicated components (e.g., pre-catalyst, co-catalyst and alpha-olefin) and the solvent.

The process can be regarded as a solution process, although it may be a bulk or high pressure process.

In some embodiments, the process if a homogeneous processes (A homogeneous process is defined to be a process where at least 90 wt % of the product is soluble in the reaction media.)

In some embodiments, the process is a bulk homogeneous process (A bulk process is defined to be a process where reactant concentration in all feeds to the reactor is 70 volume % or more).

In another embodiment, the process is a slurry process. As used herein the term "slurry process" or "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

The process may be batch, semi-batch, or continuous. As used herein, the term continuous means a system that operates without interruption or cessation. For example, a continuous process to produce a polymer would be one where the reactants are continually introduced into one or more reactors and polymer product is continually withdrawn.

In some embodiments, the process is effected without a solvent, and is thus a solvent-less process. In some of these embodiments, the alpha-olefin is in a liquid form. Alpha-olefins suitable for use in such embodiments include any alpha-olefin that is liquid at the temperature at which the polymerization reaction is performed. Exemplary alpha-olefins that are liquid at room temperature include, but are not limited to, 1-pentene, 1-hexene, 1-octene, vinylcyclohexane, 1,5-hexadiene and styrene. Other such alpha-olefins are recognizable by any person skilled in the art.

In some embodiments, contacting is effected by placing the alpha-olefin, the pre-catalyst and the co-catalyst in a chemical reactor, with or without a solvent.

Contacting the catalyst system and the alpha-olefin monomers can be effected simply by adding to a reactor the pre-catalyst, the co-catalyst, the monomer and optionally a solvent.

Alternatively, the pre-catalyst may be formed in situ by placing in the reactor a ligand precursor (Salan ligand precursor as described herein), prior to the formation of a complex with the metal), and a suitable metallic reagent (such as $MX_{n+2}$, as described herein), which form together the metal complex.

The contacting can thus be effected by placing in the reactor a Salan ligand precursor, a metallic reagent, the co-catalyst and the alpha-olefin.

Suitable metallic reagents include, but are not limited to, tetrachlorotitanium, tetrabenzyltitanium, tetrakis(dimethylamido)titanium, tetra(iso-propoxy)titanium as well as related complexes of titanium, or related complexes of the other group 4 metals, with or without additional reagents (e.g., a base such as triethylamine).

This in situ pre-catalyst may be activated by the addition of a co-catalyst to afford an active polymerization catalyst, without the previous isolation of the pre-catalyst.

Optionally, contacting is further effected by mixing (e.g., by mechanical or magnetic stirring, shaking, etc.) the alpha-olefin, the pre-catalyst (or the Salan ligand precursor and the metallic reagent) and the co-catalyst, and optionally the solvent.

The chemical reactor can be, for example, a continuous flow chemical reactor, a batch or semi-batch chemical reactor, and a plug-flow chemical reactor, where the size of the chemical reactor can range from a micro-scale laboratory chemical reactor, through a product/process development scale chemical reactor, and up to a large scale commercial chemical reactor.

In some embodiments, the process is effected by placing an alpha-olefin in a liquid form, a pre-catalyst as described herein and a co-catalyst in a chemical reactor, and mixing the components, as described herein. Optionally, an organic solvent is also placed in the reactor.

Suitable organic solvents include, but are not limited to, any non-protic organic solvent which is capable of suspending or dissolving, without decomposing, the pre-catalyst described herein. Examples include, without limitation, alkanes such as pentane, heptane, hexane, dichloromethane and petroleum ether, and aromatic solvents such as benzene, toluene, and chlorobenzene.

In some embodiments, the process is effected while utilizing an alpha-olefin in a gaseous form. Alpha-olefins suitable for use in these embodiments are propylene, ethylene, and 1-butene, or any other alpha-olefin that is gaseous under the polymerization conditions.

In some embodiments, the process is effected by placing a pre-catalyst, a co-catalyst and a solvent, as described herein, in the chemical reactor and charging the reactor with the gaseous alpha-olefin.

In these embodiments, the gaseous alpha-olefin can be flowed into the reactor continuously, batch-wise or in one batch at the beginning of the process. Monitoring the pressure in the reactor can be performed during the process. In some embodiments, the polymerization process proceeds while maintaining a certain pressure in the chemical reactor (e.g., while purging some of the gas during the process and/or by continuously or batch-wise flowing gaseous alpha-olefin to the reactor). Alternatively, the polymerization process is effected by introducing a gaseous alpha-olefin up to a certain pressure, without further controlling the reaction pressure.

In some embodiments, the polymerization is effected at a pressure that ranges from 1 bar to 20 bars, although higher pressures are also contemplated.

In these embodiments, the solvent is optionally selected such that the alpha-olefin is dissolvable therein. Suitable solvents are as described hereinabove.

The above described reactants can be placed in the reactor in any order. In some embodiments, the alpha-olefin or a solution containing same is first added, the pre-catalyst or the Salan ligand precursor and the metallic reagent are added to the solution and the co-catalyst in then added, optionally in a solution together with the alpha-olefin, with or without a solvent. Optionally, when the alpha-olefin is in a gaseous form, the pre-catalyst or the Salan ligand precursor and the metallic reagent are added to a solvent, the gaseous alpha-olefin is introduced to the reactor and the reactor is then sealed, and then the co-catalyst is injected into the sealed reactor.

In some embodiments, the polymerization process is effected at a temperature within a range of from 0° C. to above ambient temperature, for example, at 50° C., 60° C., 70° C. and even higher temperatures. In some embodiments, the process is effected at ambient temperature (e.g., room temperature). The process can be effected within a range of temperatures, for example, at a temperature range of 0-5° C., 5-10° C., 0-10° C., 10-15° C., 10-20° C., 20-25° C., 20-30° C., 25-30° C., 30-40° C., 40-50° C., 50-60° C. or 60-70° C. Any temperature or temperature range between 0° C. and 200° C. are contemplated.

The reaction temperature can be controlled as desired, by cooling, chilling or heating the reactor or the components added to the reactor (e.g., the alpha-olefin, a solution containing the pre-catalysts and/or a solution containing the co-catalyst). In some cases, the process involves exothermic reactions.

In some embodiments, contacting is effected by for a time period that ranges from a few seconds (e.g., 5-10 seconds) to a few hours (e.g., 2-24 hours), and may also last for several days (e.g., 2-7 days).

In some embodiments, polymerization is effected for a time period of from 1 minute to 24 hours.

In some embodiments, the polymerization reaction is terminated by adding an external quencher such as a protic solvent (e.g., methanol), or by otherwise deactivating the active catalyst. Optionally, the process terminates once the alpha-olefin is completely consumed.

Once the process terminates, the formed polymer can be isolated from the reaction mixture. Isolating the polymer can be performed by routine work-up, using methods well-recognized by any person skilled in the art.

Analyzing physicochemical properties and characteristics of the poly(alpha-olefin) products produced by the process can thereafter be effected by various techniques, such as melting point, spectroscopy such as NMR, X-ray crystallography, mechanical strength such as elasticity measurements, etc. Structural information and molecular weight information relating to polymer molecular weight and molecular weight distribution via the polydispersity index (PDI), are also determined.

Exemplary methodologies for implementing the process as described herein are presented in further detail the Examples section that follows.

In some embodiments, the catalyst system described herein is a homogeneous catalyst system.

As used herein throughout, the term "homogeneous catalyst system", or "homogeneous catalysis", refer to catalytic reactions in which the active catalyst is characterized by a homogeneous catalytic site, namely, each molecule has the same catalytic site, as opposed to heterogeneous catalyses, which are characterized by variable catalytic sites.

It is to be noted that the terms "homogeneous" and "heterogeneous" when used for a catalyst system should not be confused with these terms when used to describe the polymerization process.

According to some embodiments of the present invention, the catalyst system can be such that the co-catalyst, the pre-catalyst and the alpha-olefin are all in the same phase, typically a liquid phase.

As demonstrated herein, the catalyst system described herein performs efficiently as a system, in which at least the pre-catalyst is dissolved in the alpha-olefin or in a solution containing the alpha-olefin.

Optionally, the pre-catalyst and/or the co-catalyst can be adsorbed on a solid support, such as an inert solid support.

The solid support can be, for example, composed of particles onto which the pre-catalyst and/or the co-catalyst are adsorbed. The particles can be, for example, made of silica, magnesia or alumina particles, and can be suspended/dispersed in the reaction medium (the alpha-olefin or a solution containing the same).

In some embodiments, the supported material is a porous support material, for example, talc, and inorganic oxides. Other support materials include zeolites, clays, organoclays, or any other organic or inorganic support material and the like, or mixtures thereof.

In some embodiments, the support material is an inorganic oxide in a finely divided form. Suitable inorganic oxide materials for use in the catalyst systems herein include metal oxides such as silica, alumina and mixtures thereof. Other suitable support materials, however, can be employed.

It is desired that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 µm. More preferably, the surface area of the support material is in the range of from about 50 to about 500 $m^2/g$, pore volume of from about 0.5 to about 3.5 cc/g and average particle size of from about 10 to about 200 µm. Most preferably the surface area of the support material is in the range is from about 100 to about 400 $m^2/g$, pore volume from about 0.8 to about 3.0 cc/g and average particle size is from about 5 to about 100 µm. The average pore size of the support material useful in the invention is in the range of from 10 to 1000 microns, preferably 50 to about 500 microns, and most preferably 75 to about 350 microns. In some embodiments, the support material is a high surface area, amorphous silica (surface area=300 $m^2/gm$; pore volume of 1.65 $cm^3/gm$).

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce the catalyst system of this invention. The calcined support material is then contacted with at least one polymerization catalyst comprising at least one metallocene.

The Polymer:

Various types of homo-polymerization and co-polymerization processes of different types of alpha-olefins can be performed using the catalyst system described herein, under different polymerization conditions.

In some embodiments, the process is utilized for producing tacticity-controlled polymerization of alpha-olefins.

Thus, by selecting a suitable pre-catalyst, highly stereoregular (e.g., highly isotactic) polymers can be produced, if so desired. Alternatively, the pre-catalyst of choice is such that produces less steroregular polymers, if so desired.

Similarly, the molecular weight of the polymer can be controlled by virtue of the pre-catalyst used.

The control on the polymer's characteristics can be made by virtue of either the Salan ligand precursor, the metal M and/or the labile groups X, guidelines for which are exemplified in the Examples section that follows.

The polymer obtained by the process as described herein is referred to herein as a polymer or copolymer of an alpha-olefin or as polyolefin.

"Polyolefin" means an oligomer or polymer of two or more olefin monomer units, with "olefin" being an alpha-olefin as defined herein.

A "polymer" can have two or more of the same or different monomer units. A "homopolymer" is a polymer having monomer units that are the same. A "copolymer" is a polymer having two or more monomer units that are different from each other. A "terpolymer" is a polymer having three monomer units that are different from each other. The term "different" as used to refer to monomer units indicates that the monomer units differ from each other by at least one atom or are different isomerically. Accordingly, the definition of copolymer, as used herein, includes terpolymers and the like.

When a polymer or copolymer is referred to as comprising an olefin, including, but not limited to ethylene, propylene, and butene, the olefin present in such polymer or copolymer is the polymerized form of the olefin.

In some embodiments, a polymer of an alpha-olefin is regarded as having a main backbone chain with no unsaturated bonds (since the double bond at the alpha-beta carbons participates in polymerization. Nonetheless, the polymer or copolymer is referred to as poly(alpha-olefin), as typically used in the art.

For example, when a copolymer is said to have a "propylene" content of 35 wt % to 55 wt %, it is understood that the monomer unit in the copolymer is derived from propylene in the polymerization reaction and said derived units are present at 35 wt % to 55 wt %, based upon the weight of the copolymer.

Additionally, an ethylene polymer or oligomer contains at least 50 mol % of ethylene, a propylene polymer or oligomer contains at least 50 mol % of propylene, a butene polymer or oligomer contains at least 50 mol % of butene, and so on.

A co-polymer as described herein can have any ratio of the different monomer units. Exemplary co-polymers are prepared from various ratios of a mixture of ethylene and of any of the other alpha-olefins described herein. Other combinations are also contemplated.

Mn is number average molecular weight, Mw is weight average molecular weight. Molecular weight distribution (MWD; also referred to as polymer distribution PDI) is defined to be Mw divided by Mn. Unless otherwise noted, all molecular weight units (e.g., Mw, Mn) are grams/mol.

In some embodiments, the processes described herein produces homopolymers and copolymers of alpha-olefins as described herein, having an Mw of from 500 to 500,000 grams/mol (alternately from 1000 to 450,000 grams/mol, alternately from 1500 to 400,000 grams/mol), and an Mw/Mn (or PDI) of from 1 to 6, or from 1.1 to 5, or from 1.1 to 3.

In some embodiments, the polymer or copolymer of the alpha-olefin is characterized by a molecular weight of $M_W$=at least 100,000 grams/mol, or of at least $M_W$=300,000 grams/mol. Polymer (or copolymer) molecular weights as high as $M_W$=1,000,000 and higher are also contemplated.

In some embodiments, the polymer of the alpha-olefin is characterized by a molecular weight distribution (Mw/Mn; or PDI) that ranges from 1 to 6. In some embodiments, the polymer of the alpha-olefin is characterized by a molecular weight distribution (Mw/Mn; or PDI) lower than 6, lower than 5, lower than 4, lower than 3, and even lower than 2 and in some cases lower than 1.6 or even lower.

In some embodiments, the polymer or copolymer produced has a Tm of 100° C. or more, or 110° C. or more, or 115° C. or more, or 120° C. or more, or 125° C. or more, or 130° C. or more. In some embodiments, the alpha-olefin is propylene and the obtained polypropylene is characterized by a melting transition temperature of at least 150° C. and even of at least 160° C. In some embodiments, the obtained polypropylene is characterized by a melting transition temperature of at least 165° C., and even of at least 168° C.

In some embodiments, the obtained polymer or copolymer of the alpha-olefin is characterized by an isotacticity degree of at least 50%.

As noted hereinabove, in some embodiments, the isotacticity degree [mmmm] is higher than 70%, higher than 90% and in some cases even higher than 99%.

The isotacticity degree [mmmm]% can be determined as described herein, by $^{13}$C-NMR.

The above described characteristics of the obtained polymers are in line with most of the industrial requirements of alpha-olefin polymers, and in some cases are superior to the characteristics of currently produced polymers of alpha-olefins.

Further according to embodiments of the present invention, there is provided a polymer (or co-polymer) of an alpha-olefin (or of a mixture of two or more alpha-olefins), as described herein, which is prepared by the process as described herein.

Further according to embodiments of the present invention there is provided a polymer or copolymer of an alpha-olefin, prepared by the process as described herein, which is characterized by an isotacticity degree of at least 50%, at least 70%, at least 90%, at least 95% and even of 99% and higher. In some embodiments, the isotacticity degree is as determined by $^{13}$C-NMR, as described herein.

Further according to embodiments of the present invention there is provided a polymer or copolymer of an alpha-olefin, prepared by the process as described herein, which is characterized by a molecular weight of at least $M_w$=100,000 grams/mol, or of at least $M_w$=300,000 grams/mol, or as described herein.

Further according to embodiments of the present invention there is provided a polymer or co-polymer of an alpha-olefin, prepared by the process as described herein, which is characterized by a molecular weight distribution (PDI) lower than 6, or as described herein.

Further according to embodiments of the present invention there is provided a polymer or co-polymer of an alpha-olefin, prepared by the process as described herein, which is characterized by a high tacticity, as described herein, high molecular weight as described herein and low PDI, as described herein. In some embodiments, the polymer is produced by a process as described herein.

Accordingly, some embodiments of the present invention are of a method of controlling a tacticity, a molecular weight and/or a PDI of a polymer of an alpha-olefin, which is effected by contacting the alpha-olefin with a suitable pre-catalyst according to the guidelines provided herein for a Salan-group 4 metal complex pre-catalysts.

Further according to an aspect of some embodiments of the present invention there is provided a polypropylene characterized by a melting transition temperature of at least 165° C., or of at least 168° C., prepared by the process described hereinabove.

General:

The term "alkyl", as used herein, describes a saturated aliphatic hydrocarbon including straight chain and branched chain groups. In some embodiments, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. In some embodiments, the alkyl is a lower alkyl having 1 to 4 carbon atoms. The alkyl group may be substituted or unsubstituted, as indicated herein.

The term alkenyl, as used herein, describes an alkyl, as defined herein, which contains a carbon-to-carbon double bond.

The term alkynyl, as used herein, describes an alkyl, as defined herein, which contains carbon-to-carbon triple bond.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted, as indicated herein.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted, as indicated herein.

The term "alkoxy" describes both an —O-alkyl and an —O-cycloalkyl group, as defined herein.

The term "aryloxy" describes an —O-aryl, as defined herein.

Each of the alkyl, cycloalkyl and aryl groups in the general formulas herein may be substituted by one or more substituents, whereby each substituent group can independently be, for example, halogen, alkyl, alkoxy, cycloalkyl, alkoxy, nitro, amine, hydroxyl, thiol, thioalkoxy, thiohydroxy, carboxy, amide, aryl and aryloxy, depending on the substituted group and its position in the molecule. Additional substituents are also contemplated.

The term "halide", "halogen" or "halo" describes fluorine, chlorine, bromine or iodine.

The term "haloalkyl" describes an alkyl group as defined herein, further substituted by one or more halide(s).

The term "hydroxyl" or "hydroxy" describes a —OH group.

The term "thiohydroxy" or "thiol" describes a —SH group.

The term "thioalkoxy" describes both an —S-alkyl group, and a —S-cycloalkyl group, as defined herein.

The term "thioaryloxy" describes both an —S-aryl and a —S-heteroaryl group, as defined herein.

The term "amine" describes a —NR'R" group, with R' and R" as described herein.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

The term "heteroalicyclic" or "heterocyclyl" describes a monocyclic or fused ring group having in the ring(s) one or more atoms such as nitrogen, oxygen and sulfur. The rings may also have one or more double bonds. However, the rings do not have a completely conjugated pi-electron system. Representative examples are piperidine, piperazine, tetrahydrofurane, tetrahydropyrane, morpholino and the like.

The term "carboxy" or "carboxylate" describes a —C(=O)—OR' group, where R' is hydrogen, alkyl, cycloalkyl, alkenyl, aryl, heteroaryl (bonded through a ring carbon) or heteroalicyclic (bonded through a ring carbon) as defined herein.

The term "carbonyl" describes a —C(=O)—R' group, where R' is as defined hereinabove.

The above-terms also encompass thio-derivatived thereof (thiocarboxy and thiocarbonyl).

The term "thiocarbonyl" describes a —C(=S)—R' group, where R' is as defined hereinabove.

A "thiocarboxy" group describes a —C(=S)—OR' group, where R' is as defined herein.

A "sulfinyl" group describes an —S(=O)—R' group, where R' is as defined herein.

A "sulfonyl" group describes an —S(=O)$_2$—R' group, where Rx is as defined herein.

A "carbamyl" group describes an —OC(=O)—NR'R" group, where R' is as defined herein and R" is as defined for R'.

A "nitro" group refers to a —NO$_2$ group.

A "cyano" or "nitrile" group refers to a —C≡N group.

The term "piperazine" refers to a

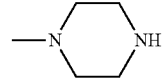

group or a

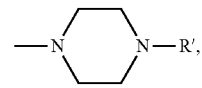

where R' as defined hereinabove. The term "piperidine" refers to a

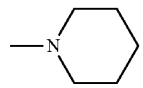

group.

The term "pyrrolidine" refers to a

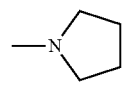

group.

The term "pyridine" refers to a

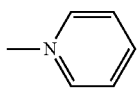

group.

The term "morpholine" refers to a

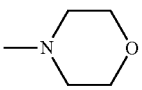

group, and encompasses also thiomorpholine.

The term "thiomorpholine" refers to a

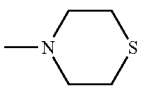

group.

The term "hexahydroazepine" refers to a

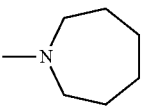

group.

As used herein, the term "azide" refers to a —$N_3$ group.

The term "sulfonamide" refers to a —S(=O)$_2$—NR'R" group, with R' and R" as defined herein.

The term "phosphonyl" describes an —O—P(=O)(OR')$_2$ group, with R' as defined hereinabove.

The term "phosphinyl" describes a —PR'R" group, with R' and R" as defined hereinabove.

A "cyclic ring" encompasses an all-carbon ring structure, such as aryl or cycloalkyl, as defined herein, and further encompasses structures containing more than one ring (e.g., bicyclic structures).

A "heterocyclic ring" encompasses a ring structure that contains one or more heteroatoms such as nitrogen, oxygen, sulfur, and the like, such as heteroalicyclic and heteroaryl, as defined herein, and further encompasses structures containing more than one ring (e.g., bicyclic structures).

When catalysts are described as comprising neutral stable forms of the components, it is well understood by one of ordinary skill in the art, that the ionic form of the component is the form that reacts with the monomers to produce polymers. In the description herein, the transition metal compound used for catalysis may be described as a catalyst precursor, a pre-catalyst compound, a catalyst, or a catalyst compound, and these terms are used interchangeably.

A "reactor" is any container(s) in which a chemical reaction occurs.

"Mol %" means mole percent, "wt %" means weight percent, and "vol %" means volume percent. Room temperature is 25° C. unless otherwise noted.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" or "process" refers to manners, means, techniques and procedures for accomplishing a given task including, but not limited to, those manners, means, techniques and procedures either known to, or readily developed from known manners, means, techniques and procedures by practitioners of the chemical art.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Materials and Experimental Methods

The metal complexes were synthesized and handled under an atmosphere of dry nitrogen in a nitrogen-filled glove box.

Polymerization experiments were performed in designated apparatus with exclusion of air.

All reagents were of analytical grade.

Pentane purchased from J. T. Baker was washed with $HNO_3/H_2SO_4$ prior to distillation from Na/benzophenone/ tetraglyme under argon atmosphere. Diethylether purchased from Gadot was refluxed over Na/benzophenone and distilled under argon atmosphere. Toluene purchased from Bio-Lab was refluxed over Na and distilled under argon atmosphere. Benzene purchased from Loba-Chemie, Methanol purchased from Gadot, and tetrahydrofuran purchased from Bio-Lab were used as received. Benzyl magnesium chloride, salicylaldehyde, 3,5-dichlorosalicylaldehyde, 3,5-dibromosalicylaldehyde, 3,5-diiodosalicylaldehyde, N-Methylethylenediamine, N-benzylethylenediamine, N-isopropylethylenediamine, triethylamine, N-methyl-1,3-propane diamine, 2-aminobenzylamine, 4-chloro-2-methyl-phenol, 1,2,3,4-tetrahydronaphthalene, $TiCl_4$, Ti(IV) isopropoxide, Tetrakis(dimethylamido) titanium, and Zirconium (IV) tert-butoxide, were purchased from Aldrich and used as received. Hafnium (IV) tert-butoxide, and tetrabenzylhafnium were purchased from Strem were used as received. S-(2)-Pyrrolidinemethanamine.2HCl, and 2-Amino-N-methyl-benzenemethanamine.2HCl were purchased from Amatek Chemical and used as received. Formaldehyde (37% in water) was purchased from Gadot and used as received. N-ethylethylenediamine, ethyl chloroformate, bromine, and sodium borohydride were purchased from Fluka and used as received. 3,5-di-tert-butyl-2-hydroxybenzaldehyde was purchased from Appolo and used as received. Tris(pentafluorophenyl)borane was obtained from Strem Chemicals and used as received. Solid Methylaluminoxane (MAO) was obtained by solvent removal from a 10 wt % solution in toluene purchased from Aldrich.

1-Hexene purchased from Aldrich, and styrene purchased from Fluka, were passed through alumina prior to use. Polymerization grade propylene (99.5%) purchased from Maxima, and ethylene (99.5%) purchased from Gas-Ron, were passed through molecular sieves prior to use. 1-Butene (99.95%) was purchased from Maxima and used as received.

Tetrabenzyltitanium and tetrabenzylzirconium were synthesized according to a published procedure [U. Zucchini, et al., *J. Organomet. Chem.* 1971, 26, 357-372], and the titanium complex was used shortly after preparation.

2-(1-adamantyl)-4-methylphenol (Arredondo, et. al., *Synth. Commun.* 1996, 26, 3885), 3-Adamantyl-2-hydroxy-5-methylbenzaldehyde, 3-trityl-2-hydroxy-5-methylbenzaldehyde, 3,5-cumyl-2-hydroxybenzaldehyde [K. P. Bryliakov, et. al., *Eur. J. Org. Chem.* 2008, 3369-3376], 2-((methylamino)ethylimino)methyl)-4,6-di-tert-butylphenol [Yeori et al. *Inorg. Chem. Commun.* 2004, 7, 280-282], 2-(bromomethyl)-4,6-dichlorophenol [Gendler et al., *J. Am. Chem. Soc.* 2008, 130, 2144-2145], 2-(bromomethyl)-4-adamantyl-6-methyl-phenol, 2-(bromomethyl)-4-trityl-6-methyl-phenol, 2-(bromomethyl)-4,6-tert-butyl-phenol [Cohen et al., *Organometallics* 2009, 28, 1391-1405], and 2-(bromomethyl)-4,6-diiodophenol [Cohen et al., *Macromolecules* 2010, 43, 1689-1691] were synthesized according to published procedures.

NMR data for the intermediate organic compounds, ligand precursors, titanium complexes, and poly(1-hexene) samples were recorded on a Bruker AC-400 spectrometer. $C_6D_6$ was employed as solvent for the group 4 metal complexes for $^1H$ NMR and $^{13}C$ NMR analyses (impurities in benzene-$d_6$ at δ 7.15 and $^{13}C$ chemical shift of benzene at δ 128.70 were used as reference). $CDCl_3$ was used as solvent for the other samples (chemical shift of TMS at δ=0.00, and $^{13}C$ NMR chemical shift of the solvent at 6=77.16 were used as reference).

$^{13}C$ NMR spectra were collected at 150° C. in a 5 mm probe using a BrukerDRx 500 MHz spectrometer with a $^1H$ frequency of 500 MHz. A 30 degree pulse (Acq=0.52, D1=1 sec) and a relaxation delay of 1 sec was employed to give a digital resolution of 0.1 Hz with continuous broadband proton decoupling (Waltz16). The spectra were acquired using time averaging to provide a signal to noise level adequate to measure the signals/satellites of interest. 20 mg of each sample were dissolved in 0.5 mL of ortho-dichlorobenzene-$d_4$ prior to being inserted into the spectrometer magnet. Prior to data analysis spectra were referenced by setting the chemical shift of the (—CH—)n signal to 21.85 ppm.

Polymers' molecular weights and molecular mass distribution were measured by gel permeation chromatography (GPC) at 135° C. by a Waters GPCV 2000 instrument equipped with refractive index and viscometer detectors, using a set of four PSS columns: $10^6$, $10^5$, $10^4$, $10^3$ Å pore size with 10 µm particle size. o-Dichlorobenzene was the carrier solvent used with a flow rate of 1.0 mL $min^{-1}$. A calibration curve was established with polystyrene standards.

Differential scanning calorimetry analysis was performed on a TA 2920 DSC (TA Instruments). Melting transitions were determined on the second heating run at 10° C./minute with a nitrogen purge at a flow rate of 40 mL $s^{-1}$. The instrument was calibrated for temperature and enthalpy by high purity indium (156.60° C., 28.45 J $g^{-1}$) standard. The following heat-cool-heat cycle was employed: initial temperature 40° C., heat at a rate of 10° C./minute to 200° C., equilibrate at 195° C., cool at a rate of 10° C./minute to 50° C., equilibrate at 50° C., heat at a rate of 10° C./minute to 200° C. The melting temperature was defined as the extremum endothermic peak in the second heat run.

X-ray diffraction measurements for complexes [Ti(Lig$^8$)(O-i-Pr)$_2$], and [Zr(Lig$^{30}$)(O-t-Bu)$_2$], were performed on a Nonius Kappa CCD diffractometer system, using MoKα (λ=0.7107 Å) radiation. The analyzed crystals grown from chilled solutions at −35° C. were embedded within a drop of viscous oil and freeze-cooled to about 110 K. The structures were solved by a combination of direct methods and Fourier techniques using SIR-97 software, and were refined by full-matrix least squares with SHELXL-97.

Elemental analyses were performed in the microanalytical laboratory in the Hebrew University of Jerusalem.

Example 1

Salan Ligand Precursors

A novel family of Salan ligand precursors was prepared. The ligand precursors were designed so as to include a sequential diamino-containing skeleton unit which is non-symmetric, or non-palendromic, as defined herein. In some embodiments, the ligand precursors are designed such that their preferred wrapping mode around octahedral metal centers is fac-mer. In some embodiments, the ligand precursors are designed so as to possess a skeleton which, when wrapped around a center of a group 4 element, results in a metal complex which is devoid of, or lacks, a symmetry element, as defined herein. The non-symmetry (or non-palindromy) in the Salan skeleton is achieved, for example, by employing at least one secondary amine donor (N-H) group and/or by a 3-carbon bridge between the two amine donors, in which two carbon atoms are a part of an aromatic ring system.

Without being bound by any particular theory, it is assumed that the non-symmetry in the Salan ligand skeleton renders the ligand capable of exhibiting a fac-mer wrapping mode around a metal center.

The ligand precursors were designed to include a broad variety of structural modifications that lead to variation of the structures of catalyst systems containing same, and thereby may influence the catalytic activity of these catalyst systems, for example, by means of influencing the properties of polymers produced by catalytic polymerization.

None of the Salan ligand precursors described in the following has ever been described heretofore.

In a search for straightforward, high-yielding, synthetic pathways for preparing such a broad variety of Salan ligand precursors, the present inventors have conceived synthetic pathways that employ readily available starting materials, and involve a minimal number of steps and diminished formation of impurities that may hamper catalyst performance and require tedious purification steps.

The synthetic pathways involve a short synthetic pathway (e.g., minimum number of steps) for obtaining the diamine central building block, which may include a condensation reaction with a carbonyl functionality of the appropriately substituted phenol (e.g., a substituted salicyladehyde), a nucleophilic attack on the halo-methyl derivative (bromo-methyl being accessible and performing satisfactorily) of an appropriately substituted second phenol, and a reduction of the imine group(s). Other synthetic pathways were employed for specific ligands as outlined below. The starting materials used are either commercially available or easily synthesized.

It is noteworthy that, in comparison to common synthetic pathways published in the art, the synthetic pathways presented herein circumvent the application of protecting groups and their removal. Use of expensive metal-mediated cross-coupling reactions is also circumvented. Nonetheless, other synthetic methodologies, such as, for example, those described in the art for preparing Salan ligand precursors, are also contemplated and can be used for preparing the Salan ligand precursors described herein, by selecting suitable reagents (e.g., starting materials). Such a selection should be recognized by any person skilled in the art.

Using the above-described general synthetic pathways, various Salan ligand precursors were synthesized. The following describes in more detail general and exemplary procedures of preparing Salan ligands of several subfamilies, categorized either by the nature of the diamino skeleton (and the bridging moiety) and/or by the nature of the substituent(s) on one or both of the phenol rings.

I. Syntheses of Ligand Precursors from a Methylamino-ethylamine Skeleton:

A general synthetic pathway of preparing Salan ligand precursors from a methylaminoethylamine-based skeleton is presented in Scheme 1 below.

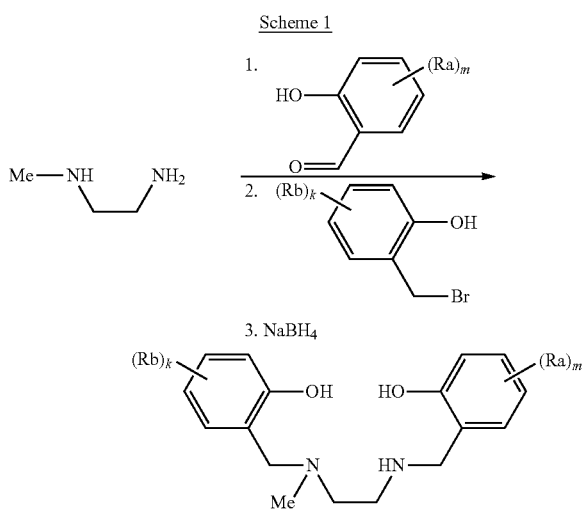

Scheme 1

N-Methylethylenediamine (1 molequivalent) is added to a solution of a substituted 2-hydroxy-benzaldehyde in an organic non-polar solvent (e.g., benzene) and the reaction mixture is refluxed for 2 hours. The solvent is thereafter removed under vacuum, yielding a solid residue (about 100% yield). The obtained substituted 2-((methylamino)ethylimino)methyl)phenol is dissolved in THF, a base (e.g., triethylamine) is added, followed by dropwise addition of a solution of a substituted 2-(bromomethyl)phenol (1 molequivalent) in THF. The reaction mixture is stirred for several (e.g., two) hours. The formed solid is thereafter filtered out and the solvent is removed under vacuum. The intermediate product is dissolved in methanol and reacted with 5 molequivalents of NaBH$_4$ (or any other reducing agent) for several (e.g., 5) hours. The solvent is removed under vacuum, and 50 mL of water are added to destroy the traces of NaBH$_4$. The final product is extracted with dichloromethane, dried with MgSO$_4$, filtered and dried in vacuum, yielding the respective ligand precursor as a white solid, typically in high to quantitative yields. Typically, no further purification steps are required.

In a typical general procedure, ligand precursors having the following general Formula Ia:

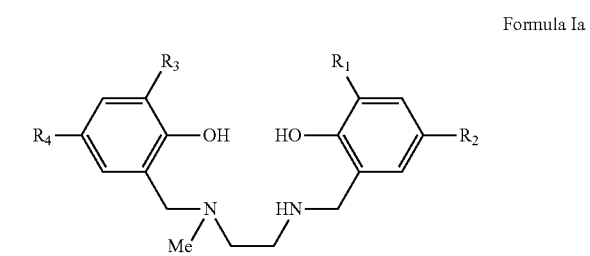

Formula Ia were prepared according to the general procedure described hereinabove, such that in Scheme 1, each of "k"

and "m" is 2; Ra denotes the substituents $R_1$ and $R_2$; and Rb denotes the substituents $R_3$ and $R_4$, as described herein for Formula I.

Formula 1a corresponds to Formula I as described herein, in which $R_5=R_6=R_7=R_8=H$; $Z=Y=CH_2$; R'=H and R=methyl, and $R_1$-$R_4$ are various combinations of substituents, as described hereinabove.

Using the above-described general procedure (see, Scheme 1), exemplary Salan ligand precursors having Formula IB, which are referred to herein as $Lig^{1-12}H_2$, were prepared, as representative ligand precursors having a (N-methylamino)ethylamino bridging unit. These exemplary ligands are characterized by one or more bulky groups and/or electron-withdrawing substituents (halo-substituents) on either or both the phenol proximal to the secondary (N-H) amine nitrogen (e.g., $R_1$ and $R_2$ in the above general Formula 1a) and the other phenol arm (e.g., $R_3$ and $R_4$ in the above general Formula 1a).

The chemical structures of $Lig^1H_2$-$Lig^{12}H_2$ are presented in FIG. 1A.

The structures of all intermediates and final products were verified by NMR measurements.

The following describes in detail the procedures used for preparing exemplary such ligand precursors.

Preparation of $Lig^1H_2$ (see, FIG. 1A and Formula I, wherein $R_1=R_2=R_3=R_4$=t-Bu; $R_5=R_6=R_7=R_8=H$; $Z=Y=CH_2$; R'=H; and R=methyl):

A solution of 2-(bromomethyl)-4,6-di-tert-butylphenol (0.51 gram, 1.7 mmol) in THF (20 mL) was added dropwise to a solution of 2-((methylamino)ethylimino)methyl)-4,6-di-tert-butylphenol (0.49 gram, 1.7 mmol) and triethylamine (3 mL) in THF (20 mL) and stirred for 2 hours. The solid that formed was filtered out and the solvent was removed under vacuum. The intermediate product was dissolved in methanol and cooled in a water bath. Approximately 0.5 gram (5 molequivalents) of $NaBH_4$ was added by small portions and the reaction mixture was stirred for 5 hours at room temperature. The solvent was removed under vacuum and 50 mL of water was added. The final product was extracted with 3 portions (50 mL) of dichloromethane, dried on $MgSO_4$, filtered and dried under vacuum. Yield 0.76 gram (88%).

$^1$H NMR ($CDCl_3$, 400 MHz): δ=7.22 (d, 1H, J=2.5 Hz ArH), 7.20 (d, 1H, J=2.5 Hz ArH), 6.82 (d, 1H, J=2.5 Hz ArH), 6.80 (d, 1H, J=2.5 Hz ArH), 3.91 (s, 2H, $CH_2$), 3.69 (s, 2H, $CH_2$), 2.83 (t, 2H, J=7.5 Hz, $NCH_2$), 2.63 (t, 2H, J=7.5 Hz, $NCH_2$), 2.33 (s, 3H, $NCH_3$), 1.40 (s, 9H, $CH_3$), 1.38 (s, 9H, $CH_3$), 1.28 (s, 9H, $CH_3$), 1.27 (s, 9H, $CH_3$) ppm.

$^{13}$C NMR ($CDCl_3$, 100.67 MHz): δ=154.7 (CO), 154.3 (CO), 140.9 (C), 140.6 (C), 135.9 (C), 135.7 (C), 123.4 (CH), 123.3 (CH), 123.1 (CH), 123.0 (CH), 121.8 (C), 121.2 (C), 62.8 ($CH_2$), 56.0 ($CH_2$), 53.4 ($CH_2$), 45.8 ($CH_2$), 41.9 ($NCH_3$), 35.2 (C), 35.1 (C), 34.3 (C), 34.2 (C), 32.0 ($CH_3$), 31.8 ($CH_3$), 29.7 ($CH_3$), 29.6 ($CH_3$) ppm.

Preparation of $Lig^2H_2$ (see, FIG. 1A and Formula I, wherein $R_1=R_2=R_3=R_4$=Cl; $R_5=R_6=R_7=R_8=H$; $Z=Y=CH_2$; R'=H; and R=methyl):

A solution of 2-(bromomethyl)-4,6-dichlorophenol (0.77 gram, 3.0 mmol) in THF (20 mL) was added dropwise to a solution of 2-((methylamino)ethylimino)methyl)-4,6-dichlorophenol (0.75 gram, 3.0 mmol) and triethylamine (3 mL) in THF (20 mL) and the reaction mixture was stirred for 2 hours. The solid that formed was filtered out and the solvent was removed under vacuum. The intermediate product was dissolved in methanol and cooled in a water bath. Approximately 0.5 gram (5 molequivalents) of $NaBH_4$ was added by small portions and the reaction mixture was stirred for 5 hours at room temperature. The solvent was removed under vacuum and 50 mL of water was added. The final product was extracted with 3 portions (50 mL) of dichloromethane, dried on $MgSO_4$, filtered and dried under vacuum. Yield 1.14 gram (89%).

$^1$H NMR ($CDCl_3$, 400 MHz): δ=7.28 (d, 1H, J=2.4 Hz ArH), 7.26 (d, 1H, J=2.4 Hz ArH), 6.89 (d, 1H, J=2.4 Hz ArH), 6.87 (d, 1H, J=2.4 Hz ArH), 3.96 (s, 2H, $CH_2$), 3.70 (s, 2H, $CH_2$), 2.84 (t, 2H, J=6.3 Hz, $NCH_2$), 2.68 (t, 2H, J=6.3 Hz, $NCH_2$), 2.33 (s, 3H, $NCH_3$) ppm.

$^{13}$C NMR ($CDCl_3$, 100.67 MHz): δ=153.3 (CO), 152.6 (CO), 144.8 (C), 143.2 (C), 129.7 (CH), 129.5 (CH), 127.5 (CH), 127.4 (CH), 124.7 (C), 124.5 (C), 124.4 (C), 124.3 (C), 61.8 ($CH_2$), 56.5 ($CH_2$), 52.7 ($CH_2$), 46.0 ($CH_2$), 42.4 ($NCH_3$) ppm.

Preparation of $Lig^3H_2$ (see, FIG. 1A and Formula I, wherein $R_1=R_2=R_3=R_4$=I; $R_5=R_6=R_7=R_8=H$; $Z=Y=CH_2$; R'=H; and R=methyl):

A solution of 2-(bromomethyl)-4,6-diiodophenol (1.02 gram, 2.3 mmol) in THF (20 mL) was added dropwise to a solution of 2-((methylamino)ethylimino)methyl)-4,6-diiodophenol (1.00 gram, 2.3 mmol) and triethylamine (3 mL) in THF (20 mL) and the reaction mixture was stirred for 2 hours. The solid that formed was filtered out and the solvent was removed under vacuum. 0.5 gram of the intermediate product was dissolved in methanol and cooled on water bath. Approximately 0.2 gram (5 molequivalents) of $NaBH_4$ was added by small portions and the reaction mixture was stirred for 5 hours at room temperature. The solvent was removed under vacuum and 50 mL of water was added. The final product was extracted with 3 portions (50 mL) of dichloromethane, dried on $MgSO_4$, filtered and dried under vacuum. Yield 0.38 gram (76%).

$^1$H NMR ($CDCl_3$, 400 MHz): δ=7.92 (d, 1H, J=1.3 Hz, ArH), 7.90 (d, 1H, J=1.3 Hz, ArH), 7.23 (d, 1H, J=1.3 Hz, ArH), 7.22 (d, 1H, J=1.3 Hz, ArH), 3.89 (s, 2H, $CH_2$), 3.64 (s, 2H, $CH_2$), 2.79 (t, 2H, J=5.9 Hz, $NCH_2$), 2.62 (t, 2H, J=5.9 Hz, $NCH_2$), 2.32 (s, 3H, $NCH_3$) ppm.

Preparation of $Lig^4H_2$ (see, FIG. 1A and Formula I, wherein $R_1=R_2$=t-Bu; $R_3=R_4$=Cl; $R_5=R_6=R_7=R_8=H$; $Z=Y=CH_2$; R'=H; and R=methyl):

A solution of 2-(bromomethyl)-4,6-dichlorophenol (0.44 gram, 1.7 mmol) in THF (20 mL) was added dropwise to a solution of 2-((methylamino)ethylimino)methyl)-4,6-di-tert-butylphenol (0.50 gram, 1.7 mmol) and triethylamine (3 mL) in THF (20 mL) and the reaction mixture was stirred for 2 hours. The solid that formed was filtered out and the solvent was removed under vacuum. The intermediate product was dissolved in methanol and cooled on water bath. Approximately 0.5 gram of $NaBH_4$ was added in small portions and the reaction mixture was stirred for 5 hours at room temperature. The solvent was removed under vacuum and 50 mL of water was added. The final product was extracted with 3 portions (50 mL) of dichloromethane, dried on $MgSO_4$, filtered and dried under vacuum. Yield 0.77 gram (97%).

$^1$H NMR ($CDCl_3$, 400 MHz): δ=7.27 (d, 1H, J=2.4 Hz ArH), 7.22 (d, 1H, J=2.4 Hz ArH), 6.87 (d, 1H, J=2.4 Hz ArH), 6.84 (d, 1H, J=2.4 Hz ArH), 3.96 (s, 2H, $CH_2$), 3.70 (s, 2H, $CH_2$), 2.88 (t, 2H, J=6.5 Hz, $NCH_2$), 2.67 (t, 2H, J=6.5 Hz, $NCH_2$), 2.33 (s, 3H, $NCH_3$), 1.40 (s, 9H, $CH_3$), 1.28 (s, 9H, $CH_3$) ppm.

$^{13}$C NMR ($CDCl_3$, 100.67 MHz): δ=154.4 (CO), 152.6 (CO), 140.7 (C), 136.0 (C), 128.9 (CH), 126.6 (CH), 123.7 (C), 123.6 (CH), 123.2 (CH), 121.4 (C), 61.2 ($CH_2$), 56.3 ($CH_2$), 53.4 ($CH_2$), 45.5 ($CH_2$), 41.6 ($NCH_3$), 34.9 (C), 34.1 (C), 31.7 ($CH_3$), 29.6 ($CH_3$) ppm.

Preparation of Lig⁵H₂ (see, FIG. 1A and Formula I, wherein R₁=trityl; R₂=methyl; R₃=R₄=I; R₅=R₆=R₇=R₈=H; Z=Y=CH₂; R'=H; and R=methyl):

A solution of 2-(bromomethyl)-4,6-diiodophenol (0.61 gram, 1.4 mmol) in THF (20 mL) was added dropwise to a solution of 2-((methylamino)ethylimino)methyl)-4-methyl-6-tritylphenol (0.61 gram, 1.4 mmol) and triethylamine (3 mL) in THF (20 mL) and the reaction mixture was stirred for 2 hours. The solid that formed was filtered out and the solvent was removed under vacuum. The intermediate product was dissolved in methanol and cooled in a water bath. Approximately 0.5 gram of NaBH₄ was added by small portions and the reaction mixture was stirred for 5 hours at room temperature. The solvent was removed under vacuum and 50 mL of water was added. The final product was extracted with 3 portions (50 mL) of dichloromethane, dried on MgSO₄, filtered and dried under vacuum. Yield 0.89 gram (81%).

$^1$H NMR (CDCl₃, 400 MHz): δ=7.89 (d, 1H, J=1.9 Hz, ArH), 7.19-7.09 (m, 16H, ArH), 6.88 (d, 1H, J=1.5 Hz, ArH), 6.74 (d, 1H, J=1.5 Hz, ArH), 3.87 (s, 2H, CH₂), 3.50 (s, 2H, CH₂), 2.55 (t, 2H, J=6.6 Hz, NCH₂), 2.32 (t, 2H, J=6.6 Hz, NCH₂), 2.16 (s, 3H, NCH₃), 2.12 (s, 3H, ArCH₃) ppm.

Preparation of Lig⁶H₂: (see, FIG. 1A and Formula I, wherein R₁=R₃=adamantyl; R₂=R₄=methyl; R₅=R₆=R₇=R₈=H; Z=Y=CH₂; R'=H; and R=methyl)

A solution of 2-(bromomethyl)-4-methyl-6-adamantylphenol (0.41 gram, 1.2 mmol) in THF (20 mL) was added dropwise to a solution of 2-((methylamino)ethylimino)methyl)-4-methyl-6-adamantylphenol (0.40 g, 1.2 mmol) and triethylamine (3 mL) in THF (20 mL) and the reaction mixture was stirred for 2 hours. The solid that formed was filtered out and the solvent was removed under vacuum. The intermediate product was dissolved in methanol and cooled in a water bath. Approximately 0.5 gram of NaBH₄ was added by small portions and the reaction mixture was stirred for 5 hours at room temperature. The solvent was removed under vacuum and 50 mL of water was added. The final product was extracted with 3 portions (50 mL) of dichloromethane, dried on MgSO₄, filtered and dried under vacuum. Yield 0.46 gram (64%).

Preparation of Lig⁷H₂: (see, FIG. 1A and Formula I, wherein R₁=adamantyl; R₂ methyl; R₃=R₄=Cl; R₅=R₆=R₇=R₈=H; Z=Y=CH₂; R'=H; and R=methyl)

A solution of 2-(bromomethyl)-4,6-dichlorophenol (0.60 gram, 2.4 mmol) in THF (20 mL) was added dropwise to a solution of 2-((methylamino)ethylimino)methyl)-4-methyl-6-adamantylphenol (0.77 gram, 2.4 mmol) and triethylamine (3 mL) in THF (20 mL) and the reaction mixture was stirred for 2 hours. The solid that formed was filtered out and the solvent was removed under vacuum. The intermediate product was dissolved in methanol and cooled in a water bath. Approximately 0.5 gram of NaBH₄ was added by small portions and the reaction mixture was stirred for 5 hours at room temperature. The solvent was removed under vacuum and 50 mL of water was added. The final product was extracted with 3 portions (50 mL) of dichloromethane, dried on MgSO₄, filtered and dried under vacuum. Yield 1.01 gram (83%).

$^1$H NMR (CDCl₃, 400 MHz): δ=7.28 (d, 1H, J=2.4 Hz ArH), 6.94 (d, 1H, J=1.8 Hz ArH), 6.85 (d, 1H, J=2.4 Hz ArH), 6.66 (d, 1H, J=1.8 Hz ArH), 3.93 (s, 2H, CH₂), 3.69 (s, 2H, CH₂), 2.89 (t, 2H, J=6.8 Hz, NCH₂), 2.75 (t, 2H, J=6.8 Hz, NCH₂), 2.31 (s, 3H, NCH₃), 2.23 (s, 3H, ArCH₃), 2.11 (s, 6H, Adamantyl), 2.04 (s, 3H, Adamantyl), 1.76 (s, 6H, Adamantyl) ppm.

$^{13}$C NMR (CDCl₃, 100.67 MHz): δ=155.3 (CO), 153.6 (CO), 137.6 (C), 129.5 (CH), 128.1 (C), 127.7 (CH), 127.4 (CH), 127.1 (CH), 124.5 (C), 122.8 (C), 61.5 (CH₂), 56.7 (CH₂), 53.6 (CH₂), 45.8 (CH₂), 42.3 (NCH₃), 41.1 (CH₂), 37.8 (CH₂), 29.8 (CH), 21.9 (ArCH₃) ppm.

Preparation of Lig⁸H₂ (see, FIG. 1A and Formula I, wherein R₁=adamantyl; R₂=methyl; R₃=R₄=Br; R₅=R₆=R₇=R₈=H; Z=Y=CH₂; R'=H; and R=methyl):

A solution of 2-(bromomethyl)-4,6-dibromophenol (0.80 gram, 2.3 mmol) in THF (20 mL) was added dropwise to a solution of 2-((methylamino)ethylimino)methyl)-4-methyl-6-adamantylphenol (0.76 gram, 2.3 mmol) and triethylamine (3 mL) in THF (20 mL) and the reaction mixture was stirred for 2 hours. The solid that formed was filtered out and the solvent was removed under vacuum. The intermediate product was dissolved in methanol and cooled in a water bath. Approximately 0.5 gram of NaBH₄ was added by small portions and the reaction mixture was stirred for 5 hours at room temperature. The solvent was removed under vacuum and 50 mL of water was added. The final product was extracted with 3 portions (50 mL) of dichloromethane, dried on MgSO₄, filtered and dried under vacuum. Yield 1.07 gram (79%).

$^1$H NMR (CDCl₃, 400 MHz): δ=7.55 (d, 1H, J=2.0 Hz, ArH), 7.02 (d, 1H, J=2.0 Hz, ArH), 6.91 (d, 1H, J=1.4 Hz, ArH), 6.64 (d, 1H, J=1.4 Hz, ArH), 3.91 (s, 2H, CH₂), 3.67 (s, 2H, CH₂), 2.84 (t, 2H, J=6.5 Hz, NCH₂), 2.65 (t, 2H, J=6.5 Hz, NCH₂), 2.30 (s, 3H, NCH₃), 2.22 (s, 3H, ArCH₃), 2.10 (s, 6H, Adamantyl), 2.03 (s, 3H, Adamantyl), 1.75 (s, 6H, Adamantyl) ppm.

Preparation of Lig⁹H₂: (see, FIG. 1A and Formula I, wherein R₁=adamantyl; R₂=methyl; R₃=R₄=I; R₅=R₆=R₇=R₈=H; Z=Y=CH₂; R'=H; and R=methyl)

A solution of 2-(bromomethyl)-4,6-diiodophenol (1.12 gram, 2.5 mmol) in THF (20 mL) was added dropwise to a solution of 2-((methylamino)ethylimino)methyl)-4-methyl-6-adamantylphenol (0.83 gram, 2.5 mmol) and triethylamine (3 mL) in THF (20 mL) and the reaction mixture was stirred for 2 hours. The solid that formed was filtered out and the solvent was removed under vacuum. The intermediate product was dissolved in methanol and cooled in a water bath. Approximately 0.5 gram of NaBH₄ was added by small portions and the reaction mixture was stirred for 5 hours at room temperature. The solvent was removed under vacuum and 50 mL of water was added. The final product was extracted with 3 portions (50 mL) of dichloromethane, dried on MgSO₄, filtered and dried under vacuum. Yield 1.59 gram (93%).

$^1$H NMR (CDCl₃, 400 MHz): δ=7.92 (d, 1H, J=2.0 Hz ArH), 7.21 (d, 1H, J=2.0 Hz ArH), 6.93 (d, 1H, J=1.8 Hz ArH), 6.65 (d, 1H, J=1.8 Hz ArH), 3.92 (s, 2H, CH₂), 3.63 (s, 2H, CH₂), 2.85 (t, 2H, J=6.8 Hz, NCH₂), 2.66 (t, 2H, J=6.8 Hz, NCH₂), 2.30 (s, 3H, NCH₃), 2.24 (s, 3H, ArCH₃), 2.12 (s, 6H, Adamantyl), 2.06 (s, 3H, Adamantyl), 1.77 (s, 6H, Adamantyl) ppm.

$^{13}$C NMR (CDCl₃, 100.67 MHz): δ=157.9 (CO), 155.3 (CO), 146.0 (C), 137.6 (CH), 137.5 (CH), 128.1 (C), 127.8 (CH), 127.5 (CH), 124.5 (C), 122.9 (C), 61.3 (CH₂), 56.7 (CH₂), 53.7 (CH₂), 45.9 (CH₂), 42.2 (NCH₃), 41.1 (CH₂), 37.9 (CH₂), 29.9 (CH), 21.5 (ArCH₃) ppm.

Synthesis of 2-((methylamino)ethylimino)methyl)-3,5-dihalophenol: N-Methylethylenediamine (1.50 gram, 20.2 mmol) was added to a solution of 3,5-dichlorosalicylaldehyde (3.86 grams, 20.2 mmol), for Lig$^{10}$H$_2$, (or to an equimolar amount of 3,5-dibromosalicylaldehyde for Lig$^{11}$H$_2$, or to an equimolar amount of 3,5-diiodosalicylaldehyde for Lig$^{12}$H$_2$) in ethanol and the reaction mixture was stirred for 2 hours. The solvent was thereafter removed under vacuum yielding an orange solid (4.92 grams, 99%). The following presents the analytical data obtained for 2-((methylamino)ethylimino)methyl)-3,5-dichlorophenol, as a representative example:

$^1$H NMR (CDCl$_3$, 200 MHz): δ=7.35 (d, 1H, J=2.6 Hz, ArH), 7.09 (d, 1H, J=2.6 Hz, ArH), 3.46 (m, 2H, NCH$_2$), 2.95 (m, 2H, NCH$_2$), 2.43 (s, 3H, NCH$_3$) ppm.

Preparation of Lig$^{10}$H$_2$: (see, FIG. 1A and Formula I, wherein R$_1$=R$_2$=Cl; R$_3$=adamantyl; R$_4$=methyl; R$_5$=R$_6$=R$_7$=R$_8$=H; Z=Y=CH$_2$; R'=H; and R=methyl)

A solution of 2-(bromomethyl)-4-methyl-6-adamantyl-phenol (0.47 gram, 1.4 mmol) in THF (20 mL) was added dropwise to a solution of 2-((methylamino)ethylimino) methyl)-4,6-dichlorophenol (0.35 gram, 1.4 mmol) and triethylamine (3 mL) in THF (20 mL) and the reaction mixture was stirred for 5 hours. The solid that formed was filtered out and the solvent was removed under vacuum. The intermediate product was dissolved in methanol and cooled in a water bath. Approximately 0.5 gram of NaBH$_4$ was added by small portions and the reaction mixture was stirred for 5 hours at room temperature. The solvent was removed under vacuum and 50 mL of water was added. The final product was extracted with 3 portions (50 mL) of dichloromethane, dried on MgSO$_4$, filtered and dried under vacuum. Yield 0.66 gram (89%).

Preparation of Lig$^{11}$H$_2$ (see, FIG. 1A and Formula I, wherein R$_1$=R$_2$=Br; R$_3$=adamantyl; R$_4$=methyl; R$_5$=R$_6$=R$_7$=R$_8$=H; Z=Y=CH$_2$; R'=H; and R=methyl):

A solution of 2-(bromomethyl)-4-methyl-6-adamantyl-phenol (0.58 gram, 1.7 mmol) in THF (20 mL) was added dropwise to a solution of 2-((methylamino)ethylimino) methyl)-4,6-dibromophenol (0.58 gram, 1.7 mmol) and triethylamine (3 mL) in THF (20 mL) and the reaction mixture was stirred for 5 hours. The solid that formed was filtered out and the solvent was removed under vacuum. The intermediate product was dissolved in methanol and cooled in a water bath. Approximately 0.5 gram of NaBH$_4$ was added by small portions and the reaction mixture was stirred for 5 hours at room temperature. The solvent was removed under vacuum and 50 mL of water was added. The final product was extracted with 3 portions (50 mL) of dichloromethane, dried on MgSO$_4$, filtered and dried under vacuum. Yield 0.83 gram (81%).

$^1$H NMR (CDCl$_3$, 400 MHz): δ=7.54 (d, 1H, J=2.2 Hz ArH), 7.08 (d, 1H, J=1.3 Hz ArH), 6.63 (d, 1H, J=2.2 Hz ArH), 6.50 (d, 1H, J=1.3 Hz ArH), 3.08 (s, 2H, CH$_2$), 2.92 (s, 2H, CH$_2$), 2.35 (s, 6H, Adamantyl), 2.25 (s, 3H, CH$_3$), 2.10 (s, 3H, Adamantyl), 1.98 (t, 2H, J=6.7 Hz, NCH$_2$), 1.79 (s, 6H, Adamantyl), 1.67 (t, 2H, J=6.7 Hz, NCH$_2$), 1.63 (s, 3H, CH$_3$) ppm.

Preparation of Lig$^{12}$H$_2$ (see, FIG. 1A and Formula I, wherein R$_1$=R$_2$=I; R$_3$=adamantyl; R$_4$=methyl; R$_5$=R$_6$=R$_7$=R$_8$=H; Z=Y=CH$_2$; R'=H; and R=methyl):

A solution of 2-(bromomethyl)-4-methyl-6-adamantyl-phenol (0.62 gram, 1.8 mmol) in THF (20 mL) was added dropwise to a solution of 2-((methylamino)ethylimino) methyl)-4,6-diiodophenol (0.79 gram, 1.8 mmol) and triethylamine (3 mL) in THF (20 mL) and the reaction mixture was stirred for 5 hours. The solid that formed was filtered out and the solvent was removed under vacuum. The intermediate product was dissolved in methanol and cooled in a water bath. Approximately 0.5 gram of NaBH$_4$ was added by small portions and the reaction mixture was stirred for 5 hours at room temperature. The solvent was removed under vacuum and 50 mL of water was added. The final product was extracted with 3 portions (50 mL) of dichloromethane, dried on MgSO$_4$, filtered and dried under vacuum. Yield 1.08 gram (85%).

$^1$H NMR (CDCl$_3$, 400 MHz): δ=7.88 (d, 1H, J=1.8 Hz, ArH), 7.11 (d, 1H, J=1.8 Hz, ArH), 6.63 (s, 1H, ArH), 6.65 (s, 1H, ArH), 3.74 (s, 2H, CH$_2$), 3.65 (s, 2H, CH$_2$), 2.74 (t, 2H, J=5.6 Hz, NCH$_2$), 2.59 (t, 2H, J=5.6 Hz, NCH$_2$), 2.36 (s, 3H, CH$_3$), 2.25 (s, 3H, CH$_3$), 2.06 (s, 6H, Adamantyl), 2.01 (s, 3H, Adamantyl), 1.75 (s, 6H, Adamantyl) ppm.

II. Syntheses of Ligand Precursors from an N-Alkylaminoethylamine Skeleton in which R is an Alkyl Other than Methyl:

A general synthetic pathway of preparing Salan ligand precursors from a N-alkylaminoethylamine skeleton is presented in Scheme 2 below.

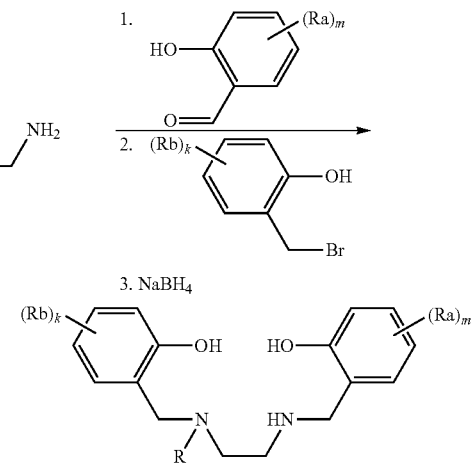

wherein R is an alkyl such as, but not limited to, phenyl-methyl (benzyl), ethyl and isopropyl, as described herein for Formula I.

N-alkylethylenediamine (1 molequivalent, wherein the alkyl is as described herein for R in Formula I) is added to a solution of a substituted 2-hydroxy-benzaldehyde in an organic non-polar solvent (e.g., benzene) and the reaction mixture is refluxed for 2 hours. The solvent is thereafter removed under vacuum, yielding a solid residue (about 100% yield). The obtained substituted 2-((alkylamino)eth-ylimino)methyl)phenol is dissolved in THF, a base (e.g., triethylamine) is added, followed by dropwise addition of a solution of a substituted 2-(bromomethyl)phenol (1 molequivalent) in THF. The reaction mixture is stirred for several (e.g., two) hours. The formed solid is thereafter filtered out and the solvent is removed under vacuum. The intermediate product is dissolved in methanol and reacted with 5 molequivalents of NaBH$_4$ (or any other reducing agent) for several (e.g., 5) hours. The solvent is removed under vacuum, and 50 mL of water are added to destroy the traces of NaBH$_4$. The final product is extracted with dichloromethane, dried with MgSO$_4$, filtered and dried in vacuum, yielding the respective ligand precursor as a white solid, typically in high to quantitative yields. Typically, no further purification steps are required.

In an exemplary general procedure, ligand precursors having the following general Formula Ib:

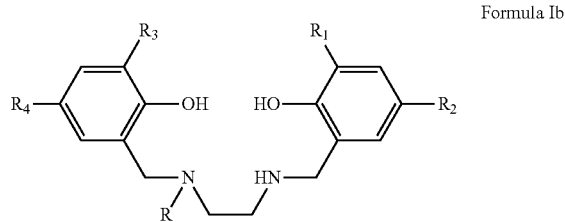

Formula Ib were prepared according to the general procedure described hereinabove, such that in Scheme 2, each of "k" and "m" is 2; Ra denotes the substituents $R_1$ and $R_2$; and Rb denotes the substituents $R_3$ and $R_4$, as described herein for Formula I; and wherein R is other than methyl.

Formula Ib corresponds to Formula I as described herein, in which $R_5=R_6=R_7=R_8=H$; $Z=Y=CH_2$; $R'=H$ and R=alkyl other than methyl, and $R_1$-$R_4$ are various combinations of substituents, as described hereinabove and indicated hereinbelow.

Using the above-described general procedure (see, Scheme 2), exemplary Salan ligand precursors having Formula IB, which are referred to herein as $Lig^{13-17}H_2$, were prepared, as representative ligand precursors having a (N-alkylamino)ethylamino bridging unit. These exemplary ligands are further characterized by one or more bulky groups on the phenol proximal to the secondary (N-H) amine nitrogen (e.g., $R_1$ and $R_2$ in the above general Formula 1b) and by bulky or electron-withdrawing substituents (halo-substituents) on the other phenol arm (e.g., $R_3$ and $R_4$ in the above general Formula 1b).

Figure 1B:
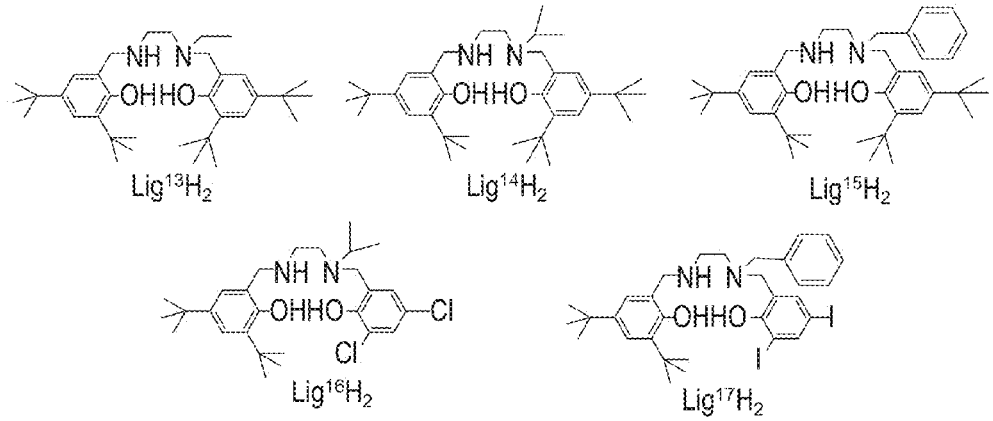

The chemical structures of $Lig^{13-17}H_2$ are presented in FIG. 1B.

The structures of all intermediates and final products were verified by NMR measurements.

The following describes in detail the procedures used for preparing exemplary such ligand precursors.

Preparation of $Lig^{13}H_2$ (see, FIG. 1B and Formula I, wherein $R_1=R_2=R_3=R_4=$t-Bu; $R_5=R_6=R_7=R_8=H$; $Z=Y=CH_2$; $R'=H$; and R=ethyl):

(a) Synthesis of 2-((ethylamino)ethylimino)methyl)-3,5-tert-butylphenol: N-ethylethylenediamine (0.86 gram, 9.7 mmol) was added to a solution of 3,5-di-tert-butyl-2-hydroxybenzaldehyde (2.28 gram, 9.7 mmol) in benzene and the reaction mixture was refluxed for 2 hours. The solvent was removed under vacuum yielding a yellow oil (2.94 grams, 100%).

$^1$H NMR (CDCl$_3$, 400 MHz): δ=8.40 (s, 1H, NCH), 7.38 (d, 1H, J=2.4 Hz, ArH), 7.08 (d, 1H, J=2.4 Hz, ArH), 3.72 (t, 2H, J=6.0 Hz, NCH$_2$), 2.95 (t, 2H, J=6.0 Hz, NCH$_2$), 2.68 (q, 2H, J=6.2 Hz, NCH), 1.44 (s, 9H, (CH$_3$)$_3$), 1.30 (s, 9H, (CH$_3$)$_3$), 1.10 (t, 4H, J=6.2 Hz, CH$_3$) ppm.

$^{13}$C NMR (CDCl$_3$, 100.67 MHz): δ=167.8 (CN), 158.7 (CO), 140.8 (C), 137.4 (C), 127.6 (CH), 125.5 (CH), 118.5 (C), 60.5 (CH$_2$), 50.5 (CH$_2$), 45.0 (CH$_2$), 37.8 (C), 35.7 (C), 32.2 ((CH$_3$)$_3$), 30.2 ((CH$_3$)$_3$), 16.0 (CH$_3$) ppm.

(b) Synthesis of the ligand precursor $Lig^{13}H_2$: A solution of 2-(bromomethyl)-4,6-di-tert-butylphenol (1.38 gram, 4.6 mmol,) in THF (20 mL) was added dropwise to a solution of 2-((ethylamino)ethylimino)methyl)-3,5-di-tert-butylphenol (1.40 gram, 4.6 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ were added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum.

$^1$H NMR (CDCl$_3$, 400 MHz): δ=7.21 (d, 1H, J=2.3 Hz ArH), 7.19 (d, 1H, J=2.3 Hz ArH), 6.83 (d, 1H, J=2.3 Hz ArH), 6.79 (d, 1H, J=2.3 Hz ArH), 3.87 (s, 2H, CH$_2$), 3.75 (s, 2H, CH$_2$), 2.80 (t, 2H, J=6.4 Hz, NCH$_2$), 2.68 (t, 2H, J=6.4 Hz, NCH$_2$), 2.64 (q, 1H, J=7.1 Hz, CH$_2$), 1.39 (s, 9H, (CH$_3$)$_3$), 1.36 (s, 9H, (CH$_3$)$_3$), 1.27 (s, 9H, (CH$_3$)$_3$), 1.24 (s, 9H, (CH$_3$)$_3$), 1.12 (t, 3H, J=7.1 Hz, CH$_3$) ppm.

$^{13}$C NMR (CDCl$_3$, 100.67 MHz): δ=155.2 (CO), 154.8 (CO), 141.4 (C), 141.1 (C), 136.5 (CH), 124.0 (CH), 123.9 (CH), 123.6 (CH), 122.3 (C), 121.9 (C), 59.5 (CH$_2$), 54.1 (CH$_2$), 53.1 (CH$_2$), 48.5 (CH$_2$), 46.5 (CH$_2$), 35.6 (C), 34.8 (C), 32.3 ((CH$_3$)$_3$), 32.4 ((CH$_3$)$_3$), 30.3 ((CH$_3$)$_3$), 30.2 ((CH$_3$)$_3$), 11.8 (CH$_3$) ppm.

Preparation of $Lig^{14}H_2$ (see, FIG. 1B and Formula I, wherein $R_1=R_2=R_3=R_4=$t-Bu; $R_5=R_6=R_7=R_8=H$; $Z=Y=CH_2$; $R'=H$; and R=isopropyl):

(a) Synthesis of 2-((isopropylamino)ethylimino)methyl)-3,5-tert-butylphenol: N-isopropylethylenediamine (0.65 gram, 6.4 mmol) was added to a solution of 3,5-di-tert-butyl-2-hydroxybenzaldehyde (1.49 gram, 6.4 mmol) in benzene and the reaction mixture was refluxed for 2 hours. The solvent was removed under vacuum yielding a yellow oil (2.02 grams, 100%).

$^1$H NMR (CDCl$_3$, 400 MHz): δ=8.41 (s, 1H, NCH), 7.39 (d, 1H, J=1.8 Hz, ArH), 7.10 (d, 1H, J=1.8 Hz, ArH), 3.73 (t, 2H, J=5.8 Hz, NCH$_2$), 2.94 (t, 2H, J=5.8 Hz, NCH$_2$), 2.84 (septet, 1H, J=6.2 Hz, NCH), 1.45 (s, 9H, (CH$_3$)$_3$), 1.31 (s, 9H, (CH$_3$)$_3$), 1.07 (d, 6H, J=6.2 Hz, CH$_3$) ppm.

$^{13}$C NMR (CDCl$_3$, 100.67 MHz): δ=167.0 (CN), 157.9 (CO), 139.9 (C), 128.2 (C), 126.8 (CH), 125.8 (CH), 117.7 (C), 59.8 (CH$_2$), 48.4 (CH$_2$), 47.4 (NCH), 34.9 (C), 34.0 (C), 31.4 ((CH$_3$)$_3$), 29.3 ((CH$_3$)$_3$), 22.7 ((CH$_3$)$_3$) ppm.

(b) Synthesis of the ligand precursor $Lig^{14}H_2$: A solution of 2-(bromomethyl)-4,6-di-tert-butylphenol (1.46 gram, 4.9 mmol,) in THF (20 mL) was added dropwise to a solution of 2-((isopropylamino)ethylimino)methyl)-3,5-di-tert-butyl-phenol (1.57 gram, 4.9 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ was added by small portions until the solution turned to colorless and stirred for 2 hours. The solvent was removed under vacuum and 50 mL of water added to the solution. The final product was extracted with 3 portions of dichloromethane, dried on MgSO$_4$, filtered and dried in vacuum.

$^1$H NMR (CDCl$_3$, 400 MHz): δ=7.24 (d, 1H, J=2.0 Hz ArH), 7.23 (d, 1H, J=2.0 Hz ArH), 6.87 (d, 1H, J=2.0 Hz ArH), 6.82 (d, 1H, J=2.3 Hz ArH), 3.88 (s, 2H, CH$_2$), 3.80 (s, 2H, CH$_2$), 3.15 (sept, 1H, J=6.6 Hz, NCH$_2$), 2.80 (t, 2H, J=6.1 Hz, NCH$_2$), 2.68 (t, 2H, J=6.1 Hz, CH$_2$), 1.44 (s, 9H, (CH$_3$)$_3$), 1.40 (s, 9H, (CH$_3$)$_3$), 1.31 (s, 9H, (CH$_3$)$_3$), 1.27 (s, 9H, (CH$_3$)$_3$), 1.13 (d, 6H, J=6.6 Hz, CH$_3$) ppm.

$^{13}$C NMR (CDCl$_3$, 100.67 MHz): δ=155.3 (CO), 155.1 (CO), 141.4 (C), 141.1 (C), 136.5 (CH), 136.3 (CH), 124.3 (CH), 124.0 (CH), 123.7 (CH), 123.6 (CH), 122.5 (C), 122.0

(C), 55.7 (CH$_2$), 54.1 (CH$_2$), 51.3 (CH), 49.5 (CH$_2$), 47.6 (CH$_2$), 35.6 (C), 34.9 (C), 34.8 (C), 32.5 ((CH$_3$)$_3$), 32.4 ((CH$_3$)$_3$), 30.4 ((CH$_3$)$_3$), 30.3 ((CH$_3$)$_3$), 18.0 (CH$_3$) ppm.

Preparation of Lig$^{15}$H$_2$ (see, FIG. 1B and Formula I, wherein R$_1$=R$_2$=R$_3$=R$_4$=t-Bu; R$_5$=R$_6$=R$_7$=R$_8$=H; Z=Y=CH$_2$; R'=H; and R=benzyl):

(a) Synthesis of 2-((benzylamino)ethylimino)methyl)-3,5-tert-butylphenol: N-benzylethylenediamine (3.56 gram, 23.7 mmol) was added to a solution of 3,5-di-tert-butyl-2-hydroxybenzaldehyde (5.55 gram, 23.7 mmol) in benzene and the reaction mixture was refluxed for 2 hours. The solvent was removed under vacuum yielding a yellow oil (8.68 grams, 100%).

$^1$H NMR (CDCl$_3$, 400 MHz): δ=8.46 (s, 1H, NCH), 7.47 (d, 1H, J=2.4 Hz, ArH), 7.40-7.38 (m, 5H, ArH), 7.17 (d, 1H, J=2.4 Hz, ArH), 3.91 (s, 2H, CH$_2$), 3.79 (t, 2H, J=5.6 Hz, NCH$_2$), 3.03 (t, 2H, J=5.6 Hz, NCH$_2$), 1.54 (s, 9H, (CH$_3$)$_3$), 1.39 (s, 9H, (CH$_3$)$_3$) ppm.

$^{13}$C NMR (CDCl$_3$, 100.67 MHz): δ=167.2 (CN), 158.1 (CO), 140.3 (C), 140.1 (C), 136.7 (C), 128.8 (CH), 128.2 (CH), 127.6 (CH), 126.0 (CH), 117.9 (C), 59.7 (CH$_2$), 53.8 (CH$_2$), 49.3 (CH$_2$), 35.1 (C), 34.2 (C), 31.6 ((CH$_3$)$_3$), 29.6 ((CH$_3$)$_3$) ppm.

(b) Synthesis of the ligand precursor Lig$^{15}$H$_2$: A solution of 2-bromomethyl)-4,6-di-tert-butylphenol (1.48 gram, 4.9 mmol,) in THF (20 mL) was added dropwise to a solution of 2-((benzylamino)ethylimino)methyl)-3,5-tert-butylphenol (1.82 gram, 4.9 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ was added in small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum.

$^1$H NMR (CDCl$_3$, 400 MHz): δ=7.38-7.34 (m, 5H, ArH), 7.28 (d, 1H, J=2.2 Hz ArH), 7.25 (d, 1H, J=2.2 Hz ArH), 6.91 (d, 1H, J=2.2 Hz ArH), 6.77 (d, 1H, J=2.2 Hz ArH), 3.84 (s, 2H, CH$_2$), 3.78 (s, 2H, CH$_2$), 3.69 (s, 2H, CH$_2$), 2.86 (t, 2H, J=6.2 Hz, NCH$_2$), 2.73 (t, 2H, J=6.2 Hz, NCH$_2$), 1.48 (s, 9H, (CH$_3$)$_3$), 1.40 (s, 9H, (CH$_3$)$_3$), 1.35 (s, 9H, (CH$_3$)$_3$), 1.33 (s, 9H, (CH$_3$)$_3$) ppm.

$^{13}$C NMR (CDCl$_3$, 100.67 MHz): δ=155.3 (CO), 154.5 (CO), 141.7 (C), 141.1 (C), 137.7 (C), 136.6 (C), 136.5 (C), 130.4 (CH), 129.4 (CH), 128.4 (CH), 124.4 (CH), 123.9 (CH), 123.8 (CH), 123.7 (CH), 122.3 (C), 121.9 (C), 60.0 (CH$_2$), 59.5 (CH$_2$), 53.7 (CH$_2$), 53.2 (CH$_2$), 46.2 (CH$_2$), 35.7 (C), 35.6 (C), 34.9 (C), 34.8 (C), 32.4 ((CH$_3$)$_3$), 32.3 ((CH$_3$)$_3$), 30.4 ((CH$_3$)$_3$), 30.3 ((CH$_3$)$_3$) ppm.

Preparation of Lig$^{16}$H$_2$ (see, FIG. 1B and Formula I, wherein R$_1$=R$_2$=t-Bu; R$_3$=R$_4$=Cl; R$_5$=R$_6$=R$_7$=R$_8$=H; Z=Y=CH$_2$; R'=H; and R=isopropyl):

A solution of 2-(bromomethyl)-4,6-dichlorophenol (0.56 gram, 2.2 mmol,) in THF (20 mL) was added dropwise to a solution of 2-((isopropylamino)ethylimino)methyl)-3,5-tert-butylphenol (0.71 gram, 2.2 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum.

$^1$H NMR (CDCl$_3$, 400 MHz): δ=7.23 (d, 1H, J=2.5 Hz, ArH), 7.20 (d, 1H, J=2.5 Hz, ArH), 6.84 (d, 1H, J=2.4 Hz, ArH), 6.81 (d, 1H, J=2.4 Hz, ArH), 3.92 (s, 2H, CH$_2$), 3.76 (s, 2H, CH$_2$), 3.04 (sept, 1H, J=6.3 Hz, NCH$_2$), 2.83 (t, 2H, J=6.8 Hz, NCH$_2$), 2.63 (t, 2H, J=6.8 Hz, CH$_2$), 1.39 (s, 9H, (CH$_3$)$_3$), 1.26 (s, 9H, (CH$_3$)$_3$), 1.08 (d, 6H, J=6.7 Hz, CH$_3$) ppm.

Preparation of Lig$^{17}$H$_2$ (see, FIG. 1B and Formula I, wherein R$_1$=R$_2$=t-Bu; R$_3$=R$_4$=I; R$_5$=R$_6$=R$_7$=R$_8$=H; Z=Y=CH$_2$; R'=H; and R=benzyl):

A solution of 2-(bromomethyl)-4,6-diiodobutylphenol (0.61 gram, 1.4 mmol,) in THF (20 mL) was added dropwise to a solution of 2-((benzylamino)ethylimino)methyl)-3,5-di-tert-butylphenol (0.51 gram, 1.4 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ was added in small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum.

$^1$H NMR (CDCl$_3$, 400 MHz): δ=7.95 (d, 1H, J=2.0 Hz ArH), 7.38-7.23 (m, 7H, ArH), 6.79 (d, 1H, J=2.0 Hz ArH), 3.85 (s, 2H, CH$_2$), 3.73 (s, 2H, CH$_2$), 3.67 (s, 2H, CH$_2$), 2.87 (t, 2H, J=6.3 Hz, NCH$_2$), 2.70 (t, 2H, J=6.3 Hz, NCH$_2$), 1.41 (s, 9H, (CH$_3$)$_3$), 1.30 (s, 9H, (CH$_3$)$_3$) ppm.

$^{13}$C NMR (CDCl$_3$, 100.67 MHz): δ=156.9 (CO), 154.3 (CO), 145.5 (CH), 140.6 (C), 137.2 (CH), 135.4 (C), 129.7 (CH), 128.9 (CH), 128.2 (CH), 124.1 (C), 123.3 (CH), 123.1 (CH), 121.4 (C), 86.1 (C), 81.0 (C), 58.7 (CH$_2$), 57.5 (CH$_2$), 53.2 (CH$_2$), 52.5 (CH$_2$), 45.3 (CH$_2$), 34.9 (C), 34.1 (C), 31.7 ((CH$_3$)$_3$), 29.7 ((CH$_3$)$_3$) ppm.

III. Syntheses of Ligand Precursors from a Chiral Diamino Skeleton:

An exemplary general synthetic pathway of preparing Salan ligand precursors from a chiral diamino skeleton such as, for example, 2-aminomethylpyrrolidine, is presented in Scheme 3 below.

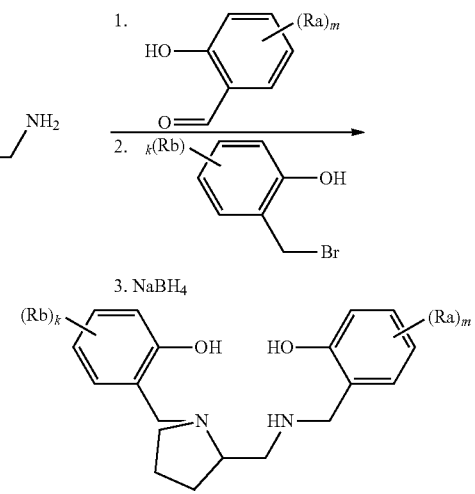

Scheme 3

S-(2)-Pyrrolidinemethanamine.2HCl (1 molequivalent) is added to a solution of a substituted 2-hydroxy-benzaldehyde in an organic non-polar solvent (e.g., benzene) and a base (e.g., triethylamine) and the reaction mixture is refluxed for several (e.g., 5) hours. The formed solid is filtered out and the solvent is thereafter removed under vacuum, yielding a solid residue (>70% yield). The obtained substituted 2-(iminomethyl)phenol is dissolved in THF, a base (e.g., triethylamine) is added, and to the obtained solution, a solution of a substituted 2-(bromomethyl)phenol (1 molequivalent) in THF is added dropwise and the reaction mixture is stirred for several (e.g., 2) hours. The formed solid is thereafter filtered out and the solvent is removed under vacuum. The intermediate product is dissolved in methanol and 5 molequivalent of $NaBH_4$ added by small portions until the solution turns to colorless and the reaction mixture is stirred for several (e.g., 2) hours. The solvent is removed under vacuum and 50 mL of water added to the solution. The final product is extracted with 3 portions of dichloromethane, dried on $MgSO_4$, filtered and dried in vacuum.

In a typical general procedure, ligand precursors having the following general Formula Ic were prepared:

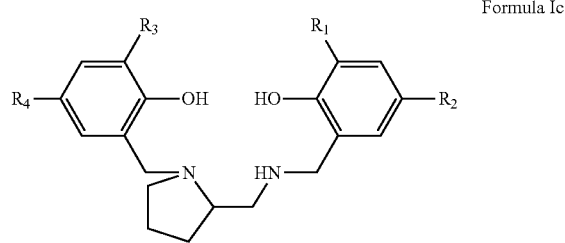

Formula Ic such that in Scheme 3 above each of "k" and "m" is 2; Ra denotes the substituents $R_1$ and $R_2$ as described herein; and Rb denotes the substituents $R_3$ and $R_4$ as described herein.

Formula Ic corresponds to Formula I as described herein, in which $R_5=R_6=R_7=R_8=H$; $Y=CH_2$; $Z=CRaRb$ wherein Rb=H and Ra and R are linked together to form a pyrrolidine; R'=H, and $R_1$-$R_4$ are various combinations of substituents, as described hereinabove.

Using the above-described general procedure (see, Scheme 3), exemplary Salan ligand precursors having Formula IC, which are referred to herein as $Lig^{18-26}H_2$, were prepared, as representative ligand precursors having a chiral bridging unit. These exemplary ligands are further characterized by one or more bulky groups and/or by electron-withdrawing substituents (halo-substituents) on one or both phenol arms (e.g., $R_1$-$R_4$ in the above general Formula Ic). The chemical structures of $Lig^{18-26}H_2$ are presented in FIG. 2.

The structures of all intermediates and final products were verified by NMR measurements.

The following describes in detail the procedures used for preparing exemplary such ligand precursors.

Synthesis of 2-((S)-(aminomethyl)pyrrolidine)-4-methyl-6-adamantylphenol: S-(2)-Pyrrolidinemethanamine.2HCl (0.23 gram, 1.3 mmol) was added to a solution of 3-adamantyl-2-hydroxy-5-methylbenzaldehyde (0.36 gram, 1.3 mmol) in benzene, followed by addition of triethylamine (3 mL), and the reaction mixture was refluxed for 5 hours. The obtained solution was thereafter filtered and the solvent was removed under vacuum yielding a yellow solid (0.37 gram, 78%).

$^1$H NMR ($CDCl_3$, 400 MHz): δ=8.35 (s, 1H, NCH), 7.08 (s, 1H, ArH), 6.91 (s, 1H, ArH), 3.73 (m, 1H, CH), 3.55 (m, 1H, CH), 3.43 (m, 1H, CH), 3.05 (m, 1H, CH), 2.84 (m, H, CH), 2.29 (s, 3H, $CH_3$), 2.19 (bs, 6H, Adamantyl), 2.10 (bs, 3H, Adamantyl), 1.98-1.94 (m, 3H, CH), 1.81 (m, 6H, Adamantyl) ppm.

$^{13}$C NMR ($CDCl_3$, 100.67 MHz): δ=166.7 (CN), 158.5 (CO), 136.8 (C), 130.5 (CH), 129.4 (C), 128.3 (CH), 126.7 (C), 64.8 ($CH_2$), 58.8 (CH), 46.1 ($CH_2$), 45.8 ($CH_2$), 40.9 ($CH_2$), 37.2 ($CH_2$), 36.9 ($CH_2$), 29.1 ($ArCH_3$), 25.1 ($CH_2$), 20.7 ($CH_2$) ppm.

Figure 2:
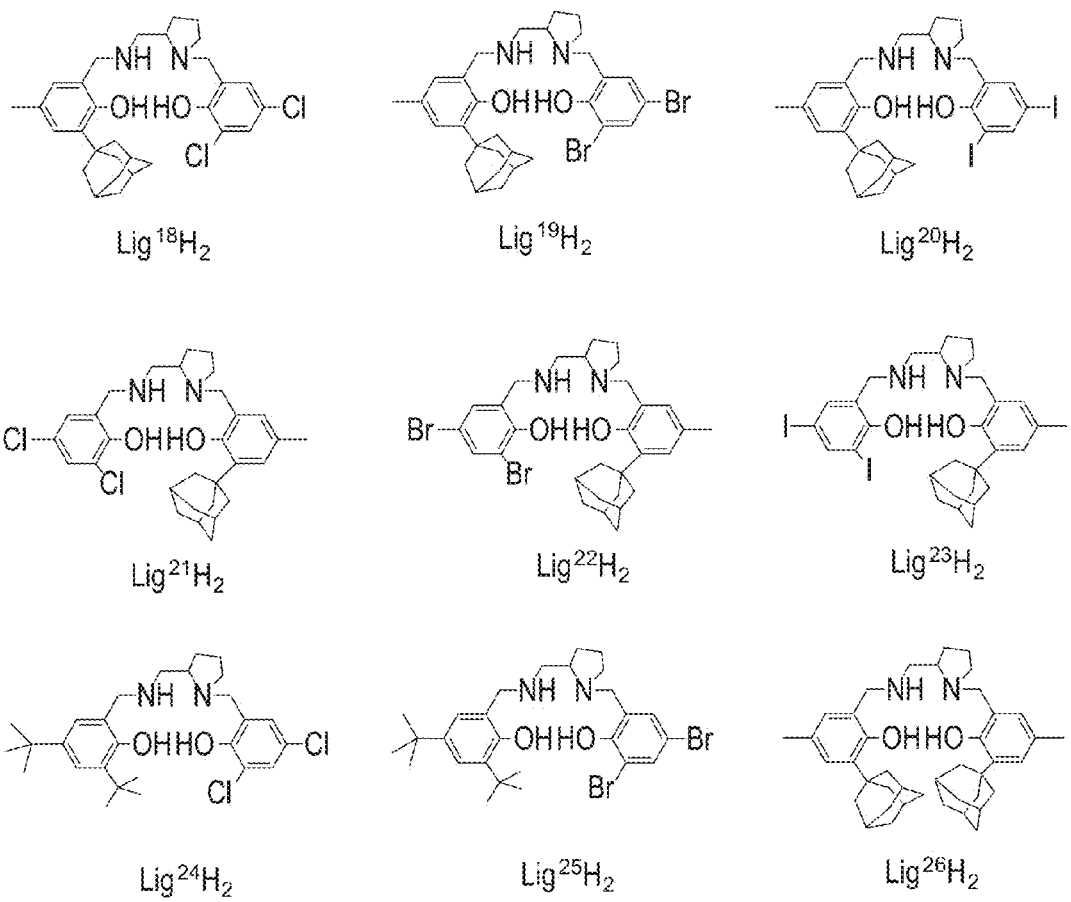
FIG. 2 presents the chemical structures of exemplary Salan ligand precursors according to some embodiments of the present invention, based on a 2-aminomethyl-pyrrolidine skeleton (Lig$^{18-26}$H$_2$)
Figure 3:
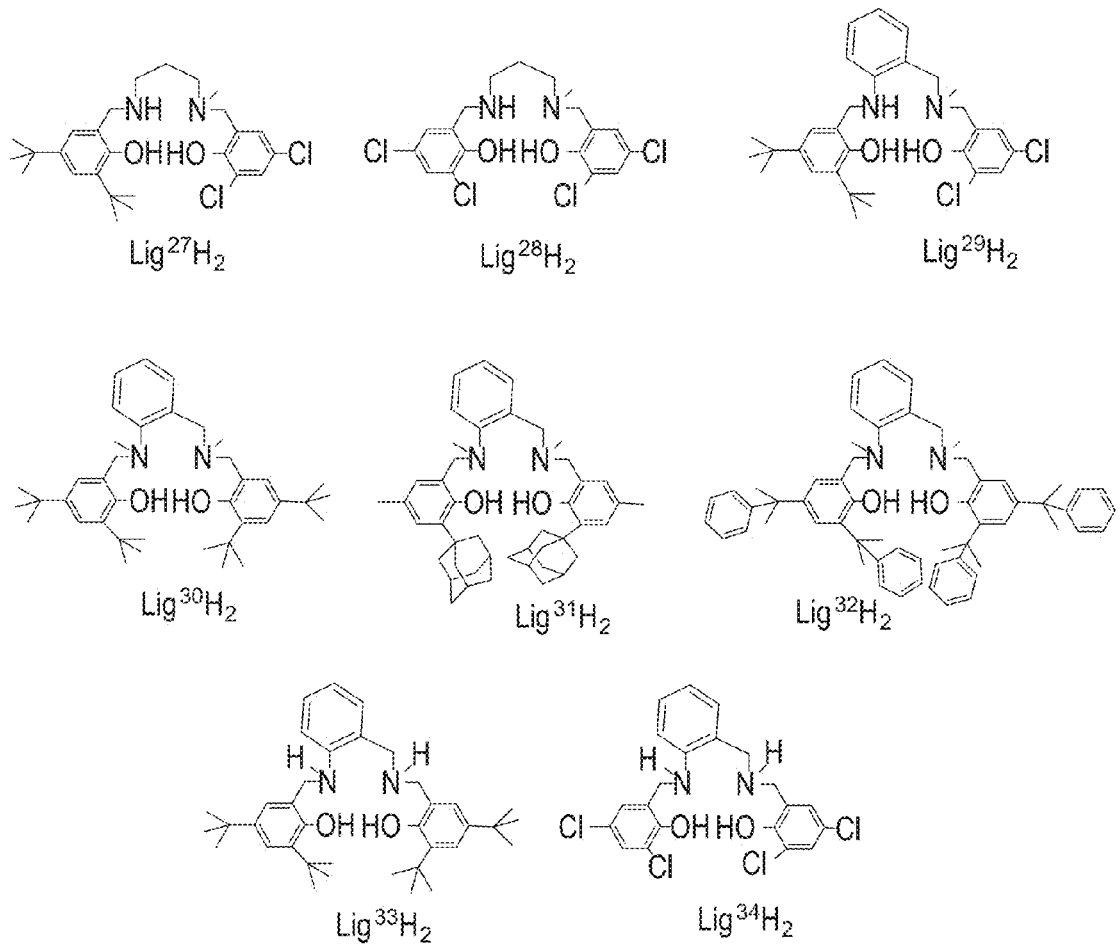
FIG. 3 presents the chemical structures of exemplary Salan ligand precursors according to some embodiments of the present invention, based on a propylenediamine skeleton (Lig$^{27-34}$H$_2$)

Preparation of $Lig^{18}H_2$ (see, FIG. 2 and Formula Ic wherein $R_1=R_2=Cl$; $R_3$=adamantyl; and $R_4$=methyl):

A solution of 2-(bromomethyl)-4,6-dichlorophenol (0.25 gram, 1.0 mmol) in THF (20 mL) was added dropwise to a solution of 2-((S)-(aminomethyl)pyrrolidine)-4-methyl-6-adamantylphenol (0.35 gram, 1.0 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of $NaBH_4$ added by small portions until the solution turned to colorless and the reaction mixture was stirred for 2 hours. The solvent was removed under vacuum and 50 mL of water added to the solution. The final product was extracted with 3 portions of dichloromethane, dried on $MgSO_4$, filtered and dried in vacuum. Yield 0.43 gram (81%).

$^1$H NMR ($CDCl_3$, 400 MHz): δ=7.24 (d, 1H, J=2.4 Hz, ArH), 6.93 (d, 1H, J=1.8 Hz, ArH), 6.85 (d, 1H, J=2.4 Hz ArH), 6.66 (d, 1H, J=1.8 Hz, ArH), 4.18 (d, 1H, J=14.2 Hz, CH), 3.92 (s, 2H, $CH_2$), 3.45 (d, 1H, J=14.2 Hz, CH), 3.05 (m, 1H, CH), 2.88 (m, 1H, CH), 2.73 (m, 2H, CH), 2.32 (m, 1H, CH), 2.23 (s, 3H, $CH_3$), 2.09 (bs, 6H, Adamantyl), 2.07 (m, 1H, CH), 2.04 (bs, 3H, Adamantyl), 1.84-1.79 (m, 3H, CH), 1.76 (m, 6H, Adamantyl) ppm.

$^{13}$C NMR ($CDCl_3$, 100.67 MHz): δ=155.2 (CO), 153.3 (CO), 137.6 (C), 129.3 (CH), 128.2 (C), 127.9 (CH), 126.8 (CH), 126.2 (CH), 125.0 (C), 124.1 (C), 123.1 (C), 122.2 (C), 64.9 (CH), 58.5 ($CH_2$), 55.0 ($CH_2$), 54.1 ($CH_2$), 52.1 ($CH_2$), 41.1 ($CH_2$, Adamantyl), 37.9 ($CH_2$, Adamantyl), 31.1 (C, Adamantyl), 30.0 ($CH_2$), 30.4 (CH, Adamantyl), 23.5 ($CH_2$), 23.5 ($CH_3$) ppm.

Preparation of $Lig^{19}H_2$ (see, FIG. 2 and Formula Ic wherein $R_1=R_2=Br$; $R_3$=adamantyl; and $R_4$=methyl):

A solution of 2-(bromomethyl)-4,6-dibromophenol (0.44 gram, 1.3 mmol) in THF (20 mL) was added dropwise to a solution of 2-((S)-(aminomethyl)pyrrolidine)-4-methyl-6-adamantylphenol (0.45 gram, 1.3 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of $NaBH_4$ added by small portions until the solution turned to colorless and the reaction mixture was stirred for 2 hours. The solvent was removed under vacuum and 50 mL of water added to the solution. The final product was extracted with 3 portions of dichloromethane, dried on $MgSO_4$, filtered and dried in vacuum. Yield 0.51 gram (74%).

$^1$H NMR ($CDCl_3$, 400 MHz): δ=7.54 (s, 1H, ArH), 7.02 (s, 1H, ArH), 6.93 (s, 1H, ArH), 6.65 (s, 1H, ArH), 4.19 (d, 1H, J=13.7 Hz, CH), 3.92 (s, 2H, $CH_2$), 3.43 (d, 1H, J=13.7 Hz, CH), 3.05 (m, 1H, CH), 2.87 (m, 1H, CH), 2.75-2.69 (m, 2H, CH), 2.33-2.26 (m, 2H, CH), 2.23 (s, 3H, $CH_3$), 2.11 (bs, 6H, Adamantyl), 2.04 (bs, 3H, Adamantyl), 1.85-1.80 (m, 3H, CH), 1.76 (m, 6H, Adamantyl) ppm.

$^{13}$C NMR ($CDCl_3$, 100.67 MHz): δ=155.2 (CO), 154.7 (CO), 137.7 (C), 134.7 (CH), 130.3 (CH), 128.2 (C), 127.8

(CH), 127.5 (CH), 125.4 (C), 123.1 (C), 111.6 (C), 111.2 (C), 64.9 (CH), 58.5 (CH$_2$), 55.0 (CH$_2$), 54.1 (CH$_2$), 52.1 (CH$_2$), 41.1 (CH$_2$, Adamantyl), 37.9 (CH$_2$, Adamantyl), 31.1 (C, Adamantyl), 30.0 (CH$_2$), 30.4 (CH, Adamantyl), 23.5 (CH$_2$), 23.5 (CH$_3$) ppm.

Preparation of Lig$^{20}$H$_2$ (see, FIG. 2 and Formula Ic wherein R$_1$=R$_2$=I; R$_3$=adamentyl; and R$_4$=methyl):

A solution of 2-(bromomethyl)-4,6-diiodophenol (0.77 gram, 1.7 mmol) in THF (20 mL) was added dropwise to a solution of 2-((S)-(aminomethyl)pyrrolidine)-4-methyl-6-adamantylphenol (0.62 gram, 1.7 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum. Yield 1.16 gram (93%).

$^1$H NMR (CDCl$_3$, 400 MHz): δ=7.90 (s, 1H, ArH), 7.06 (s, 1H, ArH), 6.89 (s, 1H, ArH), 67 (s, 1H, ArH), 4.25 (d, 1H, J=17.5 Hz, CH), 3.91 (s, 2H, CH$_2$), 3.85 (m, 1H, CH), 2.61 (m, 1H, CH), 3.39 (d, 1H, J=17.5 Hz, CH), 3.10-3.03 (m, 2H, CH), 2.75-2.67 (m, 2H, CH), 2.36 (m, 1H, CH), 2.23 (s, 3H, CH$_3$), 2.14 (bs, 6H, Adamantyl), 2.05 (bs, 3H, Adamantyl), 1.83-1.79 (m, 2H, CH), 1.77 (m, 6H, Adamantyl) ppm.

$^{13}$C NMR (CDCl$_3$, 100.67 MHz): δ=158.3 (CO), 157.2 (CO), 145.1 (CH), 136.7 (CH), 131.2 (CH), 129.5 (CH), 127.4 (C), 126.9 (C), 126.5 (C), 124.8 (C), 121.5 (C), 118.2 (C), 64.9 (CH), 58.0 (CH$_2$), 55.3 (CH$_2$), 54.4 (CH$_2$), 51.7 (CH$_2$), 40.5 (CH$_2$, Adamantyl), 37.3 (CH$_2$, Adamantyl), 30.5 (C, Adamantyl), 29.8 (CH$_2$), 29.3 (CH, Adamantyl), 23.2 (CH$_2$), 20.9 (CH$_3$) ppm.

Preparation of Lig$^{21}$H$_2$ (see, FIG. 2 and Formula Ic wherein R$_1$=adamantyl; R$_2$=methyl; and R$_3$=R$_4$=Cl):

(a) Synthesis of 2-((S)-(aminomethyl)pyrrolidine)-4,6-dichlorophenol: S-(2)-Pyrrolindinemethanamine.2HCl (0.52 gram, 3.0 mmol) was added to a solution of 3,5-dichloro-2-hydroxybenzaldehyde (0.57 gram, 3.0 mmol) in benzene, followed by addition of triethylamine (3 mL), and the reaction mixture was refluxed for 5 hours. The obtained solution was thereafter filtered and the solvent was removed under vacuum yielding red oil (0.82 gram, 100%).

(b) A solution of 2-(bromomethyl)-4-methyl-6-adamantylphenol (0.42 gram, 1.2 mmol) in THF (20 mL) was added dropwise to a solution of 2-((S)-(aminomethyl)pyrrolidine)-4,6-dichlorophenol (0.34 gram, 1.2 mmol) and triethylamine (3 mL) in THF (20 mL), and the reaction mixture was stirred for 5 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum. Yield 0.56 gram (89%).

Preparation of Lig$^{22}$H$_2$ (see, FIG. 2 and Formula Ic wherein R$_1$=adamantyl; R$_2$=methyl; and R$_3$=R$_4$=Br):

(a) Synthesis of 2-((S)-(aminomethyl)pyrrolidine)-4,6-dibromophenol: S-(2)-Pyrrolindinemethanamine. 2HCl (0.60 gram, 3.4 mmol) was added to a solution of 3,5-dibromo-2-hydroxybenzaldehyde (0.97 gram, 3.4 mmol) in benzene, followed by addition of triethylamine (3 mL) and the reaction mixture was refluxed for 5 hours. The obtained solution was thereafter filtered and the solvent was removed under vacuum yielding red oil (1.21 gram, 97%).

$^1$H NMR (CDCl$_3$, 400 MHz): δ=7.58 (d, J=2.4 Hz, 1H, ArH), 7.28 (s, J=2.4 Hz, 1H, ArH), 5.18 (bs, 1H, NH), 3.86 (m, 1H, CH), 3.47 (m, 1H, CH), 3.01 (m, 1H, CH), 1.93 (m, 4H, CH$_2$) ppm.

(b) A solution of 2-(bromomethyl)-4-methyl-6-adamantylphenol (0.49 gram, 1.5 mmol) in THF (20 mL) was added dropwise to a solution of 2-((S)-(aminomethyl)pyrrolidine)-4,6-dibromophenol (0.54 gram, 1.5 mmol) and triethylamine (3 mL) in THF (20 mL) and the reaction mixture was stirred for 5 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum. Yield 0.77 gram (85%).

Preparation of Lig$^{23}$H$_2$ (see, FIG. 2 and Formula Ic wherein R$_1$=adamantyl; R$_2$=methyl; and R$_3$=R$_4$=I):

(a) Synthesis of 2-((S)-(aminomethyl)pyrrolidine)-4,6-diiodophenol: S-(2)-Pyrrolindinemethanamine. 2HCl (0.23 gram, 1.3 mmol) was added to a solution of 3,5-dibromo-2-hydroxybenzaldehyde (0.50 gram, 1.3 mmol) in benzene, followed by addition of triethylamine (3 mL) and the reaction mixture was refluxed for 5 hours. The obtained solution was thereafter filtered and the solvent was removed under vacuum yielding red oil (0.60 gram, 99%).

(b) A solution of 2-(bromomethyl)-4-methyl-6-adamantylphenol (0.17 gram, 0.5 mmol) in THF (20 mL) was added dropwise to a solution of 2-((S)-(aminomethyl)pyrrolidine)-4,6-diiodophenol (0.23 gram, 0.5 mmol) and triethylamine (3 mL) in THF (20 mL) and the reaction mixture was stirred for 5 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum. Yield 0.26 gram (73%).

Preparation Lig$^{24}$H$_2$ (see, FIG. 2 and Formula Ic wherein R$_1$=R$_2$=Cl; and R$_3$=R$_4$=t-Bu):

(a) Synthesis of 2-((S)-(aminomethyl)pyrrolidine)-4,6-ditert-butylphenol: S-(2)-Pyrrolidinemethanamine.2HCl (1.53 gram, 8.8 mmol) was added to a solution of 3,5-di-tert-butyl-2-hydroxy-benzaldehyde (2.07 gram, 8.8 mmol) in benzene, followed by addition of triethylamine (3 mL) and the reaction mixture was refluxed for 5 hours. The obtained solution was thereafter filtered and the solvent was removed under vacuum yielding a yellow oil (2.77 gram, 99%).

$^1$H NMR (CDCl$_3$, 400 MHz): δ=8.35 (s, 1H, NCH), 7.32 (s, 1H, ArH), 7.04 (s, 1H, ArH), 3.69 (m, 1H, CH), 3.52 (m, 1H, CH), 3.39 (m, 1H, CH), 2.97 (m, 1H, CH), 2.86 (m, 1H, CH), 1.91-1.74 (m, 4H, CH), 1.37 (s, 9H, CH$_3$), 1.25 (s, 9H, CH$_3$) ppm.

$^{13}$C NMR (CDCl$_3$, 100.67 MHz): δ=167.8 (CN), 158.8 (CO), 141.5 (C), 137.3 (C), 127.6 (CH), 126.7 (CH), 118.5 (C), 65.2 (CH), 59.5 (CH$_2$), 47.1 (CH$_2$), 35.7 (C), 34.8 (C), 32.2 (CH$_3$), 30.1 (CH$_3$), 29.9 (CH$_2$), 25.8 (CH$_2$) ppm.

(b) A solution of 2-(bromomethyl)-4,6-dichlorophenol (0.61 gram, 2.4 mmol) in THF (20 mL) was added dropwise to a solution of 2-((S)-(aminomethyl)pyrrolidine)-4,6-ditert-butylphenol (0.76 gram, 2.4 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum. Yield 1.06 gram (73%).

Preparation of Lig$^{25}$H$_2$ (see, FIG. 2 and Formula Ic wherein R$_1$=R$_2$=Br; and R$_3$=R$_4$=t-Bu):

A solution of 2-(bromomethyl)-4,6-dibromophenol (0.39 gram, 1.3 mmol) in THF (20 mL) was added dropwise to a solution of 2-((S)-(aminomethyl)pyrrolidine)-4,6-di-tert-butylphenol (0.36 gram, 1.3 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 2 hours. The solvent was removed under vacuum and 50 mL of water added to the solution. The final product was extracted with 3 portions of dichloromethane, dried on MgSO$_4$, filtered and dried in vacuum. Yield 0.54 gram (82%).

Preparation of Lig$^{26}$H$_2$ (see, FIG. 2 and Formula Ic wherein R$_1$=R$_3$=adamentyl; and R$_2$=R$_4$=methyl):

(a) Synthesis of 6-(1-Adamantyl)-2-(bromomethyl)-4-methylphenol: To 30 mL of glacial acetic acid were added 2-(1-adamantyl)-4-methylphenol (15.0 g, 62 mmol) and paraformaldehyde (2.0 g, 68 mmol). The flask was warmed to 40° C. until the reactants had fully dissolved. Anhydrous hydrogen bromide gas (produced from 13 mL of Br$_2$ and 8.5 mL (62 mmol) of 1,2,3,4-tetrahydronaphthalene) was passed into the reaction mixture. Heat evolved and the temperature of the mixture was kept below 75° C. After 30 minutes a white precipitate formed and the HBr addition was stopped. The solid product was filtered off, washed three times with cold petroleum ether, and left to dry in air. Yield: 27.1 gram (100%).

m.p.: 149° C.

$^1$H NMR (CDCl$_3$, 400 MHz): δ=7.07 (d, J=1.9 Hz, 1H), 6.94 (d, J=1.9 Hz, 1H), 5.26 (s, 1H), 4.6 (s, 2H), 2.28 (s, 3H), 2.16 (s, 1H), 2.15 (s, 6H), 2.12 (m, 3H), 1.81 (m, 6H) ppm.

$^{13}$C NMR (CDCl$_3$, 100.67 MHz) d: δ=152.4 (C), 138.4 (C), 130.2 (C), 129.9 (CH), 128.4 (CH), 124.5 (C), 41.2 (CH$_2$), 37.5 (CH$_2$), 37.3 (CH), 32.7 (C), 29.5 (CH$_2$) ppm.

(b) A solution of 2-(bromomethyl)-4-methyl-6-adamantylphenol (0.40 gram, 0.9 mmol) in THF (20 mL) was added dropwise to a solution of 2-((S)-(aminomethyl)pyrrolidine)-4-methyl-6-adamantylphenol (0.32 gram, 0.9 mmol) and triethylamine (3 mL) in THF (20 mL) and the reaction mixture was stirred for 5 hours. The solid that formed was filtered out and the solvent was removed under vacuum. The intermediate product was dissolved in methanol and 5 equivalents of NaBH$_4$ added by small portions until the solution turned to colorless and stirred for 2 hours. The solvent was removed under vacuum and 50 mL of water added to the solution. The final product was extracted with 3 portions of dichloromethane, dried on MgSO$_4$, filtered and dried in vacuum. Yield 0.37 gram (68%).

$^1$H NMR (CDCl$_3$, 400 MHz): δ=7.12 (s, 1H, ArH), 6.91 (s, 1H, ArH), 6.63 (s, 1H, ArH), 6.57 (s, 1H, ArH), 3.89 (d, 1H, J=14.7 Hz, CH), 3.79 (s, 2H, CH$_2$), 3.64 (d, 1H, J=14.7 Hz, CH), 3.06 (m, 1H, CH), 2.72 (m, 1H, CH), 2.57 (m, 2H, CH), 2.37 (m, 1H, CH), 2.25 (s, 3H, CH$_3$), 2.21 (s, 3H, CH$_3$), 2.12 (bs, 6H, Adamantyl), 2.10 (bs, 6H, Adamantyl), 2.03 (bs, 6H, Adamantyl), 1.89-1.75 (m, 4H, CH), 1.75 (bs, 12H, Adamantyl) ppm.

IV. Syntheses of Ligand Precursors from a 3-Carbon Diamine Skeleton:

An exemplary general synthetic pathway of preparing Salan ligand precursors from 3-carbon diamine skeleton is presented in Scheme 4 below.

Scheme 4

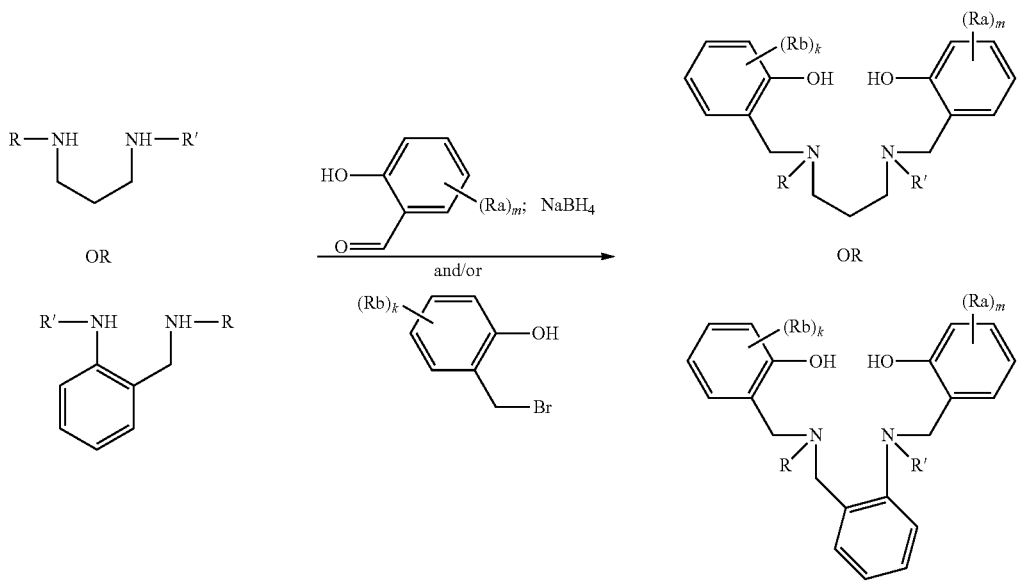

wherein R is an alkyl such as, but not limited to, methyl, benzyl, ethyl and isopropyl, as described herein, and is preferably methyl, and R' is H or alkyl, as defined for R and as described herein for Formula I.

A. Syntheses of Ligand Precursors in which R=Alkyl and R'=H:

In one exemplary general procedure, a solution of $N^1$-alkylpropane-1,3-diamine (e.g., $N^1$-methylpropane-1,3-diamine) or of 2-amino (or alkylamino)-N-methylbenzenemethanamine.2HCl (1 molequivalent) and a base (e.g., triethylamine) in an organic solvent such as benzene is added to a solution of a substituted 2-hydroxy-benzaldehyde in an organic solvent such as benzene and the reaction mixture is refluxed for several (e.g., 5) hours. The solution is then filtered and the solvent is removed under vacuum yielding a solid residue.

The obtained substituted 2-(iminomethyl)phenol is dissolved in THF, a base (e.g., triethylamine) is added, and to the obtained solution a solution of a substituted 2-(bromomethyl)phenol (1 molequivalent) in THF is added dropwise and the reaction mixture is stirred for several (e.g., 2) hours. The formed solid is thereafter filtered out and the solvent is removed under vacuum. The intermediate product is dissolved in methanol and 5 molequivalent of $NaBH_4$ are added in small portions until the solution turns to colorless, and the reaction mixture is stirred for several (e.g., 2) hours. The solvent is removed under vacuum and 50 mL of water added to the solution. The final product is extracted with 3 portions of dichloromethane, dried on $MgSO_4$, filtered and dried in vacuum. The crude product can be re-crystallized from a cold solvent (e.g., methanol) yielding the respective ligand precursor as a solid, typically in high to quantitative yields. Typically, no further purification steps are required.

In a typical such general procedure, ligand precursors having the following general Formulae Id and Ie were prepared:

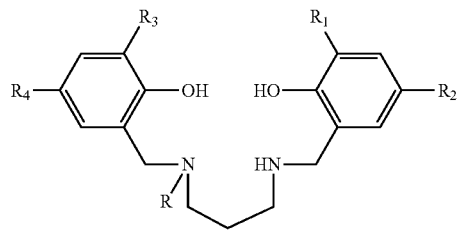

Formula Id

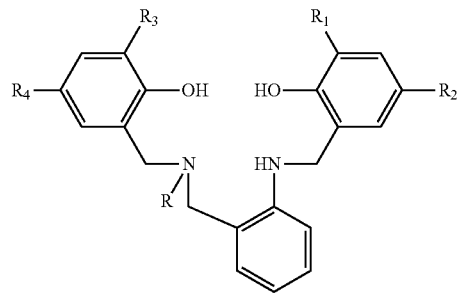

Formula Ie such that "k" and "m" in scheme 4 above is 2; Ra denotes the substituents $R_1$ and $R_2$; and Rb denotes the substituents $R_3$ and $R_4$; and R' is H.

Formula Id corresponds to Formula I as described herein, in which $R_5=R_6=R_7=R_8=H$; $Z=CH_2$; $Y=CH_2CH_2$; R'=H and R=alkyl, and $R_1$-$R_4$ are various combinations of substituents, as described hereinabove.

Formula Ie corresponds to Formula I as described herein, in which $R_5=R_6=R_7=R_8=H$; $Z=CH_2$; $Y=(CRgRh)(CRiRj)$ and Rg-Rj form together phenyl; R'=H and R=alkyl, and $R_1$-$R_4$ are various combinations of substituents, as described hereinabove.

Using the above-described general procedure (see, Scheme 4), exemplary Salan ligand precursors having Formula Id or Ie, which are referred to herein as $Lig^{27-29}H_2$ (see, FIG. 3) were prepared, as representative ligand precursors having a 3-carbon atoms bridging unit.

The following describes in detail the procedures used for preparing exemplary such ligand precursors.

Preparation of $Lig^{27}H_2$ (see, FIG. 3 and Formula Id wherein $R_1=R_2=$t-Bu; and $R_3=R_4=$Cl):

A solution of 2-(bromomethyl)-4,6-dichlorophenol (0.74 gram, 2.9 mmol,) in THF (20 mL) was added dropwise to a solution of 2,4-di-tert-butyl-6-((( 3-(methylamino) propyl) imino)methyl)phenol(0.88 gram, 2.9 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of $NaBH_4$ added by small portions until the solution turned to colorless and the reaction mixture was stirred for 5 hours. The solvent was removed under vacuum and 50 mL of water was added to the solution. The final product was extracted with 3 portions of dichloromethane, dried on $MgSO_4$, filtered and dried in vacuum. Yield 1.21 gram (87%).

$^1$H NMR ($CDCl_3$, 400 MHz): δ=7.28 (m, 2H, ArH), 6.89 (m, 1H, ArH), 3.95 (s, 2H, $CH_2$), 3.68 (s, 2H, $CH_2$), 2.77 (t, J=7.2 Hz, 2H, $CH_2$), 2.60 (t, J=7.2 Hz, 2H, $CH_2$), 2.31 (s, 3H, $NCH_3$), 1.83 (sept, J=7.2 Hz, 2H, $CH_2$), 1.41 (s, 9H, $(CH_3)_3$), 1.32 (s, 9H, $(CH_3)_3$) ppm.

$^{13}$C NMR ($CDCl_3$, 100.67 MHz): δ=155.2 (CO), 153.6 (CO), 141.3 (C), 136.6 (C), 129.4 (CH), 127.4 (CH), 124.6 (C), 124.0 (CH), 123.8 (CH), 122.6 (C), 122.2 (C), 61.6 ($CH_2$), 55.5 ($CH_2$), 54.3 ($CH_2$), 52.9 ($CH_2$), 47.1 ($CH_2$), 41.9 ($NCH_3$), 35.6 (C), 34.9 (C), 32.5 (($CH_3)_3$), 30.4 (($CH_3)_3$), 27.8 ($CH_2$) ppm.

Preparation of $Lig^{28}H_2$ (see, FIG. 3 and Formula Id wherein $R_1=R_2=R_3=R_4=$Cl):

Synthesis of 2,4-dichloro-6-(((3-(methylamino)propyl) imino)methyl)phenol: N-methyl-1,3-propane diamine (0.49 gram, 5.6 mmol) was added to a solution of 3,5-di-chloro-2-hydroxybenzaldehyde (1.06 gram, 5.6 mmol) in ethanol and the reaction mixture was stirred for 2 hours. The solvent was removed under vacuum yielding a yellow oil (1.45 gram, 100%).

Synthesis of $Lig^{28}H_2$: A solution of 2-(bromomethyl)-4,6-dichlorophenol (1.07 gram, 4.2 mmol,) in THF (20 mL) was added dropwise to a solution of 2,4-dichloro-6-(((3-(methylamino)propyl)imino)methyl)phenol (1.10 gram, 4.2 mmol) and triethylamine (3 mL) in THF (20 mL) and the reaction mixture was stirred for 2 hours. The solid that formed was filtered out and the solvent was removed under vacuum. The intermediate product was dissolved in methanol and 5 equivalents of $NaBH_4$ added by small portions until the solution turned to colorless and the reaction mixture was stirred for 5 hours. The solvent was removed under vacuum and 50 mL of water added to the solution. The final product was extracted with 3 portions of dichloromethane, dried on $MgSO_4$, filtered and dried in vacuum. Yield 1.55 gram (85%).

$^1$H NMR ($CDCl_3$, 400 MHz): δ=7.27-7.22 (m, 2H, ArH), 6.88-6.81 (m, 2H, ArH), 3.97 (s, 2H, $CH_2$), 3.68 (s, 2H,

CH$_2$), 2.73 (t, 2H, J=7.0 Hz, CH$_2$), 2.55 (t, 2H, J=7.0 Hz, CH$_2$), 2.30 (s, 3H, NCH$_3$), 1.81 (quin, 2H, J=7.0 Hz, CH$_2$) ppm.

$^{13}$C NMR (CDCl$_3$, 100.67 MHz): δ=153.6 (CO), 153.3 (CO), 129.4 (CH), 129.3 (CH), 127.3 (2CH), 124.9 (C), 124.4 (C), 124.1 (C), 122.1 (C), 61.7 (CH$_2$), 55.1 (CH$_2$), 52.9 (CH$_2$), 46.9 (CH$_2$), 41.9 (CH$_2$), 27.5 (NCH$_3$) ppm.

Preparation of Lig$^{29}$H$_2$ (see, FIG. 3 and Formula Id wherein R$_1$=R$_2$=t-Bu; and R$_3$=R$_4$=Cl):

A solution of 2-(bromomethyl)-4,6-dichlorophenol (0.71 gram, 2.8 mmol,) in THF (20 mL) was added dropwise to a solution of 2,4-di-tert-butyl-6-(((2-((methylamino)methyl)phenyl)imino)methyl)phenol (0.98 gram, 2.8 mmol) and triethylamine (3 mL) in THF (20 mL) and the reaction mixture was stirred for 4 hours. The solid that formed was filtered out and the solvent was removed under vacuum. The intermediate product was dissolved in methanol and 5 equivalents of NaBH$_4$ added by small portions until the solution turned to colorless and the reaction mixture was stirred for 5 hours. The solvent was removed under vacuum and 50 mL of water added to the solution. The final product was extracted with 3 portions of dichloromethane, dried on MgSO$_4$, filtered and dried in vacuum. Yield 1.18 gram (79%).

$^1$H NMR (CDCl$_3$, 400 MHz): δ=7.32-7.28 (m, 2H, ArH), 7.21 (d, 1H, J=2.3 Hz ArH), 7.17 (d, 1H, J=5.2 Hz, ArH), 7.12 (m, 1H, ArH), 6.99 (d, 1H, J=5.2 Hz, ArH), 6.88 (d, 1H, J=2.3 Hz, ArH), 6.93-6.91 (m, 1H, ArH), 4.42 (s, 2H, CH$_2$), 3.65 (s, 2H, CH$_2$), 3.61 (s, 2H, CH$_2$), 2.19 (s, 3H, NCH$_3$), 1.41 (s, 9H, (CH$_3$)$_3$), 1.33 (s, 9H, (CH$_3$)$_3$) ppm.

$^{13}$C NMR (CDCl$_3$, 100.67 MHz): δ=154.1 (CO), 152.0 (CO), 146.9 (C), 142.4 (C), 137.0 (C), 131.7 (CH), 130.2 (CH), 129.1 (CH), 128.3 (CH), 125.5 (CH), 124.8 (CH), 124.6 (CH), 124.5 (CH), 123.3 (CH), 123.1 (CH), 121.9 (C), 120.9 (CH), 115.1 (C), 60.4 (CH$_2$), 60.1 (CH$_2$), 49.5 (CH$_2$), 42.3 (NCH$_3$), 35.7 (C), 35.0 (C), 32.4 ((CH$_3$)$_3$), 30.5 ((CH$_3$)$_3$) ppm.

B. Syntheses of Ligand Precursors in which Both R and R' are an Alkyl:

Scheme 5

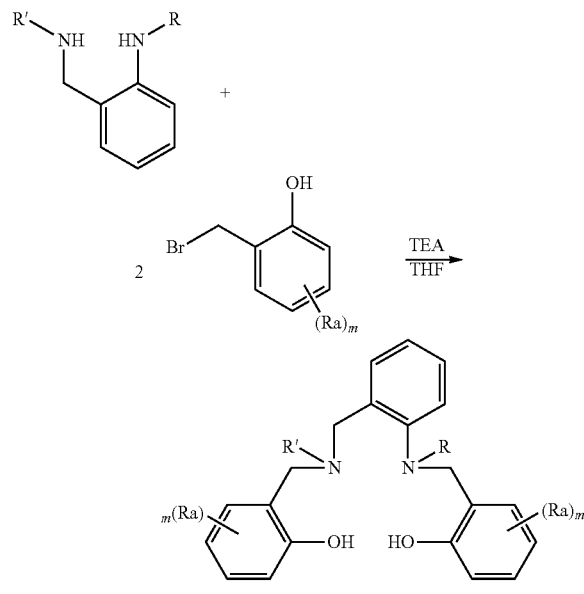

In one exemplary general procedure, depicted in Scheme 5, N,N'-dialkyl-2-aminobenzylamine.2HCl (1 molequivalent) is dissolved in THF, a base (e.g., triethylamine; TEA) is added, and to the obtained solution a solution of a substituted 2-(bromomethyl)phenol (2 molequivalent) in THF is added dropwise and the reaction mixture is stirred for several (e.g., 2) hours. The formed solid is thereafter filtered out and the solvent is removed under vacuum. The intermediate product is dissolved in methanol and 5 molequivalent of NaBH$_4$ are added in small portions until the solution turns to colorless, and the reaction mixture is stirred for several (e.g., 2) hours. The solvent is removed under vacuum and 50 mL of water added to the solution. The final product is extracted with 3 portions of dichloromethane, dried on MgSO$_4$, filtered and dried in vacuum. The crude product can be re-crystallized from a cold solvent (e.g., methanol) yielding the respective ligand precursor as a solid, typically in high to quantitative yields. Typically, no further purification steps are required.

In a typical such general procedure, ligand precursors having the general Formulae If were prepared:

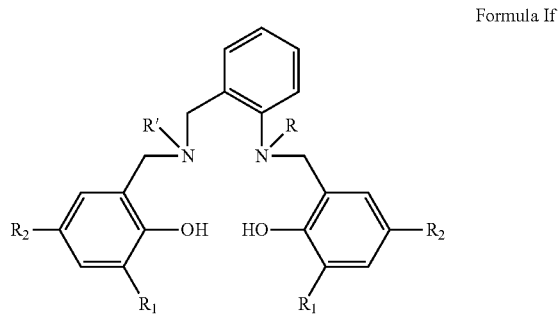

Formula If wherein R and R' are each alkyl, such that in Scheme 5 above, "m" is 2 and Ra denotes the R$_1$ and R$_2$ substituents.

Formula If corresponds to Formula I as described herein, in which R$_5$=R$_6$=R$_7$=R$_8$=H; Y=CH$_2$; Z=(CRaRb)(CRcRd) and Ra-Rd form together phenyl; R'=R=alkyl, preferably methyl, and R$_1$-R$_4$ are various combinations of substituents, as described hereinabove.

Using the above-described general procedure (see, Scheme 5), exemplary Salan ligand precursors having Formula 1f, which are referred to herein as Lig$^{30-32}$H$_2$ (see, FIG. 3) were prepared, as representative ligand precursors having a 3-carbon atoms bridging unit.

The following describes in detail the procedures used for preparing exemplary such ligand precursors.

Synthesis of N,N'-dimethyl-2-aminobenzylamine:

An exemplary N,N'-dialkyl-2-aminobenzylamine, a starting material in the general procedure depicted in Scheme 5 herein is N,N'-dimethyl-2-aminobenzylamine. This starting material was prepared as follows:

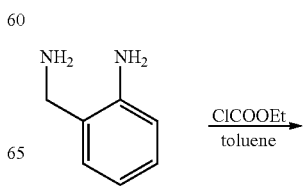

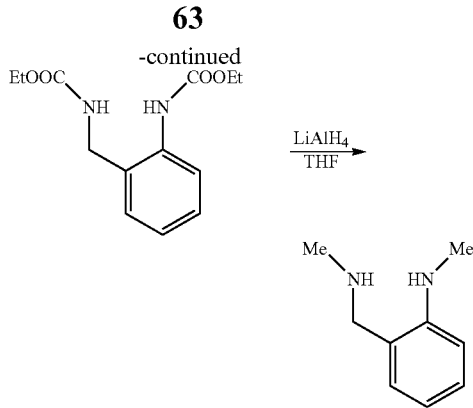

(a) 2-aminobenzylamine (0.26 gram, 2.1 mmol) was dissolved in toluene (50 mL) with slight warming until complete dissolution. Ethyl chloroformate (0.46 gram, 4.2 mmol) was added dropwise at room temperature. The reaction was stirred for 6 hours at room temperature, filtered, and the solvent was removed under vacuum to give 2-aminobenzylamine bis(ethylcarbamate) as a yellow viscous oil. Yield 0.25 gram (52%).

$^1$H NMR (400 MHz, CDCl$_3$): δ=8.41 (bs, 1H, NH), 7.86 (d, J=7.9 Hz, 1H, ArH), 7.31 (t, 1H, ArH), 7.18 (d, J=7.5 Hz, 1H, ArH), 7.06 (t, 1H, ArH), 4.29 (d, J=7.5 Hz, 2H, ArCH$_2$), 4.23 (q, 2H, OCH$_2$), 4.14 (q, 2H, OCH$_2$), 1.68 (bs, 1H, NH), 1.32 (t, 3H, CH$_3$), 1.23 (t, 3H, CH$_3$) ppm.

$^{13}$C NMR (100.63 MHz, CDCl$_3$): δ=154.6 (C), 139.4 (C), 130.6 (CH), 129.6 (CH), 124.4 (CH), 123.0 (CH), 61.9 (CH$_2$), 61.7 (CH$_2$), 42.1 (CH$_2$), 15.1 (CH$_3$), 15.0 (CH$_3$) ppm.

MS (FAB): calc. for C$_{13}$H$_{18}$N$_2$O$_4$: 266.3. found: 267.0 (MH$^+$).

(b) 2-aminobenzylamine bis(ethylcarbamate) (0.27 gram, 1.01 mmol) was dissolved in THF (50 mL) and the solution was cooled to 0° C. LiAlH$_4$ (0.27 gram, 6.11 mmol) was added in small portions to the solution. The mixture was stirred for 1 hour at room temperature and thereafter refluxed for 5 hours. The obtained gray cloudy solution was cooled to room temperature and approximately 1 gram of ice and 5 mL of NaOH (15%) were added thereto, and the resulting mixture was stirred overnight at room temperature. The mixture was thereafter filtered and the solid residue was extracted with hot THF (20 mL). The solvent was removed under vacuum to give a viscous brown oil. 10 mL of a 3M solution of HCl and 20 mL of dichloromethane were added and the aqueous phase was washed twice with dichloromethane. 15 mL of 10% solution of NaOH were added to the aqueous phase, and the solution was stirred for 20 minutes until cloudiness was observed. The aqueous phase was extracted thrice with 30 mL of dichloromethane. The organic phase was dried over MgSO$_4$ and the solvent was removed under vacuum to give 0.07 gram (0.48 mmol) of the N,N'-dimethyl-2-aminobenzylamine as a yellow oil in a final yield of 47%.

$^1$H NMR (400 MHz, CDCl$_3$): δ=7.19 (dt, J=7.8 Hz, J=1.5 Hz, 1H, ArH), 7.01 (d, J=6.9 Hz, 1H, ArH), 6.62 (m, 2H, ArH), 3.71 (s, 2H, ArCH$_2$), 2.82 (s, 3H, NCH$_3$), 2.39 (s, 3H, NCH$_3$) ppm.

$^{13}$C NMR (100.63 MHz, CDCl$_3$): δ=130.0 (CH), 128.7 (CH), 123.9 (C), 117.2 (C), 116.0 (CH), 109.3 (CH), 55.5 (CH$_2$), 36.3 (NCH$_3$), 30.2 (CH$_3$) ppm.

MS (FAB): calc. for C$_9$H$_{14}$N$_2$: 150.2. found: 151.1 (MH$^+$).

Preparation of Lig$^{30}$H$_2$ (see, FIG. 3 and Formula If wherein R$_1$=R$_2$=R$_3$=R$_4$=t-Bu):

N,N'-dimethyl-2-aminobenzylamine (0.58 gram, 3.8 mmol) was dissolved in THF (30 mL) and 0.8 gram of triethylamine was added to the solution. 2-(bromomethyl)-4,6-di-tert-butylphenol (2.30 gram, 7.6 mmol) dissolved in THF (20 mL) was added dropwise under an argon atmosphere. The mixture was stirred for 2 hours at room temperature, filtered, and the solvent was removed under vacuum. The yellow oil obtained was dissolved in dichloromethane (20 mL) and washed twice with water (20 mL each). The organic layer was dried over MgSO$_4$, filtered, and the filtrate was dried under vacuum to give a bright yellow powder. The crude product was crystallized from ice-cold methanol to give the final product with a yield of 75%.

$^1$H NMR (400 MHz, C$_6$D$_6$): δ=10.83 (bs, 2H, OH), 7.50 (s, 2H, ArH), 7.43 (dd, J=7.6, 1.6 Hz, 1H, ArH), 6.99-7.02 (m, 2H, ArH) 6.86-6.98 (m, 3H, ArH), 3.79 (s, 2H, CH$_2$), 3.59 (s, 2H, CH$_2$), 3.54 (s, 2H, CH$_2$), 2.18 (s, 3H, NCH$_3$), 2.09 (s, 3H, NCH$_3$), 1.68 (s, 9H, t-Bu), 1.67 (s, 9H, t-Bu), 1.37 (s, 9H, t-Bu), 1.35 (s, 9H, t-Bu) ppm.

$^{13}$C NMR (100.63 MHz, C$_6$D$_6$): δ=154.6 (CO), 154.3 (CO), 151.1 (C), 141.0 (C), 140.7 (C), 135.8 (C), 132.9 (C), 130.9 (CH), 128.1 (CH), 127.8 (C), 125.8 (CH), 123.9 (CH), 123.6 (CH), 123.3 (CH), 123.0 (CH), 121.8 (C), 121.1 (C), 120.9 (CH), 62.0 (CH$_2$), 61.6 (CH$_2$), 56.4 (CH$_2$), 43.0 (NCH$_3$), 41.2 (NCH$_3$), 35.0 (2C, C(CH$_3$)$_3$), 34.1 (2C, C(CH$_3$)$_3$), 31.7 (12C, C(CH$_3$)$_3$), 29.8 (12C C(CH$_3$)$_3$) ppm.

MS (FAB): calc. for C$_{39}$H$_{58}$N$_2$O$_2$: 586.9. found: 586.4.

Anal. Calc. For C$_{39}$H$_{58}$N$_2$O$_2$: C, 79.81; H, 9.96; N, 4.77. Found: C, 79.80; H, 10.15; N, 4.59.

Preparation of Lig$^{31}$H$_2$(see, FIG. 3 and Formula If wherein R$_1$=R$_3$=adamantyl; and R$_2$=R$_4$=methyl):

N,N'-dimethyl-2-aminobenzylamine (0.10 gram, 0.07 mmol) was dissolved in THF (30 mL) and 0.8 g triethylamine was added to the solution. 6-(1-Adamantyl)-2-(bromomethyl)-4-methylphenol (0.45 gram, 1.4 mmol) dissolved in THF (20 mL) was added dropwise under an argon atmosphere. The mixture was stirred for 2 hours at room temperature, filtered, and the solvent was removed under vacuum. The yellow oil obtained was dissolved in dichloromethane (20 mL) and washed twice with water (20 mL each). The organic layer was dried over MgSO$_4$, filtered, and the filtrate was dried under vacuum to give a white powder. The crude product was crystallized from ice-cold methanol to give final product with yield of 78%.

$^1$H NMR (400 MHz, C$_6$D$_6$): δ=10.6 (bs, 2H, OH), 7.31 (dd, J=7.6 Hz, 1H, ArH), 7.27-7.42 (m, 6H, ArH) 7.22-7.02 (m, 10H, ArH), 7.04-6.93 (m, 4H, ArH), 6.77-6.80 (m, 4H, ArH), 6.62-6.64 (m, 2H, ArH), 3.49 (s, 2H, CH$_2$), 3.25 (s, 2H, CH$_2$), 3.03 (s, 2H, CH$_2$), 1.91 (s, 3H, NCH$_3$), 1.85 (s, 6H, 2CH$_3$), 1.76 (s, 6H, 2CH$_3$), 1.75 (s, 6H, 2CH$_3$), 1.70 (s, 6H, 2CH$_3$), 1.69 (s, 3H, NCH$_3$) ppm.

$^{13}$C NMR (100.63 MHz, C$_6$D$_6$): δ=154.7 (CO), 153.5 (CO), 151.2 (C), 148.0 (C), 136.5 (C), 132.9 (C), 131.5 (CH), 131.2 (CH), 129.4 (C), 128.6 (CH), 127.9 (CH), 126.7 (CH), 125.7 (CH), 122.1 (C), 121.4 (C), 121.2 (CH), 116.3 (C), 110.2 (CH), 61.9 (C), 61.6 (C), 61.3 (CH), 59.1 (CH), 56.9 (CH$_2$), 42.6 (CH), 41.0 (CH$_2$), 40.6 (CH$_2$), 37.3 (C), 36.9 (CH3), 30.1 (C), 29.9 (C), 29.4 (CH$_3$), 20.7 (CH$_2$) ppm.

MS (FAB): calc. for C$_{45}$H$_{58}$N$_2$O$_2$: 658. found: 658.

Anal. Calc. For C$_{45}$H$_{58}$N$_2$O$_2$: C, 82.02; H, 8.87; N, 4.25. Found: C, 81.36; H, 8.99; N, 4.55.

Preparation of Lig$^{32}$H$_2$: (see, FIG. 3 and Formula If wherein R$_1$=R$_2$=R$_3$=R$_4$=cumyl):

N,N'-dimethyl-2-aminobenzylamine (0.20 gram, 1.3 mmol) was dissolved in THF (30 mL) and 0.8 gram triethylamine was added to the solution. 2-(bromomethyl)-4,6-bis(2-phenylpropan-2-yl)phenol (1.13 gram, 2.6 mmol) dissolved in THF (20 mL) was added dropwise under an argon atmosphere. The mixture was stirred for 2 hours at room temperature, filtered, and the solvent was removed under vacuum. The yellow oil obtained was dissolved in dichloromethane (20 mL) and was washed twice with water (20 mL each). The organic layer was dried over $MgSO_4$, filtered, and the solvent was removed under vacuum to give a bright yellow powder. The crude product was crystallized from ice-cold methanol to give the final product in a yield of 83%.

$^1$H NMR (400 MHz, $C_6D_6$): δ=10.2 (bs, 2H, OH), 7.51 (m, 2H, ArH), 7.27-7.42 (m, 6H, ArH) 7.22-7.02 (m, 10H, ArH), 7.04-6.93 (m, 4H, ArH), 6.77-6.80 (m, 4H, ArH), 6.62-6.64 (m, 2H, ArH), 3.49 (s, 2H, $CH_2$), 3.25 (s, 2H, $CH_2$), 3.03 (s, 2H, $CH_2$), 1.91 (s, 3H, $NCH_3$), 1.85 (s, 6H, $2CH_3$), 1.76 (s, 6H, $2CH_3$), 1.75 (s, 6H, $2CH_3$), 1.70 (s, 6H, $2CH_3$), 1.69 (s, 3H, $NCH_3$).

$^{13}$C NMR (100.63 MHz, $C_6D_6$): δ=154.2 (CO), 153.4 (CO), 151.6 (C), 151.5 (C), 151.4 (C), 151.3 (C), 150.4 (C), 140.6 (C), 140.2 (C), 135.6 (C), 135.4 (C), 135.2 (C), 132.6 (C), 131.3 (CH), 130.7 (CH), 128.0 (CH), 126.9 (CH), 126.8 (CH), 126.3 (CH), 126.0 (CH), 125.9 (CH), 125.8 (CH), 125.6 (CH), 125.6 (CH), 125.5 (CH), 125.0 (CH), 124.8 (CH), 124.5 (CH), 61.3 ($CH_2$), 60.2 ($CH_2$), 55.1 ($CH_2$), 42.8 ($NCH_3$), 42.6 (C), 42.2 (C), 42.0 (C), 40.4 ($NCH_3$), 31.2 (6C, $C(CH_3)_2$), 31.1 (6C, $C(CH_3)_2$), 30.2 (C), 29.4 (6C, $C(CH_3)_2$), 29.3 (6C, $C(CH_3)_2$).

MS (FAB): calc. for $C_{59}H_{66}N_2O_2$: 835. found: 835.

Anal. Calc. For $C_{59}H_{66}N_2O_2$: C, 84.85; H, 7.97; N, 3.35. Found: C, 84.23; H, 8.19; N, 3.37.

C. Syntheses of Ligand Precursors in which R and R' are Each Hydrogen:

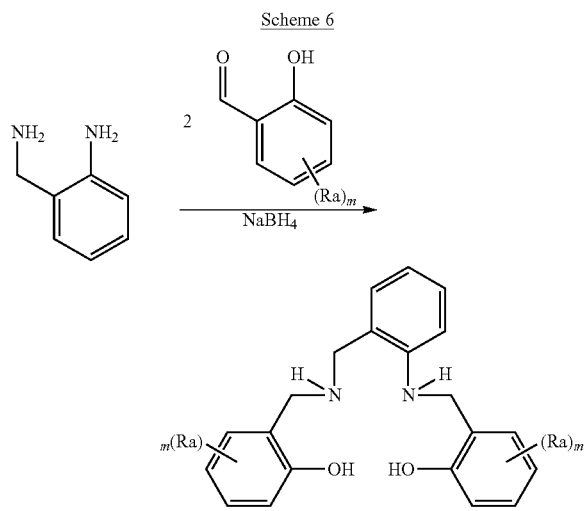

Scheme 6

In one exemplary general procedure, depicted in Scheme 6, 2-aminobenzylamine (1 molequivalent) is added to a solution of a substituted 2-hydroxy-benzaldehyde (2 molequivalent) in an organic solvent (e.g., methanol or ethanol) while the color of the reaction mixture typically turns to deep yellow. Approximately 10 molequivalents of $NaBH_4$ are added in small portions and the reaction mixture is stirred for 5 hours. The final product is filtered out, washed several times with water and dried on the air.

In a typical such general procedure, ligand precursors having the general Formulae Ig were prepared:

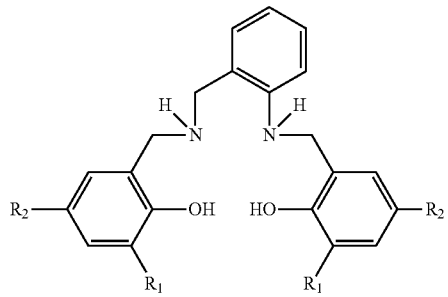

Formula Ig such that in Scheme 6 above, "m" is 2; R and R' are both hydrogen; and Ra denotes the $R_1$ and $R_2$ substituents.

Formula Ig corresponds to Formula I as described herein, in which $R_5$=$R_6$=$R_7$=$R_8$=H; Y=$CH_2$; Z=(CRaRb)(CRcRd) and Ra-Rd form together phenyl; R'=R=hydrogen, preferably methyl, and $R_1$-$R_4$ are various combinations of substituents, as described hereinabove.

Using the above-described general procedure (see, Scheme 6), exemplary Salan ligand precursors having Formula 1g, which are referred to herein as Lig$^{33-34}$H$_2$ (see, FIG. 3) were prepared, as representative ligand precursors having a 3-carbon atoms bridging unit.

The following describes in detail the procedures used for preparing exemplary such ligand precursors.

Preparation of Lig$^{33}$H$_2$ (see, FIG. 3 and Formula 1g wherein $R_1$=$R_2$=$R_3$=$R_4$=t-Bu):

A solution of 2-aminobenzylamine (0.26 gram, 2.1 mmol) in methanol (10 mL) was added to a solution of 3,5-di-tert-butyl-2-hydroxybenzaldehyde (0.98 gram, 4.2 mmol) in methanol (30 mL) and the reaction mixture was stirred for 1 hour. Approximately 10 equivalents of $NaBH_4$ were added by small portions until the orange solution turned to white and the reaction mixture was stirred for additional 5 hours. The final product was filtered, washed several times with water and dried on the air. Yield 1.17 gram (100%).

$^1$H NMR (CDCl$_3$, 400 MHz): δ=7.28 (d, 1H, J=2.3 Hz, ArH), 7.19 (d, 1H, J=2.3 Hz, ArH), 7.17 (m, 2H, ArH), 7.05 (d, 1H, J=2.1 Hz, ArH), 6.99-6.88 (m, 2H, ArH), 6.85 (d, 1H, J=2.1 Hz, ArH), 4.42 (d, 2H, J=5.7 Hz, $CH_2$), 3.96 (s, 2H, $CH_2$), 3.80 (s, 2H, $CH_2$), 1.40 (s, 9H, $(CH_3)_3$), 1.36 (s, 9H, $(CH_3)_3$), 1.30 (s, 9H, $(CH_3)_3$), 1.25 (s, 9H, $(CH_3)_3$) ppm.

$^{13}$C NMR (CDCl$_3$, 100.67 MHz): δ=154.1 (CO), 153.5 (CO), 154.6 (C), 141.8 (C), 140.9 (C), 136.3 (C), 136.1 (C), 130.3 (CH), 129.3 (CH), 125.8 (C), 123.9 (CH), 123.8 (CH), 123.3 (CH), 123.2 (CH), 122.4 (C), 121.7 (C), 120.6 (CH), 114.5 (CH), 53.5 ($CH_2$), 50.0 ($CH_2$), 49.2 ($CH_2$), 35.2 (C), 35.0 (C), 34.6 (C), 34.3 (C), 31.8 ($(CH_3)_3$), 31.7 ($(CH_3)_3$), 29.8 ($(CH_3)_3$), 29.7 ($(CH_3)_3$) ppm.

Preparation of Lig$^{34}$H$_2$ (see, FIG. 3 and Formula 1f wherein $R_1$=$R_2$=$R_3$=$R_4$=Cl):

A solution of 2-aminobenzylamine (0.45 gram, 3.7 mmol) in methanol (10 mL) was added to a solution of 3,5-dichloro-2-hydroxybenzaldehyde (1.40 gram, 7.3 mmol) in methanol (30 mL) and the reaction mixture was stirred for 1 hour. Approximately 10 equiv. of $NaBH_4$ were added by small portions until the orange solution turned to white and the reaction mixture was stirred for additional 5 hours. The final product was filtered, washed several times with water and dried on the air. Yield 1.71 gram (98%).

V. Syntheses of Ligand Precursors from the N-Methydiaminolbenzene Skeleton:

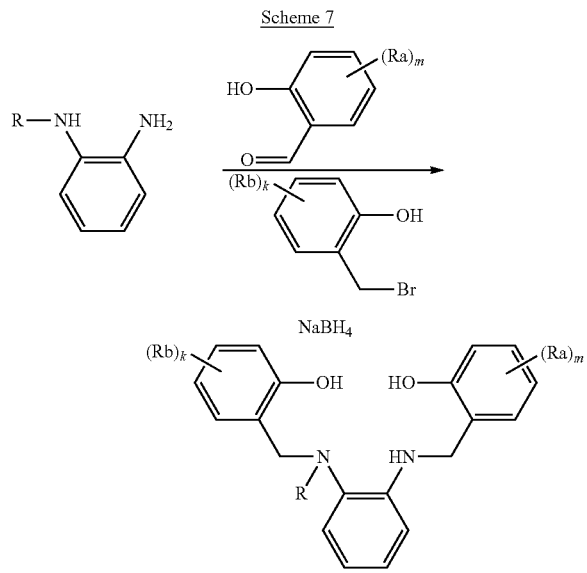

Scheme 7

In an exemplary general procedure, depicted in Scheme 7 hereinabove, $N^1$-alkylbenzene-1,2-diamine in an organic solvent such as benzene is added to a solution of a substituted 2-hydroxy-benzaldehyde in an organic solvent such as benzene and the reaction mixture is refluxed for several (e.g., 5) hours. The solution is then filtered and the solvent is removed under vacuum yielding a solid residue.

The obtained substituted 2-(iminomethyl)phenol is dissolved in THF, a base (e.g., triethylamine) is added, and to the obtained solution a solution of a substituted 2-(bromomethyl)phenol (1 molequivalent) in THF is added dropwise and the reaction mixture is stirred for several (e.g., 2) hours. The formed solid is thereafter filtered out and the solvent is removed under vacuum. The intermediate product is dissolved in methanol and 5 molequivalent of $NaBH_4$ are added in small portions until the solution turns to colorless, and the reaction mixture is stirred for several (e.g., 2) hours. The solvent is removed under vacuum and 50 mL of water added to the solution. The final product is extracted with 3 portions of dichloromethane, dried on $MgSO_4$, filtered and dried in vacuum. The crude product can be re-crystallized from a cold solvent (e.g., methanol) yielding the respective ligand precursor as a solid, typically in high to quantitative yields. Typically, no further purification steps are required.

In a typical such general procedure, ligand precursors having the following general Formula Ih were prepared:

Formula Ih

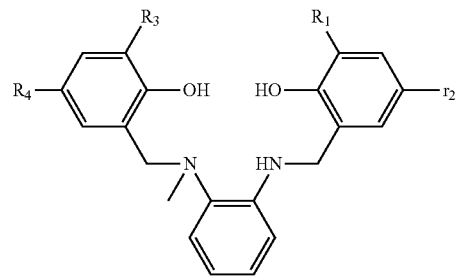

such that each of "k" and "m" in scheme 7 above is 2; Ra denotes the substituents $R_1$ and $R_2$; Rb denotes the substituents $R_3$ and $R_4$; and R is methyl.

Formula Ig corresponds to Formula I as described herein, in which $R_5=R_6=R_7=R_8=H$; Z and Y form together a phenyl; R'=H and R=alkyl, and $R_1$-$R_4$ are various combinations of substituents, as described hereinabove.

Using the above-described general procedure (see, Scheme 7), exemplary Salan ligand precursors having Formula Ig, which are referred to herein as $Lig^{35-36}H_2$ (see, FIG. 4) were prepared, as representative ligand precursors having a N-methyldiaminobenzene skeleton.

The following describes in detail the procedures used for preparing exemplary such ligand precursors.

Preparation of $Lig^{35}H_2$ (see, FIG. 4 and Formula 1h wherein $R_1=R_2=$t-Bu; and $R_3=R_4=$Cl):

(a) Synthesis of 2,4-di-tert-butyl-6-(((2-(methylamino)phenyl)imino)methyl)phenol: N-Methyl-1,2-phenylenediamine (0.58 gram, 4.7 mmol) was added to a solution of 3,5-di-tert-butyl-2-hydroxy-benzaldehyde (1.11 gram, 4.7 mmol) in benzene and the reaction mixture was refluxed for 2 hours. The solvent was removed under vacuum yielding a yellow solid. Yield: 1.61 gram (100%).

$^1$H NMR (CDCl$_3$, 400 MHz): δ=8.61 (s, 1H, NCH), 7.45 (d, 1H, J=2.2 Hz, ArH), 7.23 (d, 1H, J=2.2 Hz, ArH), 7.01 (m, 2H, ArH), 6.70 (m, 2H, ArH), 2.93 (s, 2H, NCH$_3$), 1.48 (s, 9H, (CH$_3$)$_3$), 1.33 (s, 9H, (CH$_3$)$_3$) ppm.

(b) A solution of 2-(bromomethyl)-4,6-dichlorophenol (0.72 gram, 2.8 mmol,) in THF (20 mL) was added dropwise to a solution of 2,4-di-tert-butyl-6-(((2-(methylamino)phenyl)imino)methyl)phenol (0.95 gram, 2.8 mmol) and triethylamine (3 mL) in THF (20 mL) and the reaction mixture was stirred for 2 hours. The solid that formed was filtered out and the solvent was removed under vacuum. The intermediate product was dissolved in methanol and 10 equivalents of $NaBH_4$ added by small portions until the solution turned to colorless and the mixture was stirred for 12 hours. The solvent was removed under vacuum and 50 mL of water was added to the solution. The final product was extracted with 3 portions of dichloromethane, dried on $MgSO_4$, filtered and dried in vacuum. Yield: 1.38 gram (96%).

$^1$H NMR (CDCl$_3$, 400 MHz): δ=7.29 (d, 1H, J=2.2 Hz, ArH), 7.28-7.09 (m, 3H, Hz, ArH), 7.06 (d, 1H, J=2.2 Hz, ArH), 6.97-6.59 (m, 3H, ArH), 4.38 (s, 2H, CH$_2$), 4.02 (s, 2H, CH$_2$), 2.58 (s, 3H, NCH$_3$), 1.40 (s, 9H, (CH$_3$)$_3$), 1.32 (s, 9H, (CH$_3$)$_3$) ppm.

Figure 4:
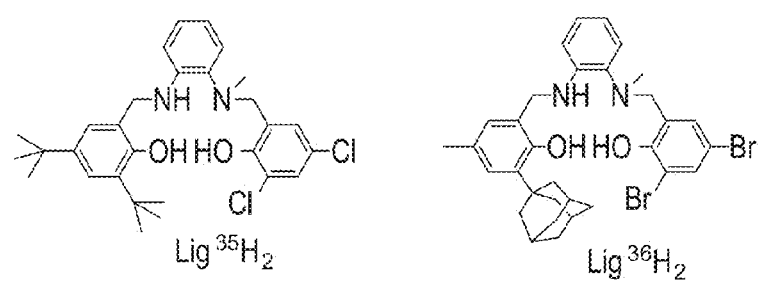
FIG. 4 presents the chemical structures of exemplary Salan ligand precursors according to some embodiments of the present invention, based on a 2-N-alkylaminoaniline skeleton (Lig$^{35-36}$H$_2$)

Preparation of $Lig^{36}H_2$ (see, FIG. 4 and Formula 1h wherein $R_1=$adamantly; $R_2=$methyl; $R_3=R_4=$Br):

(a) Synthesis of 2-adamantyl-4-methyl-6-(((2-(methylamino)phenyl)imino)methyl)phenol: N-Methyl-1,2-phenylenediamine (0.31 gram, 2.6 mmol) was added to a solution of 3-adamantyl-5-methyl-2-hydroxy-benzaldehyde (0.69 gram, 2.6 mmol) in benzene and the reaction mixture was refluxed for 2 hours. The solvent was removed under vacuum yielding a yellow solid. Yield: 0.90 gram (100%).

$^1$H NMR (CDCl$_3$, 400 MHz): δ=8.55 (s, 1H, NCH), 7.20-7.13 (m, 2H, ArH), 6.99 (d, 1H, J=1.4 Hz, ArH), 6.94 (d, 1H, J=1.4 Hz, ArH), 6.75-6.67 (m, 2H, ArH), 2.94 (s, 3H, NCH$_3$), 2.31 (s, 3H, CH$_3$), 2.19 (bs, 6H, Adamantyl), 2.09 (bs, 3H, Adamantyl), 1.80 (s, 6H, Adamantyl) ppm.

(b) A solution of 2-(bromomethyl)-4,6-dibromophenol (0.83 gram, 2.4 mmol,) in THF (20 mL) was added dropwise to a solution of 2-adamantyl-4-methyl-6-(((2-(methylamino)phenyl)imino)methyl)phenol (0.90 gram, 2.4 mmol) and triethylamine (3 mL) in THF (20 mL) and the reaction mixture was stirred for 2 hours. The solid that formed was filtered out and the solvent was removed under vacuum. The intermediate product was dissolved in methanol and 10 equivalents of NaBH$_4$ were added by small portions until the solution turned to colorless and the reaction mixture was stirred for 12 hours. The solvent was removed under vacuum and 50 mL of water added to the solution. The final product was extracted with 3 portions of dichloromethane, dried on MgSO$_4$, filtered and dried in vacuum. Yield 1.11 gram (72%).

$^1$H NMR (CDCl$_3$, 400 MHz): δ=7.51 (d, 1H, J=2.3 Hz, ArH), 7.13 (d, 1H, J=2.3 Hz, ArH), 7.07-7.03 (m, 2H, ArH), 6.99 (d, 1H, J=1.3 Hz, ArH), 6.89 (d, 1H, J=1.3 Hz, ArH), 6.87-6.83 (m, 2H, ArH), 4.35 (s, 2H, CH$_2$), 4.03 (s, 2H, CH$_2$), 2.59 (s, 3H, NCH$_3$), 2.29 (s, 3H, CH$_3$), 2.12 (bs, 6H, Adamantyl), 2.03 (bs, 3H, Adamantyl), 1.75 (s, 6H, Adamantyl) ppm.

Example 2

Synthesis of Metal Complexes

Group 4 metal complexes of various Salan ligands were synthesized by reacting the ligand precursors (e.g., those prepared as described in Example 1 hereinabove) with the appropriate metal (e.g., titanium, zirconium, or hafnium) reagent (referred to herein also as a metallic reagent) in an equimolar ratio as generally depicted in Scheme 8 below.

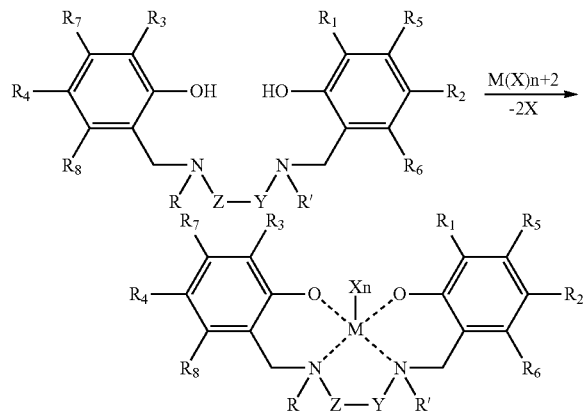

Scheme 8 wherein R$_1$-R$_8$ and R and R' are as defined herein; Z and Y together form a bridge between the two nitrogens, and can be, for example, ethylene, propylene, phenyl or benzyl, or can form with R a heterocyclic ring such as pyrrolidine; M is Hf, Zr or Ti; and X is a labile group, as defined herein, including, for example, Cl, O-iPr, O-tBu, benzyl (Bn), HNMe$_2$, etc.; and "n" is an integer, preferably being 1 or 2.

The formed complex depicted in Scheme 8 can include additional neutral ligands which are not presented in the structure.

Exemplary metallic reagents that can be used for obtaining the metal complexes include, without limitation, TiBn$_4$, Ti(O-iPr)$_4$, ZrBn$_4$, Zr(O-t-Bu)$_4$, HfBn$_4$, Hf(O-t-Bu)$_4$, etc, wherein Bn=benzyl (phenylmethyl); iPr=isopropyl; and t-Bu=tert-butyl.

A typical procedure for preparing the metal complexes described herein involves the addition of a solution of a ligand precursor as described herein in a common dry organic solvent (e.g., diethyl ether or toluene) to a solution of a metal reagent [M(X)n+2] in the same solvent, and stirring the reaction mixture at room temperature. After a time period ranging from several minutes to several hours, the organic solvent and the volatile by-products are removed under reduced pressure. The formed Salan complex can be purified by common methods including extractions and crystallizations.

All of the reactions for forming the metal complexes proceeded smoothly to give the desired complexes in high to quantitative yields.

Additional Salan metal complexes were synthesized, purified and characterized according to the methodology described herein, by combining any of the herein described metallic reagents [M(X)n+2]. The exceptionally broad series of metal complexes was prepared in a relatively short time, while not relying on automated high-throughput methods. The ability to synthesize such a broad variety of well-defined Salan complexes gives evidence to the applicability of the Salan ligands, and to their selective binding to metals.

Following are exemplary procedures for the synthesis, work-up, and characterization of various metal complexes of Salan ligands according to some embodiments of the present invention. All other metal complexes were similarly prepared and their structure was verified by NMR measurements.

Preparation of Lig$^1$TiBn$_2$ (see, Formula II wherein R$_1$=R$_2$=R$_3$=R$_4$=t-Bu; R$_5$=R$_6$=R$_7$=R$_8$=H; Z=Y=CH$_2$; R'=H; R=methyl; and Q=TiBn$_2$)

Lig$^1$H$_2$ (44 mg, 0.09 mmol) was dissolved in about 1 mL of toluene and was added dropwise to a stirring red solution of TiBn$_4$ (36 mg, 0.09 mmol) in about 1 mL of toluene. The color of the solution changed to dark red-brown. The reaction mixture was stirred for 1-2 minutes and the solvent was removed under vacuum yielding a brown solid, which was washed with about 1 mL of pentane and dried under vacuum. The final yield was 54 mg (83%).

$^1$H NMR (C$_6$D$_6$, 400 MHz): δ=7.54 (d, 1H, J=4.3 Hz, ArH), 7.61 (s, 1H, ArH), 7.30 (d, 1H, J=4.3 Hz, ArH), 7.24-7.13 (m, 6H, ArH), 7.03-7.6.92 (m, 5H, Hz, ArH), 3.45 (d, J=18.3 Hz, 1H), 3.32 (d, J=18.3 Hz, 1H), 3.15 (d, J=14.0 Hz, 1H), 3.03 (d, J=14.0 Hz, 1H), 2.99 (d, J=17.5 Hz, 1H), 2.69 (d, J=17.5 Hz, 1H), 2.19 (s, 3H, NCH$_3$), 1.85 (s, 9H, (CH$_3$)$_3$), 1.48 (s, 27H, 3(CH$_3$)$_3$), 1.45-1.33 (m, 4H, CH$_2$) ppm.

$^{13}$C NMR (C$_6$D$_6$, 100.67 MHz): δ=164.7 (CO), 158.2 (CO), 147.1 (C), 144.7 (C), 143.8 (C), 143.1 (CH), 141.8 (C), 137.4 (C), 136.0 (C), 131.9 (C), 129.4 (CH), 129.3 (CH), 129.0 (CH), 128.46 (CH), 126.1 (CH), 125.5 (CH), 124.7 (CH), 124.2 (CH), 123.6 (C), 122.5 (CH), 122.7 (CH), 64.7 (CH$_2$), 62.2 (CH$_2$), 56.7 (CH$_2$), 53.5 (CH$_2$), 38.0 (CH$_2$), 36.6 (CH$_2$), 35.8 (C), 34.8 (C), 34.3 (C), 34.2 (C), 31.8 (C(CH$_3$)$_3$), 31.7 (C(CH$_3$)$_3$), 30.9 (C(CH$_3$)$_3$), 30.6 (C(CH$_3$)$_3$), 21.2 (NCH$_3$) ppm.

Preparation of Lig$^1$ZrBn$_2$ (see, Formula II wherein R$_1$=R$_2$=R$_3$=R$_4$=t-Bu; R$_5$=R$_6$=R$_7$=R$_8$=H; Z=Y=CH$_2$; R'=H; R=methyl; and Q=ZrBn$_2$):

Lig$^1$H$_2$ (45 mg, 0.09 mmol) was dissolved in about 1 mL of cold toluene and the solution was added dropwise to a stirring orange solution of ZrBn$_4$ (40 mg, 0.09 mmol) in about 1 mL of cold toluene. The reaction mixture was stirred for 2 hours and the solvent was thereafter removed under vacuum, yielding a yellow solid, which was washed with about 1 mL of pentane and dried under vacuum. The final yield was 66 mg (96%).

Preparation of Lig$^1$HfBn$_2$ (see, Formula II wherein R$_1$=R$_2$=R$_3$=R$_4$=t-Bu; R$_5$=R$_6$=R$_7$=R$_8$=H; Z=Y=CH$_2$; R'=H; R=methyl; and Q=HfBn$_2$):

Lig¹H₂ (22 mg, 0.04 mmol) was dissolved in about 1 mL of cold toluene and the solution was added dropwise to a stirring solution of HfBn₄ (23 mg, 0.04 mmol) in about 1 mL of cold toluene. The reaction mixture was stirred for 2 hours and the solvent was thereafter removed under vacuum, yielding a white solid, which was washed with about 1 mL of pentane and dried under vacuum. The final yield was 36 mg (98%).

Preparation of Lig¹Ti(OiPr)₂ (see, Formula II wherein $R_1=R_2=R_3=R_4=$t-Bu; $R_5=R_6=R_7=R_8=$H; $Z=Y=CH_2$; R'=H; R=methyl; and Q=Ti(OiPr₂):

Lig¹H₂ (68 mg, 0.13 mmol) was dissolved in about 1 mL of diethyl ether and the solution was added dropwise to a stirring solution of Ti(OiPr)₄ (38 mg, 0.13 mmol) in about 1 mL of diethyl ether. The reaction mixture was stirred for 2 hours and the solvent was thereafter removed under vacuum, yielding a white solid, which was washed with about 1 mL of pentane and dried under vacuum. The final yield was 94 mg (99%).

Preparation of Lig²TiBn₂ (see, Formula II wherein $R_1=R_2=R_3=R_4=$Cl; $R_5=R_6=R_7=R_8=$H; $Z=Y=CH_2$; R'=H; R=methyl; and Q=TiBn₂):

Lig²H₂ (29 mg, 0.07 mmol) was dissolved in about 1 mL of toluene and was added dropwise to a stirring red solution of TiBn₄ (28 mg, 0.09 mmol) in about 1 mL of toluene. The color of the solution changed to dark red-brown. The reaction mixture was stirred for 1-2 minutes and the solvent was removed under vacuum yielding a brown solid, which was washed with ca. 1 mL of pentane and dried under vacuum. The final yield was 40 mg (91%).

Preparation of Lig²HfBn₂ (see, Formula II wherein $R_1=R_2=R_3=R_4=$Cl; $R_5=R_6=R_7=R_8=$H; $Z=Y=CH_2$; R'=H; R=methyl; and Q=HfBn₂):

Lig²H₂ (40 mg, 0.09 mmol) was dissolved in about 1 mL of cold toluene and the solution was added dropwise to a stirring solution of HfBn₄ (52 mg, 0.09 mmol) in about 1 mL of cold toluene. The reaction mixture was stirred for 2 hours and the solvent was thereafter removed under vacuum, yielding a white solid, which was washed with about 1 mL of pentane and dried in vacuo. The final yield was 55 mg (90%).

¹H NMR (C₆D₆, 400 MHz): δ=7.37 (d, 1H, J=3.8 Hz, ArH), 7.30-7.26 (m, 4H, ArH), 7.01-7.6.88 (m, 6H, ArH), 6.45 (d, 1H, J=3.9 Hz, ArH), 3.56 (d, 1H, J=7.7 Hz, ArH), 3.45 (d, J=11.6 Hz, 1H), 3.36 (d, J=10.7 Hz, 1H), 2.92 (d, J=7.7 Hz, 1H), 2.39 (d, J=7.3 Hz, 1H), 2.33 (d, J=7.3 Hz, 1H), 2.19 (d, J=10.7 Hz, 1H), 1.81 (d, J=11.6 Hz, 1H), 1.49 (s, 3H, NCH₃), 1.35-1.11 (m, 4H, CH₂) ppm.

Preparation of Lig²Ti(OiPr)₂ (see, Formula II wherein $R_1=R_2=R_3=R_4=$Cl; $R_5=R_6=R_7=R_8=$H; $Z=Y=CH_2$; R'=H; R=methyl; and Q=Ti(OiPr₂):

Lig²H₂ (39 mg, 0.09 mmol) was dissolved in about 1 mL of diethyl ether and the solution was added dropwise to a stirring solution of Ti(OiPr)₄ (26 mg, 0.09 mmol) in about 1 mL of diethyl ether. The reaction mixture was stirred for 2 hours and the solvent was thereafter removed under vacuum, yielding a white solid, which was washed with about 1 mL of pentane and dried in vacuo. The final yield was 56 mg (100%).

¹H NMR (C₆D₆, 400 MHz): δ=7.38 (s, 1H, ArH), 7.30 (s, 1H, ArH), 6.65 (s, 1H, ArH), 6.59 (s, 1H, ArH), 5.26 (septet, 1H, J=4.1 Hz, OCH), 4.94 (septet, 1H, J=4.94 Hz, OCH), 4.30 (d, J=12.3 Hz, 1H), 4.23 (d, J=10.5 Hz, 1H), 2.59 (d, J=12.3 Hz, 1H), 2.48 (d, J=10.5 Hz, 1H), 2.08 (m, 2H, NCH), 1.94 (s, 3H, NCH₃), 1.78 (m, 2H, NCH), 1.34 (d, J=4.1 Hz, 3H, OCH(CH₃)₂), 1.27-1.24 (m, 9H, OCH(CH₃)₂) ppm.

Figure 5:
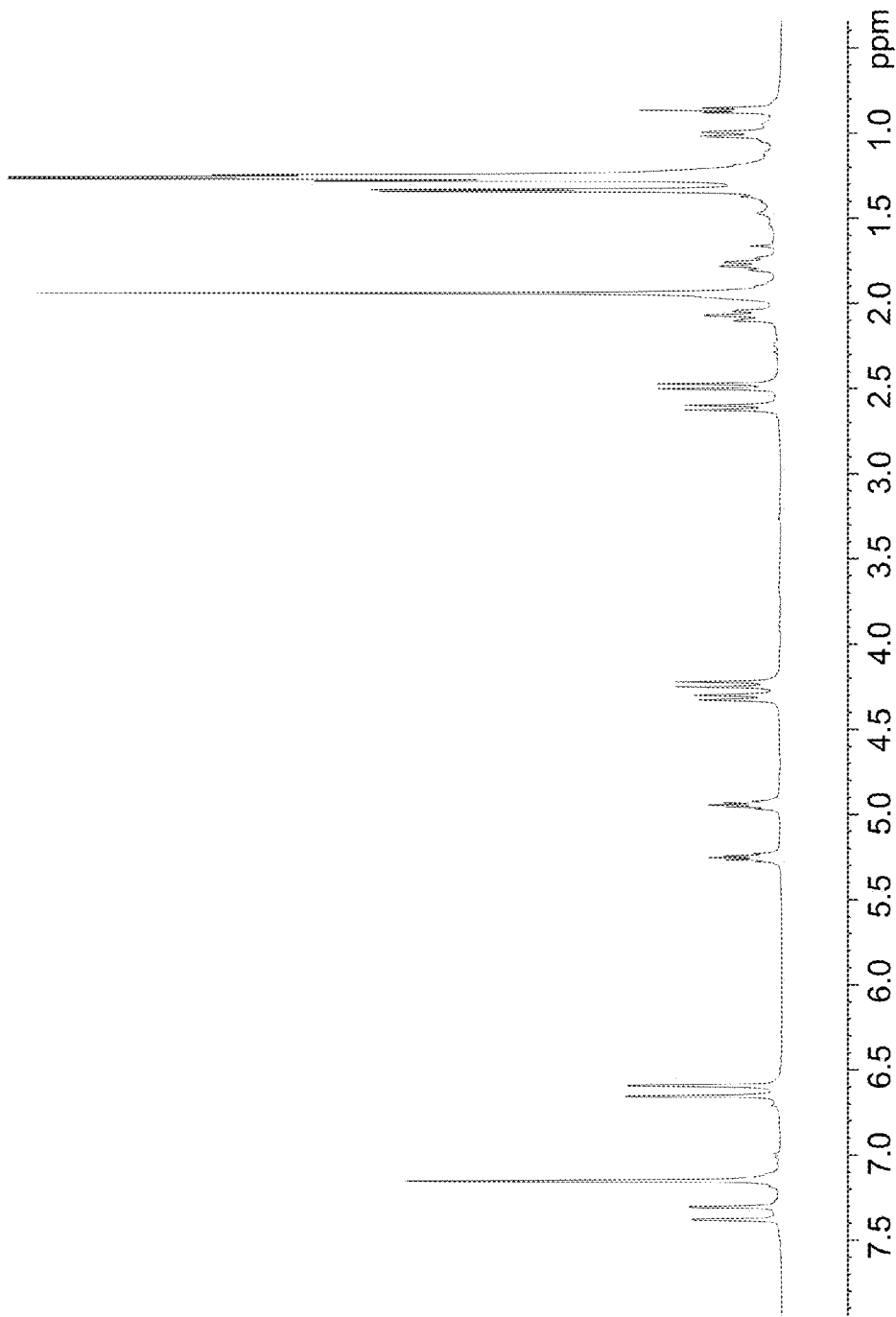
FIG. 5 presents an $^1$H-NMR spectrum of Lig$^2$Ti(OiPr)$_2$, illustrating the formation of a single diastereoisomer.

The ¹H NMR spectrum of Lig²Ti(OiPr)₂ is presented in FIG. 5, and clearly shows the formation of a single diastereomer, thus demonstrating a selective wrapping mode of the Salan ligand around the metal center.

Preparation of Lig²Hf(OtBu)₂ (see, Formula II wherein $R_1=R_2=R_3=R_4=$Cl; $R_5=R_6=R_7=R_8=$H; $Z=Y=CH_2$; R'=H; R=methyl; and Q=Hf(Ot-Bu₂):

Lig²H₂ (32 mg, 0.08 mmol) was dissolved in about 1 mL of diethyl ether and the solution was added dropwise to a stirring solution of Hf(OtBu)₄ (36 mg, 0.08 mmol) in about 1 mL of diethyl ether. The reaction mixture was stirred for 2 hours and the solvent was thereafter removed under vacuum, yielding a white solid, which was washed with about 1 mL of pentane and dried in vacuo. The final yield was 47 mg (84%).

¹H NMR (C₆D₆, 400 MHz): δ=7.39 (d, J=2.7 Hz, 1H, ArH), 7.34 (d, J=2.7 Hz, 1H, ArH), 6.61 (d, J=2.7 Hz, 1H, ArH), 6.58 (d, J=2.7 Hz, 1H, ArH), 4.31 (d, 1H, J=11.9 Hz, CH), 4.27 (d, 1H, J=11.9 Hz, CH), 2.58 (d, J=17.7 Hz, 1H, CH), 2.40 (d, J=17.7 Hz, 1H), 1.98 (s, 3H, NCH₃), 1.46 (s, 9H, OC(CH₃)₃), 1.41 (s, 9H, OC(CH₃)₃), 1.24-1.03 (m, 4H, NCH₂CH₂N) ppm.

Preparation of Lig³TiBn₂ (see, Formula II wherein $R_1=R_2=R_3=R_4=$I; $R_5=R_6=R_7=R_8=$H; $Z=Y=CH_2$; R'=H; R=methyl; and Q=TiBn₂):

Lig³H₂ (40 mg, 0.05 mmol) was dissolved in about 1 mL of toluene and was added dropwise to a stirring red solution of TiBn₄ (21 mg, 0.05 mmol) in about 1 mL of toluene. The color of the solution changed to dark red-brown. The reaction mixture was stirred for 1-2 minutes and the solvent was removed under vacuum yielding a brown solid, which was washed with about 1 mL of pentane and dried in vacuo. The final yield was 38 mg (74%).

Preparation of Lig⁴TiBn₂ (see, Formula II wherein $R_1=R_2=$t-Bu; $R_3=R_4=$Cl; $R_5=R_6=R_7=R_8=$H; $Z=Y=CH_2$; R'=H; R=methyl; and Q=TiBn₂):

Lig⁴H₂ (46 mg, 0.10 mmol) was dissolved in about 1 mL of toluene and was added dropwise to a stirring red solution of TiBn₄ (41 mg, 0.10 mmol) in about 1 mL of toluene. The color of the solution changed to dark red-brown. The reaction mixture was stirred for 1-2 minutes and the solvent was removed under vacuum yielding a brown solid, which was washed with about 1 mL of pentane and dried in vacuo. The final yield was 65 mg (94%).

¹H NMR (C₆D₆, 400 MHz): δ=7.45-7.43 (m, 2H, ArH), 7.14-7.09 (m, 3H, Hz, ArH), 7.07-7.01 (m, 4H, Hz, ArH), 7.00-6.97 (m, 5H, ArH), 5.67 (d, J=17.6 Hz, 1H), 4.83 (d, J=17.6 Hz, 1H), 3.68 (d, J=18.2 Hz, 1H), 3.30 (d, J=10.4 Hz, 1H), 2.84 (d, J=11.7 Hz, 1H), 2.47 (d, J=11.7 Hz, 1H), 2.24 (d, J=18.2 Hz, 1H), 2.04-2.01 (m, 2H, CH₂), 1.96 (d, J=10.4 Hz, 1H), 1.76 (s, 9H, (CH₃)₃), 1.72 (s, 3H, NCH₃), 1.53-1.49 (m, 2H, CH₂), 1.36 (s, 9H, (CH₃)₃) ppm.

¹³C NMR (C₆D₆, 100.67 MHz): δ=157.6 (CO), 155.6 (CO), 148.3 (C), 144.8 (C), 142.9 (C), 141.7 (CH), 137.7 (C), 135.5 (C), 132.1 (C), 129.1 (C), 129.5 (CH), 129.2 (CH), 128.7 (CH), 128.4 (CH), 127.8 (CH), 127.0 (CH), 126.1 (CH), 125.5 (CH), 122.0 (C), 122.2 (CH), 121.7 (CH), 71.5 (CH₂), 62.6 (CH₂), 59.3 (CH₂), 58.2 (CH₂), 57.5 (CH₂), 43.9 (CH₂), 35.4 (C), 34.5 (C), 31.8 (C(CH₃)₃), 30.4 (C(CH₃)₃), 21.3 (NCH₃) ppm.

Preparation of Lig⁴Ti(OiPr)₂ (see, Formula II wherein $R_1=R_2=$t-Bu; $R_3=R_4=$Cl; $R_5=R_6=R_7=R_8=$H; $Z=Y=CH_2$; R'=H; R=methyl; and Q=Ti(OiPr₂)):

Lig⁴H₂ (42 mg, 0.09 mmol) was dissolved in about 1 mL of diethyl ether and the solution was added dropwise to a stirring solution of Ti(OiPr)₄ (26 mg, 0.09 mmol) in about 1 mL of diethyl ether. The reaction mixture was stirred for 2 hours and the solvent was thereafter removed under vacuum, yielding a white solid, which was washed with about 1 mL of pentane and dried in vacuo. The final yield was 52 mg (87%).

$^1$H NMR (C$_6$D$_6$, 400 MHz): δ=7.50 (d, 1H, J=2.4 Hz, ArH), 7.44 (d, 1H, J=4.1 Hz, ArH), 6.92 (d, 1H, J=2.4 Hz, ArH), 6.68 (d, 1H, J=4.1 Hz, ArH), 5.38 (septet, 1H, J=6.1 Hz, OCH), 4.77 (septet, 1H, J=6.1 Hz, OCH), 4.55 (d, J=13.7 Hz, 1H), 4.25 (d, J=14.1 Hz, 1H), 3.13 (d, J=13.7 Hz, 1H), 2.51 (d, J=14.1 Hz, 1H), 2.32-2.13 (m, 4H, NCH), 1.99 (s, 3H, NCH$_3$), 1.67 (s, 9H, CH$_3$), 1.35 (s, 9H, CH$_3$), 1.29 (d, J=6.0 Hz, 3H, OCH(CH$_3$)$_2$), 1.27 (d, J=6.0 Hz, 3H, OCH(CH$_3$)$_2$), 1.21 (d, J=6.0 Hz, 3H, OCH(CH$_3$)$_2$), 1.12 (d, J=6.0 Hz, 3H, OCH(CH$_3$)$_2$) ppm.

$^{13}$C NMR (C$_6$D$_6$, 100.67 MHz): δ=158.7 (CO), 157.9 (CO), 139.6 (C), 136.0 (C), 128.6 (CH), 127.2 (CH), 124.7 (C), 123.8 (CH), 123.4 (C), 123.1 (CH), 122.3 (C), 119.6 (C), 78.0 (OCH), 77.3 (OCH), 63.5 (CH$_2$), 53.7 (NCH$_3$), 46.9 (CH$_2$), 43.6 (CH$_2$), 35.3 (CH$_2$), 34.1 (C), 34.0 (C), 31.6 (C(CH$_3$)$_3$), 30.3 (C(CH$_3$)$_3$), 26.3 (CH$_3$), 26.1 (CH$_3$), 26.0 (CH$_3$), 25.9 (CH$_3$) ppm.

Preparation of Lig$^7$ZrBn$_2$ (see, Formula II wherein R$_1$=adamantyl; R$_2$=methyl; R$_3$=R$_4$=Cl; R$_5$=R$_6$=R$_7$=R$_8$=H; Z=Y=CH$_2$; R'=H; R=methyl; and Q=ZrBn$_2$):

Lig$^7$H$_2$ (63 mg, 0.13 mmol) was dissolved in about 1 mL of cold toluene and the solution was added dropwise to a stirring orange solution of ZrBn$_4$ (57 mg, 0.13 mmol) in about 1 mL of cold toluene. The reaction mixture was stirred for 2 hours and the solvent was thereafter removed under vacuum, yielding a yellow solid, which was washed with about 1 mL of pentane and dried in vacuo. The final yield was 90 mg (89%).

$^1$H NMR (C$_6$D$_6$, 400 MHz): δ=7.37 (d, J=3.8 Hz, 1H, ArH), 7.32 (d, J=2.9 Hz, 1H, ArH), 7.14-7.06 (m, 2H, ArH), 7.01-6.95 (m, 3H, Hz, ArH), 6.92-6.90 (m, 4H, Hz, ArH), 6.41 (d, J=2.9 Hz, 1H, ArH), 6.32 (d, J=3.8 Hz, 1H, ArH), 4.01 (d, J=14.4 Hz, 1H, ArH), 3.23 (d, J=10.1 Hz, 1H), 2.65 (d, J=14.4 Hz, 1H), 2.51 (d, J=8.7 Hz, 1H), 2.36 (d, J=8.7 Hz, 1H), 2.28 (d, J=10.9 Hz, 1H), 2.17 (s, 3H, CH$_3$), 2.11-2.01 (m, 9H, Adamantyl), 1.97 (d, J=10.1 Hz, 1H), 1.94-1.87 (m, 3H, Adamantyl), 1.84 (d, J=10.1 Hz, 1H), 1.80-1.77 (m, 6H, Adamantyl), 1.72 (s, 3H, NCH$_3$), 1.37-1.35 (m, 2H, CH$_2$), 0.86-0.82 (m, 2H, CH$_2$) ppm.

Preparation of Lig$^8$Ti(OiPr)$_2$ (see, Formula II wherein R$_1$=adamantyl; R$_2$=methyl; R$_3$=R$_4$=Br; R$_5$=R$_6$=R$_7$=R$_8$=H; Z=Y=CH$_2$; R'=H; R=methyl; and Q=Ti(OiPr)$_2$):

Lig$^8$H$_2$ (37 mg, 0.06 mmol) was dissolved in about 1 mL of diethyl ether and the solution was added dropwise to a stirring solution of Ti(OiPr)$_4$ (18 mg, 0.06 mmol) in about 1 mL of diethyl ether. The reaction mixture was stirred for 2 hours and the solvent was thereafter removed under vacuum, yielding a white solid, which was washed with about 1 mL of pentane and dried in vacuo. The final yield was 52 mg (100%).

Crystal data for C$_{39}$H$_{56}$Br$_2$N$_2$O$_4$Ti; M=824.58; triclinic; space group P-1; a=9.9820(2), b=14.9970(3), c=15.1630(3) Å; α=109.1590(11)°, β=107.2940(9)°, λ=100.0220(10)°; V=1952.21(7) Å$^3$; Z=2; Dc=1.403 g cm$^{-3}$; μ(Mo—Kα)=2.306 mm$^{-1}$; T=110(2) K; No. of data collected 8889; R1=0.0388 and wR2=0.0957 for 7178 reflections with I>2σ (I); R1=0.0539 and wR2=0.1039 for all reflections.

Figure 6:
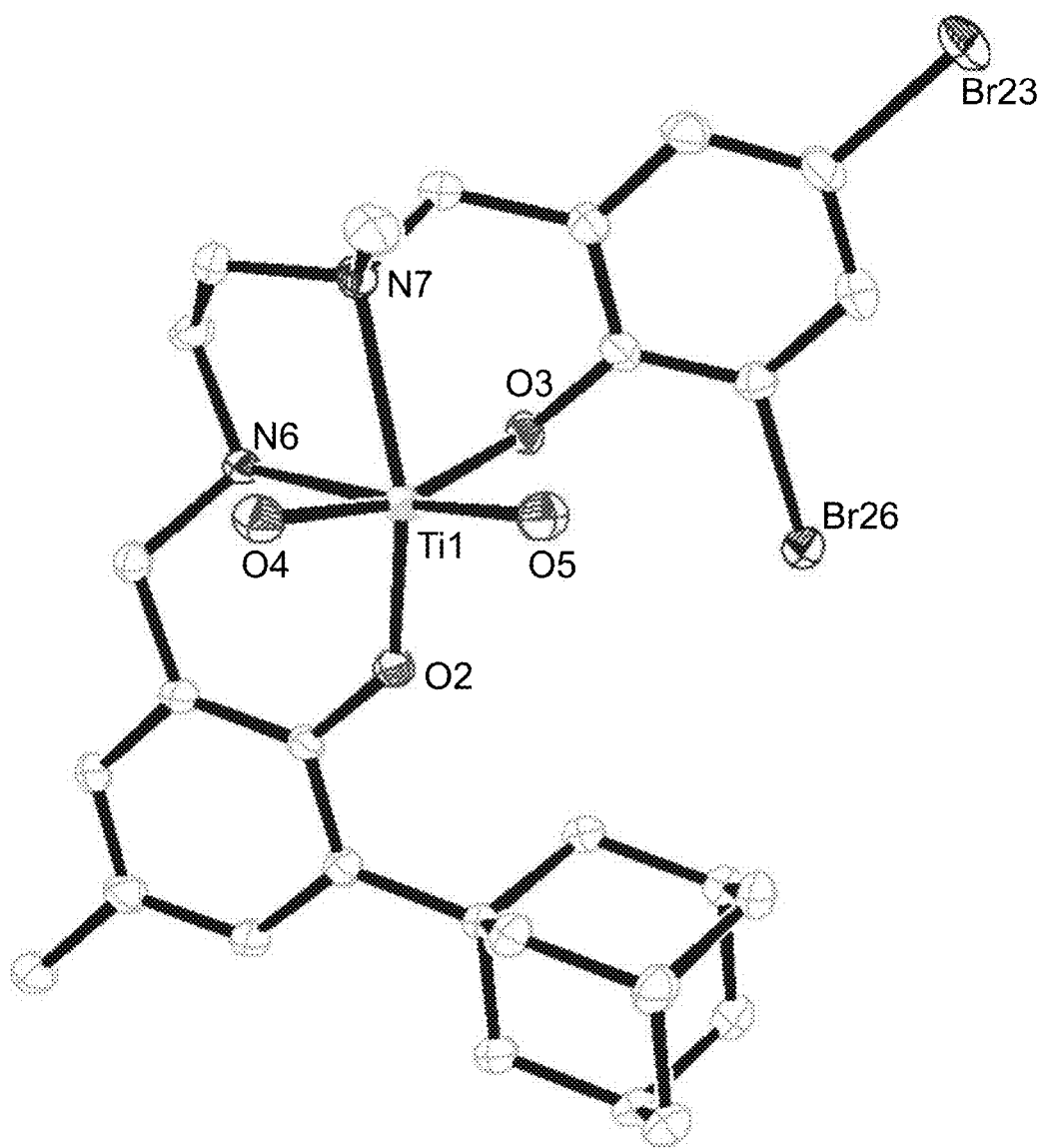
FIG. 6 presents an ORTEP representation of [TiLig$^3$(O-iPr)$_2$] (with iPr groups omitted for clarity), illustrating the fac-mer Salan wrapping and the cis relationship between the labile groups.

FIG. 6 presents the ORTEP representation of Lig$^8$Ti(O-i-Pr)$_2$, obtained by single-crystal X-ray diffraction measurements, illustrating the fac-mer Salan wrapping and the cis relationship between the labile groups. Isopropyl groups of O-i-Pr (X) bound to Ti (M) are omitted for clarity.

Preparation of Lig$^{12}$HfBn$_2$ (see, Formula II wherein R$_1$=R$_2$=I; R$_3$=adamantyl; R$_4$=methyl; R$_5$=R$_6$=R$_7$=R$_8$=H; Z=Y=CH$_2$; R'=H; R=methyl; and Q=HfBn$_2$):

Lig$^{12}$H$_2$ (51 mg, 0.08 mmol) was dissolved in about 1 mL of cold toluene and the solution was added dropwise to a stirring solution of HfBn$_4$ (41 mg, 0.08 mmol) in about 1 mL of cold toluene. The reaction mixture was stirred for 2 hours and the solvent was thereafter removed under vacuum, yielding a white solid, which was washed with about 1 mL of pentane and dried in vacuo. The final yield was 80 mg (100%).

$^1$H NMR (C$_6$D$_6$, 400 MHz): δ=8.01 (d, J=2.0 Hz, 1H, ArH), 7.26 (d, J=2.0 Hz, 1H, ArH), 7.23-7.04 (m, 2H, ArH), 7.01-6.97 (m, 3H, Hz, ArH), 6.96 (d, J=1.3 Hz, 1H, ArH), 6.91 (d, J=1.3 Hz, 1H, ArH), 5.12 (d, J=13.9 Hz, 1H, ArH), 3.96 (d, J=16.6 Hz, 1H), 3.61 (d, J=16.6 Hz, 1H), 3.30 (d, J=13.9 Hz, 1H), 2.87 (d, J=10.6 Hz, 1H), 2.71 (d, J=10.6 Hz, 1H), 2.63 (d, J=11.6 Hz, 1H), 2.44 (s, 3H, CH$_3$), 2.26 (d, J=11.6 Hz, 1H), 2.16-1.81 (m, 15H, Adamantyl), 1.66 (s, 3H, CH$_3$), 1.40-1.15 (m, 4H, CH$_2$) ppm.

Preparation of Lig$^{12}$Ti(OiPr)$_2$ (see, Formula II wherein R$_1$=R$_2$=I; R$_3$=adamantyl; R$_4$=methyl; R$_5$=R$_6$=R$_7$=R$_8$=H; Z=Y=CH$_2$; R'=H; R=methyl; and Q=Ti(OiPr$_2$)):

Lig$^{12}$H$_2$ (45 mg, 0.08 mmol) was dissolved in about 1 mL of diethyl ether and the solution was added dropwise to a stirring solution of Ti(OiPr)$_4$ (22 mg, 0.08 mmol) in about 1 mL of diethyl ether. The reaction mixture was stirred for 2 hours and the solvent was thereafter removed under vacuum, yielding a white solid, which was washed with about 1 mL of pentane and dried in vacuo. The final yield was 56 mg (96%).

Preparation of Lig$^{18}$TiBn$_2$ (see, Formula II wherein R$_1$=adamantyl; R$_2$=methyl; R$_3$=R$_4$=Cl; R$_5$=R$_6$=R$_7$=R$_8$=H; Y=CH$_2$; Z and R form pyrrolidine; R'=H; and Q=TifBn$_2$):

Lig$^{18}$H$_2$ (87 mg, 0.17 mmol) was dissolved in about 1 mL of toluene and was added dropwise to a stirring red solution of TiBn$_4$ (68 mg, 0.17 mmol) in about 1 mL of toluene. The color of the solution changed to dark red-brown. The reaction mixture was stirred for 1-2 hours and the solvent was removed under vacuum yielding a brown solid, which was washed with about 1 mL of pentane and dried in vacuo. The final yield was 97 mg (78%).

$^1$H NMR (C$_6$D$_6$, 400 MHz): δ=7.51 (d, J=3.5 Hz, 1H, ArH), 7.47 (d, J=4.5 Hz, 1H, ArH), 7.25-7.18 (m, 5H, ArH), 7.15-7.95 (m, 5H, ArH), 5.75 (d, J=15.5 Hz, 1H), 5.43 (d, J=15.5 Hz, 1H), 3.65 (d, J=12.0 Hz, 1H), 3.59 (d, J=12.0 Hz, 1H), 3.49 (d, J=9.3 Hz, 1H), 3.18 (d, J=9.3 Hz, 1H), 2.99 (d, J=12.0 Hz, 1H), 2.89-2.72 (m, 4H, CH$_2$), 2.67 (d, J=12.0 Hz, 1H), 2.54 (s, 3H, CH$_3$), 2.44-2.14 (m, 15H, Adamantyl), 1.78 (m, 1H, CH$_2$), 1.27 (m, 1H, CH$_2$), 0.93 (m, 1H, CH$_2$), 1.06 (m, 1H, CH$_2$), 0.72 (m, 1H, CH$_2$) ppm.

$^{13}$C NMR (C$_6$D$_6$, 100.67 MHz): δ=159.0 (CO), 156.7 (CO), 147.3 (C), 145.0 (C), 142.2 (C), 141.8 (CH), 136.3 (C), 135.9 (C), 132.2 (C), 129.9 (CH), 129.3 (CH), 128.4 (CH), 125.7 (CH), 124.7 (CH), 122.5 (C), 122.3 (C), 76.0 (CH$_2$), 70.1 (CH$_2$), 64.0 (CH), 60.4 (CH$_2$), 56.5 (CH$_2$), 54.1 (CH$_2$), 45.7 (CH$_2$), 41.3 (CH$_2$, Adamantyl), 37.2 (CH$_2$, Adamantyl), 30.4 (CH, Adamantyl), 29.3 (C, Adamantyl), 24.1 (CH$_2$), 21.5 (CH$_3$) ppm.

Preparation of Lig$^{19}$TiBn$_2$ (see, Formula II wherein R$_1$=adamantyl; R$_2$=methyl; R$_3$=R$_4$=Br;

$R_5=R_6=R_7=R_8=H$; $Y=CH_2$; Z and R form together pyrrolidine; R'=H; and $Q=TiBn_2$):

Lig$^{19}$H$_2$ (97 mg, 0.16 mmol) was dissolved in about 1 mL of toluene and was added dropwise to a stirring red solution of TiBn$_4$ (65 mg, 0.16 mmol) in about 1 mL of toluene. The color of the solution changed to dark red-brown. The reaction mixture was stirred for 1-2 minutes and the solvent was removed under vacuum yielding a brown solid, which was washed with about 1 mL of pentane and dried in vacuo. The final yield was 118 mg (89%).

$^1$H NMR (C$_6$D$_6$, 400 MHz): δ=7.74 (s, 1H, ArH), 7.70 (s, 1H, ArH), 7.19-7.06 (m, 5H, ArH), 6.99-6.91 (m, 5H, ArH), 6.71 (s, 1H, ArH), 6.62 (s, 1H, ArH), 5.63 (d, J=14.7 Hz, 1H), 5.34 (d, J=14.7 Hz, 1H), 3.58 (d, J=16.1 Hz, 1H), 3.52 (d, J=16.1 Hz, 1H), 3.35 (d, J=12.1 Hz, 1H), 3.06 (d, J=12.1 Hz, 1H), 2.89 (d, J=12.0 Hz, 1H), 2.80 (d, J=12.0 Hz, 1H), 2.61-2.56 (m, 3H, CH$_2$), 2.45 (s, 3H, CH$_3$), 2.33-2.16 (m, 15H, Adamantyl), 2.04-2.01 (m, 4H, CH$_2$), 1.16 (m, 1H, CH$_2$), 0.85 (m, 1H, CH$_2$) ppm.

$^{13}$C NMR (C$_6$D$_6$, 100.67 MHz): δ=158.7 (CO), 157.1 (CO), 147.5 (C), 145.1 (C), 141.8 (C), 135.2 (CH), 132.1 (C), 130.7 (C), 130.4 (C), 129.8 (CH), 129.3 (CH), 128.7 (CH), 128.3 (CH), 126.1 (CH), 125.3 (C), 122.5 (C), 75.8 (CH$_2$), 73.9 (CH$_2$), 63.4 (CH), 60.4 (CH$_2$), 57.3 (CH$_2$), 53.6 (CH$_2$), 45.4 (CH$_2$), 41.3 (CH$_2$, Adamantyl), 37.4 (CH$_2$, Adamantyl), 30.2 (CH, Adamantyl), 29.1 (C, Adamantyl), 24.6 (CH$_2$), 21.1 (CH$_3$) ppm.

Preparation of Lig$^{20}$TiBn$_2$ (see, Formula II wherein R$_1$=adamantyl; R$_2$=methyl; R$_3$=R$_4$=I; R$_5$=R$_6$=R$_7$=R$_8$=H; Y=CH$_2$; Z and R form together pyrrolidine; R'=H; and Q=TiBn$_2$):

Lig$^{20}$H$_2$ (74 mg, 0.10 mmol) was dissolved in about 1 mL of toluene and was added dropwise to a stirring red solution of TiBn$_4$ (43 mg, 0.10 mmol) in about 1 mL of toluene. The color of the solution changed to dark red-brown. The reaction mixture was stirred for 1-2 minutes and the solvent was removed under vacuum yielding a brown solid, which was washed with about 1 mL of pentane and dried in vacuo. The final yield was 81 mg (83%).

$^1$H NMR (C$_6$D$_6$, 400 MHz): δ=7.54-7.51 (m, 2H, ArH), 7.03-6.92 (m, 5H, ArH), 6.89-6.78 (m, 7H, ArH), 5.46 (d, J=13.9 Hz, 1H), 5.31 (d, J=13.9 Hz, 1H), 3.58 (d, J=16.3 Hz, 1H), 3.51 (d, J=16.3 Hz, 1H), 3.29 (d, J=12.7 Hz, 1H), 3.11 (d, J=12.7 Hz, 1H), 2.81 (d, J=10.8 Hz, 1H), 2.73 (d, J=10.8 Hz, 1H), 2.69-2.560 (m, 3H, CH$_2$), 2.45 (s, 3H, CH$_3$), 2.39-2.11 (m, 15H, Adamantyl), 2.01-1.96 (m, 4H, CH$_2$), 1.03 (m, 1H, CH$_2$), 0.94 (m, 1H, CH$_2$) ppm.

$^{13}$C NMR (C$_6$D$_6$, 100.67 MHz): δ=154.9 (CO), 153.1 (CO), 146.6 (C), 145.1 (C), 141.3 (C), 138.5 (CH), 132.0 (C), 131.7 (C), 130.1 (C), 129.9 (CH), 129.5 (CH), 128.9 (CH), 128.3 (CH), 126.1 (CH), 124.8 (C), 113.8 (C), 74.8 (CH$_2$), 73.2 (CH$_2$), 63.4 (CH), 59.4 (CH$_2$), 57.3 (CH$_2$), 50.7 (CH$_2$), 58.2 (CH$_2$), 41.4 (CH$_2$, Adamantyl), 37.4 (CH$_2$, Adamantyl), 30.1 (CH, Adamantyl), 29.9 (C, Adamantyl), 23.8 (CH$_2$), 22.1 (CH$_3$) ppm.

Preparation of Lig$^{24}$TiBn$_2$ (see, Formula II wherein R$_1$=R$_2$=t-Bu; R$_3$=R$_4$=Cl; R$_5$=R$_6$=R$_7$=R$_8$=H; Y=CH$_2$; Z and R for together pyrrolidine; R'=H; and Q=TiBn$_2$):

Lig$^{24}$H$_2$ (38 mg, 0.08 mmol) was dissolved in about 1 mL of toluene and was added dropwise to a stirring red solution of TiBn$_4$ (32 mg, 0.08 mmol) in about 1 mL of toluene. The color of the solution changed to dark red-brown. The reaction mixture was stirred for 1-2 minutes and the solvent was removed under vacuum yielding a brown solid, which was washed with about 1 mL of pentane and dried under vacuum. The final yield was 53 mg (96%).

$^1$H NMR (C$_6$D$_6$, 400 MHz): δ=7.39 (s, 1H, ArH), 7.26-7.21 (m, 2H, ArH), 7.13-7.11 (m, 2H, Hz, ArH), 7.05-6.97 (m, 6H, ArH), 6.89 (m, 2H, ArH), 6.54 (s, 1H, ArH), 5.79 (d, J=15.7 Hz, 1H), 5.32 (d, J=15.2 Hz, 1H), 3.59 (d, J=15.7 Hz, 1H), 3.51 (d, J=15.2 Hz, 1H), 3.41 (d, J=7.3 Hz, 1H), 3.13 (d, J=7.3 Hz, 1H), 2.92 (d, J=14.6 Hz, 1H), 2.81 (d, J=14.6 Hz, 1H), 1.86-1.82 (m, 3H, CH$_2$), 1.65 (s, 9H, (CH$_3$)$_3$), 1.52-1.47 (m, 2H, CH$_2$), 1.37 (s, 9H, (CH$_3$)$_3$), 1.34 (s, 9H, (CH$_3$)$_3$), 1.32 (s, 9H, (CH$_3$)$_3$), 1.31-1.18 (m, 2H, CH$_2$), 1.06 (m, 1H, CH$_2$), 0.72 (m, 1H, CH$_2$) ppm.

$^{13}$C NMR (C$_6$D$_6$, 100.67 MHz): δ=158.8 (CO), 156.3 (CO), 147.5 (C), 142.8 (C), 141.8 (CH), 135.2 (C), 131.9 (C), 130.2 (C), 129.6 (C), 128.6 (CH), 128.4 (CH), 127.4 (CH), 127.1 (CH), 126.0 (CH), 122.4 (CH), 121.9 (C), 121.6 (C), 74.1 (CH$_2$), 69.3 (CH$_2$), 62.7 (CH), 61.8 (CH$_2$), 57.4 (CH$_2$), 53.4 (CH$_2$), 38.1 (NCH$_3$), 35.2 (C), 34.4 (C), 31.7 (C(CH$_3$)$_3$), 30.3 (C(CH$_3$)$_3$) ppm.

Preparation of Lig$^{30}$HfBn$_2$ (see, Formula II wherein R$_1$=R$_2$=R$_3$=R$_4$=t-bu; R$_5$=R$_6$=R$_7$=R$_8$=H; Z and Y form together benzyl; R'=R=methyl; and Q=HfBn$_2$):

Lig$^{30}$H$_2$ (36 mg, 0.06 mmol) was dissolved in about 1 mL of cold toluene and the solution was added dropwise to a stirring solution of HfBn$_4$ (33 mg, 0.06 mmol) in about 1 mL of cold toluene. The reaction mixture was stirred for 2 hours and the solvent was thereafter removed under vacuum, yielding a white solid, which was washed with about 1 mL of pentane and dried in vacuo. The final yield was 57 mg (100%).

Preparation of Lig$^{30}$Zr(OtBu)$_2$ (see, Formula II wherein R$_1$=R$_2$=R$_3$=R$_4$=t-bu; R$_5$=R$_6$=R$_7$=R$_8$=H; Z and Y form together benzyl; R'=R=methyl; and Q=Zr(OtBu)$_2$):

To a stirring colorless solution of Zr(O-tert-Bu)$_4$ (29 mg, 0.076 mmol) in 2 mL of ether was added dropwise Lig$^{30}$H$_2$ (44 mg, 0.076 mmol) in ether (2 mL) at room temperature. White solid appeared immediately, and the reaction was allowed to stir for 2 hours. The solvent was removed under vacuum, and the resulting yellow solid was washed with 2 mL of pentane and dried under vacuum. The final yield was 54 mg (86%, 0.067 mmol).

$^1$H NMR (400 MHz, C$_6$D$_6$) δ 7.58 (d, J=2.4 Hz, 1H), 7.52 (d, J=2.4 Hz, 1H), 7.13 (d, J=2.8 Hz, 1H), 7.1-7.03 (m, 2H), 6.89-6.87 (m, 2H), 6.83 (d, J=1.6 Hz, 1H), 5.76 (d, J=11.6 Hz, 1H, AB system), 5.23 (d, J=15.6 Hz, 1H, AB system), 4.38 (d, J=12.8 Hz, 1H, AB system), 3.05 (s, 3H, NMe), 2.83 (d, J=12.4 Hz, 1H, AB system), 2.71 (d, J=13.2 Hz, 1H, AB system), 2.59 (d, J=12.8 Hz, 1H, AB system), 1.99 (s, 3H, NMe), 1.77 (s, 9H), 1.65 (s, 9H), 1.41 (s, 9H), 1.37 (s, 9H), 1.17 (s, 9H), 0.84 (s, 9H) ppm.

$^{13}$C NMR (100.63 MHz, C$_6$D$_6$) δ 161.8 (CO), 158.7 (CO), 151.8 (C), 139.2 (C), 137.8 (C), 136.2 (C), 136.1 (C), 135.1 (CH), 129.9 (CH), 129.5 (CH), 128.9 (CH), 125.3 (CH), 124.7 (C), 124.6 (C), 123.7 (CH), 123.6 (CH), 122.1 (C), 119.4 (CH), 77.1 (C), 76.9 (CH$_2$), 76.2 (C), 74.3 (CH$_2$), 68.4 (CH$_2$), 65.7 (CH$_2$), 63.4 (CH$_2$), 44.2 (NMe), 42.6 (NMe), 35.3 (C), 35.0 (C), 34.0 (C), 33.9 (C), 33.2 (t-Bu), 32.4 (t-Bu), 31.9 (t-Bu), 31.7 (t-Bu), 30.8 (t-Bu), 30.4 (t-Bu) ppm.

Anal. Calc. for C$_{47}$H$_{74}$N$_2$O$_4$Zr: C, 68.65; H, 9.07; N, 3.41. Found: C, 69.49; H, 9.17; N, 3.83.

Crystal data for C$_{47}$H$_{74}$N$_2$O$_4$Zr; M=822.30; triclinic; space group P-1; a=13.1983(3), b=13.6046(3), c=15.0395(5) Å; β=67.6226(9)°; V=2375.97(11) Å$^3$; Z=2; Dc=1.149 g cm$^{-3}$; μ(Mo—Kα)=0.272 mm$^{-1}$; T=110(2) K; No. of data collected 8970; R1=0.0493 and wR2=0.1052 for 6347 reflections with I>2σ (I); R1=0.0803 and wR2=0.1154 for all reflections.

Figure 7:
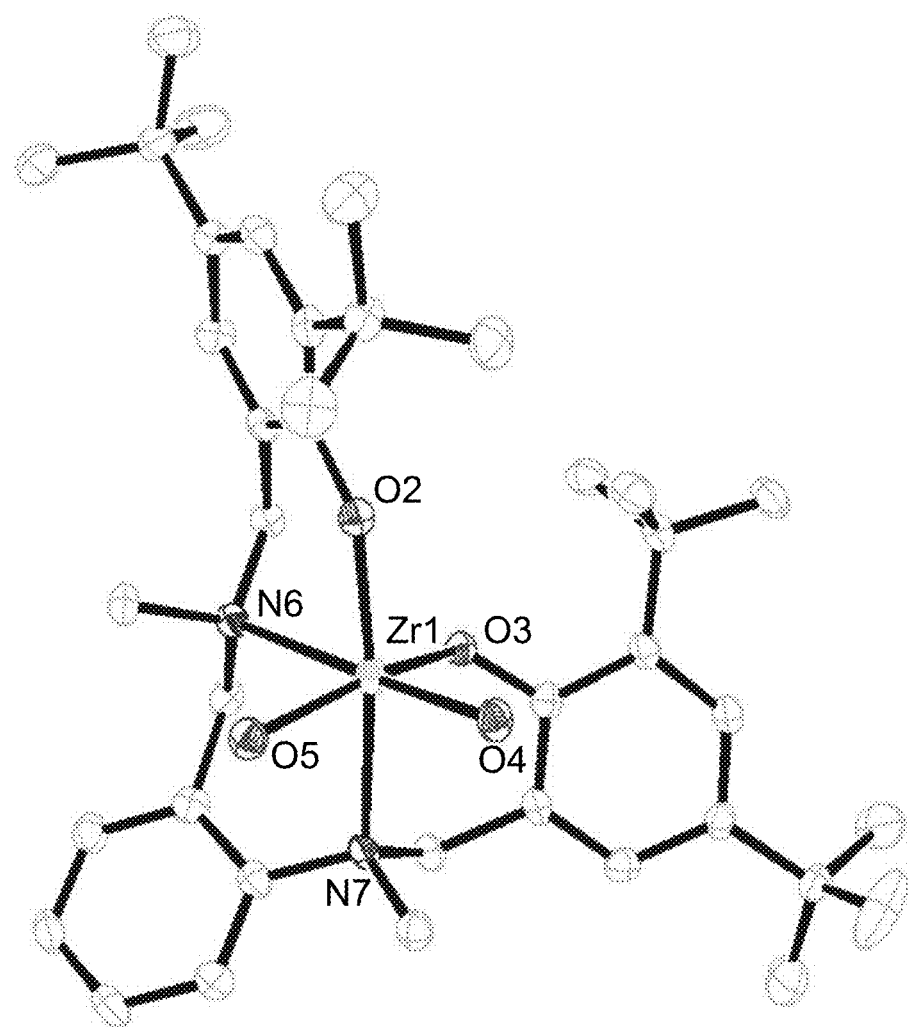
FIG. 7 presents an ORTEP representation of Lig$^{30}$Zr(O-tBu)$_2$ (with t-butyl groups of O-tBu bound to Zr omitted for clarity), illustrating the fac-mer Salan wrapping and the cis relationship between the labile groups.

FIG. 7 presents the ORTEP representation of Lig$^{30}$Zr(OtBu)$_2$, obtained by single-crystal X-ray diffraction measurements, illustrating the fac-mer Salan wrapping and the cis relationship between the labile groups. Tert-butyl groups of O-t-Bu (X) bound to Zr (M) are omitted for clarity.

Preparation of Lig$^{30}$Hf(OtBu)$_2$ (see, Formula II wherein $R_1=R_2=R_3=R_4$=t-bu; $R_5=R_6=R_7=R_8$=H; Z and Y form together benzyl; R'=R=methyl; and Q=Hf(OtBu)$_2$):

To a stirring colorless solution of Hf(O-tert-Bu)$_4$ (20 mg, 0.042 mmol) in 2 mL of ether was added dropwise Lig$^{30}$H$_2$ (25 mg, 0.042 mmol) in ether (2 mL) at room temperature. White solid appeared immediately, and the reaction was allowed to stir for 2 hours. The solvent was removed under vacuum, and the resulting yellow solid was washed with 2 mL of pentane and dried under vacuum. The final yield was 27 mg (74%, 0.030 mmol).

$^1$H NMR (400 MHz, C$_6$D$_6$): δ=7.60 (d, J=2.5 Hz, 1H), 7.53 (d, J=2.5 Hz, 1H), 7.11 (d, J=2.5 Hz, 1H), 7.08-7.03 (m, 2H), 6.91-6.85 (m, 2H), 6.82 (d, J=2.4 Hz, 1H), 5.78 (d, J=13.6 Hz, 1H, AB system), 5.24 (d, J=12.8 Hz, 1H, AB system), 4.42 (d, J=13.6 Hz, 1H, AB system), 3.05 (s, 3H, NMe), 2.83 (d, J=12.8 Hz, 1H, AB system), 2.74 (d, J=12.8 Hz, 1H, AB system), 2.60 (d, J=12.8 Hz, 1H, AB system), 2.02 (s, 3H, NMe), 1.77 (s, 9H), 1.63 (s, 9H), 1.41 (s, 9H), 1.37 (s, 9H), 1.17 (s, 9H), 0.85 (s, 9H) ppm.

$^{13}$C NMR (100.63 MHz, C$_6$D$_6$): δ=161.7 (CO), 158.6 (CO), 151.8 (C), 139.1 (C), 137.9 (C), 136.8 (C), 136.6 (C), 134.9 (CH), 129.8 (CH), 129.5 (CH), 127.9 (CH), 125.4 (CH), 124.5 (C), 124.4 (C), 123.7 (CH), 123.5 (CH), 122.2 (C), 119.4 (CH), 76.1 (C), 74.0 (C), 68.5 (CH$_2$), 65.9 (CH$_2$), 63.5 (NMe), 44.6 (NMe), 43.1 (CH$_2$), 35.3 (C), 34.9 (C), 33.9 (C), 33.8 (C), 33.1 (t-Bu), 32.6 (t-Bu), 31.8 (t-Bu), 31.7 (t-Bu), 30.9 (t-Bu), 30.6 (t-Bu) ppm.

Preparation of Lig$^{31}$Zr(OtBu)$_2$ (see, Formula II wherein $R_1=R_3$=adamantyl; $R_2=R_4$=methyl; $R_5=R_6=R_7=R_8$=H; Z and Y form together benzyl; R'=R=methyl; and Q=Zr(OtBu)$_2$):

To a stirring colorless solution of Zr(O-tert-Bu)$_4$ (40 mg, 0.104 mmol) in 2 mL of ether was added dropwise Lig$^{31}$H$_2$ (69 mg, 0.104 mmol) in ether (2 mL) at room temperature. After 2 hours the solvent was removed under vacuum, and the resulting white solid was washed with 2 mL of pentane and dried under vacuum. The final yield was 71 mg (82%, 0.079 mmol).

$^1$H NMR (400 MHz, C$_6$D$_6$): δ=7.20 (m, 2H), 7.08 (m, 2H), 6.81-6.77 (m, 2H), 6.69-6.62 (m, 2H), 5.80 (d, J=18.8 Hz, 1H, AB system), 5.21 (d, J=18.8 Hz, 1H, AB system), 4.85 (d, J=16.0 Hz, 1H, AB system), 4.43 (d, J=14.8 Hz, 1H, AB system), 3.82 (d, J=14.8 Hz, 1H, AB system), 3.11 (s, 3H, NMe), 2.78 (d, J=16.0 Hz, 1H, AB system), 2.52-2.29 (m, 12H, Adamantyl), 2.46, (s, 3H, NMe), 2.28 (s, 3H, Me), 2.21-2.12 (m, 6H, Adamantyl), 2.08 (s, 3H, Me), 1.90-1.81 (m, 6H, Adamantyl), 1.37-1.35 (m, 3H, Adamantyl), 1.21 (s, 9H, O-t-Bu), 1.00 (m, 3H, Adamantyl), 0.95 (s, 9H, O-t-Bu) ppm.

$^{13}$C NMR (100.63 MHz, C$_6$D$_6$): δ=161.8 (CO), 158.6 (CO), 151.8 (C), 147.3 (C), 137.7 (C), 137.3 (C), 137.1 (C), 135.0 (C), 131.6 (CH), 129.6 (CH), 126.1 (CH), 125.3 (CH), 125.0 (CH), 124.1 (CH), 123.7 (CH), 122.7 (C), 122.2 (CH), 119.4 (CH), 76.4 (C), 74.4 (C), 67.7 (CH$_2$), 66.4 (CH$_2$), 66.1 (CH$_2$), 63.4 (C), 58.2 (CH$_2$), 47.3 (CH$_3$), 43.8 (C), 42.8 (CH), 41.7 (CH$_2$), 40.9 (CH$_2$), 40.8 (CH$_2$), 37.4 (CH$_2$), 37.3 (CH$_2$), 37.0 (CH$_2$), 33.4 (C), 32.9 (CH$_3$), 32.4 (CH$_3$), 30.9 (CH), 29.6 (CH$_3$), 29.3 (CH$_3$), 20.9 (CH$_3$) ppm.

Preparation of Lig$^{31}$Hf(OtBu)$_2$ (see, Formula II wherein $R_1=R_3$=adamantyl; $R_2=R_4$=methyl; $R_5=R_6=R_7=R_8$=H; Z and Y form together benzyl; R'=R=methyl; and Q=Hf(OtBu)$_2$):

To a stirring colorless solution of Hf(O-tert-Bu)$_4$ (34 mg, 0.072 mmol) in 2 mL of ether was added dropwise Lig$^{31}$H$_2$ (47 mg, 0.072 mmol) in ether (2 mL) at room temperature. After 2 hours the solvent was removed under vacuum, and the resulting white solid was washed with 2 mL of pentane and dried under vacuum. The final yield was 64 mg (91%, 0.065 mmol).

$^1$H NMR (400 MHz, C$_6$D$_6$): δ=7.23 (m, 2H), 7.09-7.03 (m, 2H), 6.80-6.76 (m, 2H), 6.70-6.62 (m, 2H), 5.81 (d, J=13.6 Hz, 1H, AB system), 5.22 (d, J=13.2 Hz, 1H, AB system), 4.85 (d, J=12.8 Hz, 1H, AB system), 4.47 (d, J=13.2 Hz, 1H, AB system), 3.89 (d, J=13.2 Hz, 1H, AB system), 3.10 (s, 3H, NMe), 2.79 (s, 3H, NMe), 2.76 (d, J=9.6 Hz, 1H, AB system), 2.54-2.37 (m, 12H, Adamantyl), 2.37 (s, 3H, Me), 2.33 (s, 3H, Me), 2.23-2.00 (m, 6H, Adamantyl), 1.66 (m, 6H, Adamantyl), 1.32 (m, 3H, Adamantyl), 1.22 (s, 9H, O-t-Bu), 1.02 (m. 3H, Adamantyl), 0.96 (s, 9H, O-t-Bu) ppm.

$^{13}$C NMR (100.63 MHz, C$_6$D$_6$): δ=160.4 (CO), 159.3 (CO), 152.4 (C), 147.8 (C), 139.0 (C), 138.5 (C), 138.2 (C), 135.4 (C), 132.2 (CH), 130.3 (CH), 126.0 (CH), 125.5 (CH), 125.0 (C), 124.6 (CH), 124.2 (CH), 123.5 (C), 123.2 (CH), 120.2 (CH), 76.7 (C), 75.7 (C), 68.4 (CH$_2$), 67.0 (CH$_2$), 66.3 (CH$_2$), 64.2 (C), 59.1 (CH$_2$), 48.3 (CH$_3$), 44.9 (C), 43.9 (CH), 42.4 (CH$_2$), 41.6 (CH$_2$), 41.5 (CH$_2$), 38.0 (CH$_2$), 37.9 (CH$_2$), 37.6 (CH$_2$), 34.7 (C), 33.8 (CH$_3$), 33.4 (CH$_3$), 31.7 (CH), 30.2 (CH$_3$), 30.1 (CH$_3$), 29.9 (CH$_3$), 21.5 (CH) ppm.

Preparation of Lig$^{32}$Zr(OtBu)$_2$ (see, Formula II wherein $R_1=R_2=R_3=R_4$=cumyl; $R_5=R_6=R_7=R_8$=H; Z and Y form together benzyl; R'=R=methyl; and Q=Zr(OtBu)$_2$):

To a stirring colorless solution of Zr(O-tert-Bu)$_4$ (54 mg, 0.141 mmol) in 2 mL of ether was added dropwise Lig$^{32}$H$_2$ (117 mg, 0.141 mmol) in ether (2 mL) at room temperature. After 2 hours the solvent was removed under vacuum, and the resulting white solid was washed with 2 mL of pentane and dried under vacuum. The final yield was 118 mg (79%, 0.110 mmol).

$^1$H NMR (400 MHz, C$_6$D$_6$): δ=7.61 (d, J=2.4 Hz, 1H), 7.59 (m, 2H), 7.46-7.39 (m, 5H), 7.30-7.21 (m, 6H), 7.15-7.08 (m, 6H), 6.94-6.81 (m, 10H), 6.72 (dd, J=7.6 Hz, 1.6 Hz, 1H), 6.69 (d, J=2.8 Hz, 1H), 6.65 (d, J=2.4 Hz, 1H), 4.45 (d, J=12.7 Hz, 1H, AB system), 3.90 (d, J=13.5 Hz, 1H, AB system), 3.85 (d, J=13.2 Hz, 1H, AB system), 2.87 (s, 3H, NMe), 2.43 (d, J=13.5 Hz, 1H, AB system), 2.19 (s, 6H, cumyl), 2.12 (s, 3H, NMe), 1.93 (d, J=13.2 Hz, 1H, AB system), 1.78 (s, 6H, cumyl), 1.74 (s, 6H, cumyl), 1.67 (s, 6H, cumyl), 1.20 (s, 9H, O-t-Bu), 0.75 (s, 9H, O-t-Bu) ppm.

$^{13}$C NMR (100.63 MHz, C$_6$D$_6$): δ=161.1 (CO), 158.4 (CO), 153.1 (C), 152.1 (C), 151.7 (C), 151.6 (C), 138.3 (C), 137.2 (C), 135.6 (C), 135.3 (C), 134.8 (C), 129.7 (C), 129.2 (C), 128.9 (CH), 126.9 (CH), 126.8 (CH), 126.3 (CH), 126.2 (CH), 125.8 (CH), 125.6 (CH), 125.5 (CH), 125.3 (CH), 124.9 (CH), 124.0 (CH), 122.3 (C), 119.1 (CH), 76.4 (OC), 74.2 (OC), 67.9 (CH$_2$), 64.8 (CH$_2$), 62.8 (CH$_2$), 44.1 (CH$_3$), 43.8 (CH$_3$), 42.5 (C), 42.2 (C), 34.2 (C), 33.6 (C), 32.8 (Ot-Bu), 32.6 (Ot-Bu), 31.2 (CH$_3$), 30.8 (CH$_3$), 30.1 (CH$_3$), 29.7 (CH$_3$) ppm.

Anal. Calc. for C$_{67}$H$_{82}$N$_2$O$_4$Zr: C, 75.15; H, 7.72; N, 2.62. Found: C, 75.07; H, 8.12; N, 2.82.

Preparation of Lig$^{32}$Hf(OtBu)$_2$ (see, Formula II wherein $R_1=R_2=R_3=R_4$=cumyl; $R_5=R_6=R_7=R_8$=H; Z and Y form together benzyl; R'=R=methyl; and Q=Hf(OtBu)$_2$):

To a stirring colorless solution of Hf(O-tert-Bu)$_4$ (22 mg, 0.047 mmol) in 2 mL of ether was added dropwise Lig$^{32}$H$_2$ (39 mg, 0.047 mmol) in ether (2 mL) at room temperature.

After 2 hours the solvent was removed under vacuum, and the resulting white solid was washed with 2 mL of pentane and dried under vacuum. The final yield was 49 mg (90%, 0.042 mmol).

$^1$H NMR (400 MHz, C$_6$D$_6$): δ=7.63 (d, J=2.4 Hz, 1H), 7.58 (m, 2H), 7.45-7.38 (m, 5H), 7.31-7.20(m, 6H), 7.14-7.08 (m, 6H), 6.98-6.79 (m, 10H), 6.70 (dd, J=8.8 Hz, 1.6 Hz, 1H), 6.67 (d, J=2.8 Hz, 1H), 6.64 (d, J=2.4 Hz, 1H), 4.47 (d, J=12.2 Hz, 1H, AB system), 3.92 (d, J=14.4 Hz, 1H, AB system), 3.87 (d, J=12.2 Hz, 1H, AB system), 2.86 (s, 3H, NMe), 2.43 (d, J=13.5 Hz, 1H, AB system), 2.21 (s, 6H, cumyl), 2.12 (s, 3H, NMe), 1.92 (d, J=13.2 Hz, 1H, AB system), 1.78 (s, 6H, cumyl), 1.75 (s, 6H, cumyl), 1.65 (s, 6H, cumyl), 1.20 (s, 9H, O-t-Bu), 0.77 (s, 9H, O-t-Bu) ppm.

$^{13}$C NMR (100.63 MHz, C$_6$D$_6$): δ=161.1 (CO), 158.4 (CO), 153.2 (C), 152.1 (C), 151.7 (C), 151.4 (C), 138.2 (C), 137.3 (C), 136.0 (C), 134.6 (CH), 129.6 (C), 129.3 (CH), 128.9 (CH), 127.1 (CH), 127.0 (CH), 126.8 (CH), 126.3 (CH), 126.1 (CH), 125.8 (CH), 125.5 (CH), 125.4 (CH), 125.1 (CH), 124.0 (C), 122.4 (C), 119.2 (CH), 76.0 (OC), 73.9 (OC), 68.0 (CH$_2$), 64.9 (CH$_2$), 62.9 (CH$_2$), 44.5 (NCH$_3$), 43.9 (NCH$_3$), 42.9 (C), 42.5 (C), 42.2 (C), 34.2 (C), 33.0 (Ot-Bu), 32.6 (Ot-Bu), 31.5 (CH$_3$), 30.9 (CH$_3$), 30.7 (CH$_3$), 30.1 (CH$_3$), 29.8 (CH$_3$) ppm.

Preparation of Lig$^{33}$HfBn$_2$ (see, Formula II wherein R$_1$=R$_2$=R$_3$=R$_4$=t-bu; R$_5$=R$_6$=R$_7$=R$_8$=H; Z and Y form together benzyl; R'=R=H; and Q=HfBn$_2$):

Lig$^{33}$H$_2$ (97 mg, 0.18 mmol) was dissolved in about 1 mL of cold toluene and the solution was added dropwise to a stirring solution of HfBn$_4$ (95 mg, 0.18 mmol) in about 1 mL of cold toluene. The reaction mixture was stirred for 2 hours and the solvent was thereafter removed under vacuum, yielding a white solid, which was washed with about 1 mL of pentane and dried in vacuo. The final yield was 132 mg (82%).

Preparation of Lig$^{34}$Zr(O-tert-butyl)$_2$ (see, Formula II wherein R$_1$=R$_2$=R$_3$=R$_4$=a; R$_5$=R$_6$=R$_7$=R$_8$=H; Z and Y form together benzyl; R'=R=Hl; and Q=Zr(OtBu)$_2$):

Lig$^{34}$H$_2$ (49 mg, 0.10 mmol) was dissolved in about 1 mL of diethyl ether and the solution was added dropwise to a stirring solution of Zr(O-tert-butyl)$_4$ (240 mg, 0.10 mmol) in about 1 mL of diethyl ether. The reaction mixture was stirred for 2 hours and the solvent was thereafter removed under vacuum, yielding a white solid, which was washed with about 1 mL of pentane and dried in vacuo. The final yield was 68 mg (93%).

$^1$H NMR (C$_6$D$_6$, 400 MHz): δ=7.36 (d, 1H, J=2.5 Hz, ArH), 7.02-6.86 (d, 3H, ArH), 6.52-6.38 (d, 3H, ArH), 4.29 (d, J=13.4 Hz, 1H), 4.15 (m, 1H, CH), 3.92 (m, 1H, CH), 3.26 (m, 1H, CH), 2.53 (d, J=13.4 Hz, 1H), 2.37 (d, J=12.3 Hz, 1H), 1.12 (m, 18H, OC(CH$_3$)$_3$) ppm.

Preparation of Lig$^{34}$HfBn$_2$ (see, Formula II wherein R$_1$=R$_2$=R$_3$=R$_4$=Cl; R$_5$=R$_6$=R$_7$=R$_8$=H; Z and Y form together benzyl; R'=R=H; and Q=HfBn$_2$):

Lig$^{34}$H$_2$ (77 mg, 0.16 mmol) was dissolved in about 1 mL of cold toluene and the solution was added dropwise to a stirring solution of HfBn$_4$ (88 mg, 0.16 mmol) in about 1 mL of cold toluene. The reaction mixture was stirred for 2 hours and the solvent was thereafter removed under vacuum, yielding a white solid, which was washed with about 1 mL of pentane and dried under vacuum. The final yield was 128 mg (95%).

As can be seen hereinabove analysis of the structural features of the prepared metal complexes was performed by various techniques including $^1$H NMR, $^{13}$C NMR, and crystallography in cases where single crystals were obtained. The complexes were found to be mononuclear, containing a single Salan ligand per metal atom for all the tested complexes. The complexes were also characterized as containing labile groups (see, X in Scheme 8 above). These labile groups can be activated to form a reactive polymerization catalyst.

Spectroscopic characterization showed that the Salan metal complex is obtained as a single diastereomer of C$_1$-symmetry (see, FIG. 5). Crystallographic studies revealed that the two labile groups are cis-related, a coordination mode suitable for polymerization. This mode of wrapping was supported by spectroscopic characterization and crystallographic studies of several complexes, as detailed herein.

Example 3

Catalytic Polymerization

General Procedures:

The Salan-based complexes described herein (e.g., in Example 2) were employed as catalysts in polymerization of olefins following suitable activation.

Various types of olefins are polymerized by these systems, including, for example, non-substituted olefins such as ethylene, low olefins such as propylene and 1-butene, higher olefins such as 1-hexene, dienes such as 1,5-hexadiene, bulky olefins such as vinyl-cyclohexane, and olefins bearing aromatic substituents such as styrene. The catalytic activity toward such a broad scope of monomers attests to the applicability of the Salan-based catalytic systems both for polymerization and co-polymerization of a variety of monomers.

A variety of polymerization procedures was tested and found to be suitable for the Salan-based systems. Salan complexes including labile alkyl groups (such as benzyl) are typically activated by alkyl elimination with either boron-type co-catalysts or with co-catalysts of the aluminum family such as MAO, or different combinations of co-catalysts of these families. Salan complexes that include non-alkyl labile groups such as chloro groups are typically alkylated in the activation process, making MAO and related co-catalysts as well as combination of various catalysts suitable for their activation.

In a typical polymerization procedure of a monomer which is liquid at atmospheric pressure, e.g., 1-hexene or styrene, a metal complex as described herein is added to one portion of the monomer and a co-catalyst is added to a second portion of the same monomer. Mixing the two monomer portions leads to initiation of the polymerization process, which is continued for a time period that typically depends on the rate of the polymerization process and can range from less than 1 minute to several hours. Once the reaction is complete, the excess of the remaining monomer is removed under reduced pressure, traces of the non-polymeric materials (resulting from the catalyst and co-catalyst) are removed, and the polymer is isolated and analyzed.

Such polymerization procedures may be performed in the presence of a pre-dried organic solvent such as toluene or heptane.

In such polymerizations of liquid monomers (e.g., 1-hexene), using B(C$_6$F$_5$)$_3$ as co-catalyst (typically at an equimolar ratio or in slight excess above equimolar), polymerization runs of 2-4 hours are typically employed, while using MAO as co-catalyst results in polymerization runs of between 1 minute (500 molequivalents of MAO) to 10 minutes (50 equivalents of MAO).

For monomers which are gaseous at room temperature and may be easily condensed (e.g., propylene), several polymerization procedures are employed.

In a typical solvent-less polymerization of a gaseous monomer such as propylene, a stainless steel reactor equipped with an inner glass sleeve and a magnetic stir-bar is charged with the appropriate number of molequivalents of MAO and with the metal complex, and is cooled down with a liquid nitrogen bath. A measured volume of propylene is condensed; the reactor is sealed and allowed to warm to room temperature. The polymerization is typically pursued for 13-14 hours. The summed weight of monomer and formed polymer are measured, and the remaining monomer is released. The polymer is treated with acidified solution (e.g., 5% HCl/methanol solution) and petroleum ether, and left to stir for 12 hours. The soluble polymer part is thereafter extracted from the petroleum ether solution by evaporating the solvent under reduced pressure. The insoluble polymer part is obtained by filtration and air dried.

In a typical solution polymerization procedure of a gaseous monomer such as propylene or ethylene, a dry solvent such as toluene, containing a predetermined number of molequivalents of a co-catalyst such as MAO, is charged with the monomer up to a given pressure at a pre-determined temperature (e.g., between 0 and 70° C.). The pre-catalyst is injected and the pressure and temperature of the polymerization reaction are monitored. A mass-flow controller is optionally employed to sustain a specific pressure, and the gas consumption is thus monitored as well. A typical pressure is 33.5 psig. The polymerization is stopped by addition of methanol and release of the unreacted monomer. The obtained polymer is treated with an acidified solution (5% HCl/methanol solution) and left to stir for 12 hours. The soluble polymer part is extracted from the solution by evaporating the solvent under reduced pressure. The insoluble polymer part is obtained by filtration and air dried.

An alternative polymerization procedure involves the formation of the pre-catalyst in situ, by mixing of the ligand precursor and the metal reagent in the polymerization mixture. Such a procedure takes advantage of the fast reaction of the Salan ligand precursor with metal reagents such as MBn$_4$ (M=Ti, Zr, Hf), and of the clean formation of a single diastereomer of the complex, which is suitable for polymerization catalysis. This option alleviates the necessity to isolate a well-defined metal complex, and may be particularly useful in the case of thermally less stable Salan complexes such as benzyl titanium complexes.

In a typical such procedure, a toluene solution of the metal reagent (e.g., TiBn$_4$) is added to a toluene solution of a Salan ligand precursor, followed by saturation of solution with the monomer (e.g., propylene, at 33.5 psig). A co-catalyst (e.g., MAO, about 500 molequivalents) is then injected and the polymerization is allowed to proceed as described hereinabove. The obtained polymer is isolated as described hereinabove.

The polymer samples were characterized by one or more of the following techniques:

$^{13}$C-NMR was employed to determine stereoregularity (%[mmmm]), regioregularity, and the possible presence of chain ends or low molecular weight oligomers. The spectra were measured at room temperature in CDCl$_3$ for soluble polymers such as poly(1-hexene) and at high temperature (110-155° C.) in C$_6$D$_4$Cl$_2$ for polymer samples that were insoluble at room temperature (mostly isotactic polypropylene), as described hereinabove. % [mmmm] for polypropylene was determined based on the methyl peak, by integrating the mmmm pentad relative to all observable methyl pentads.

For very highly isotactic polypropylene ([mmmm] equal or higher than 95%), the peaks corresponding to stereoerrors (only the mmmr, mmrr, and mrrm peaks are observed for highly isotactic polypropylene obtained with these catalysts) were compared to the $^{13}$C-satellites adjacent to the mmmm peak.

Gel Permeation Chromatography (GPC) was employed to determine molecular weights (M$_w$ and M$_n$) and molecular weight distributions (PDI), at room temperature for soluble polymers such as poly(1-hexene) and at high temperature for crystalline polymer samples (e.g., isotactic polypropylene), as described hereinabove.

Differential Scanning calorimetry (DSC) was employed for characterizing the obtained polypropylene, by determining Melting Transition (T$_m$), and Heat of Melting (or heat of fusion) ($\Delta$H, J/g).

Polymerization of Propylene

The Salan-based systems described herein were found to be suitable for polymerization of propylene under a broad range of conditions. Salan metal pre-catalysts of the form Lig$^x$M(X)n where Lig$^x$ is one of the Salan ligands, M is a group 4 metal, and X is an alkyl (benzyl), were employed with MAO as a typical co-catalyst. The polymerization was run either in solvent-less liquid propylene or in propylene dissolved in an organic solvent such as toluene, according to the general procedures described hereinabove. The ratio of co-catalyst varied, with a typical ratio being 500:1, and with a ratio of 50:1 still being sufficient for production of substantial quantities of polypropylene. For polymerizations in solution, different temperatures were employed. An active catalytic polymerization of propylene was performed also without the use of an isolated pre-catalyst, but rather with pre-catalyst formed in situ (in the polymerization mixture) by mixing of a Salan ligand precursor and a metal reagent such as TiBn$_4$.

I. Polymerization of Propylene by Salan-Titanium Catalyst Systems:

The titanium Salan catalyst systems presented herein showed a tendency to produce isotactic polymers, which was found to be affected by the nature of the skeleton and of the substituents of the two phenol rings of the Salan ligand. For most of the systems studied, highly isotactic polypropylene of high molecular weight was produced (as was immediately apparent from the solid form of the obtained polymers). For several catalytic systems, polypropylene having melting transitions (T$_m$) reaching 168.8° C. were obtained. These values are among the highest melting transitions ever reported for "as prepared" (not extracted or annealed) isotactic polypropylene prepared by catalytic polymerization, and measured by employing a standard DSC protocol (2$^{nd}$ heating run, 10° C. min$^{-1}$), as described hereinabove.

Figure 8:
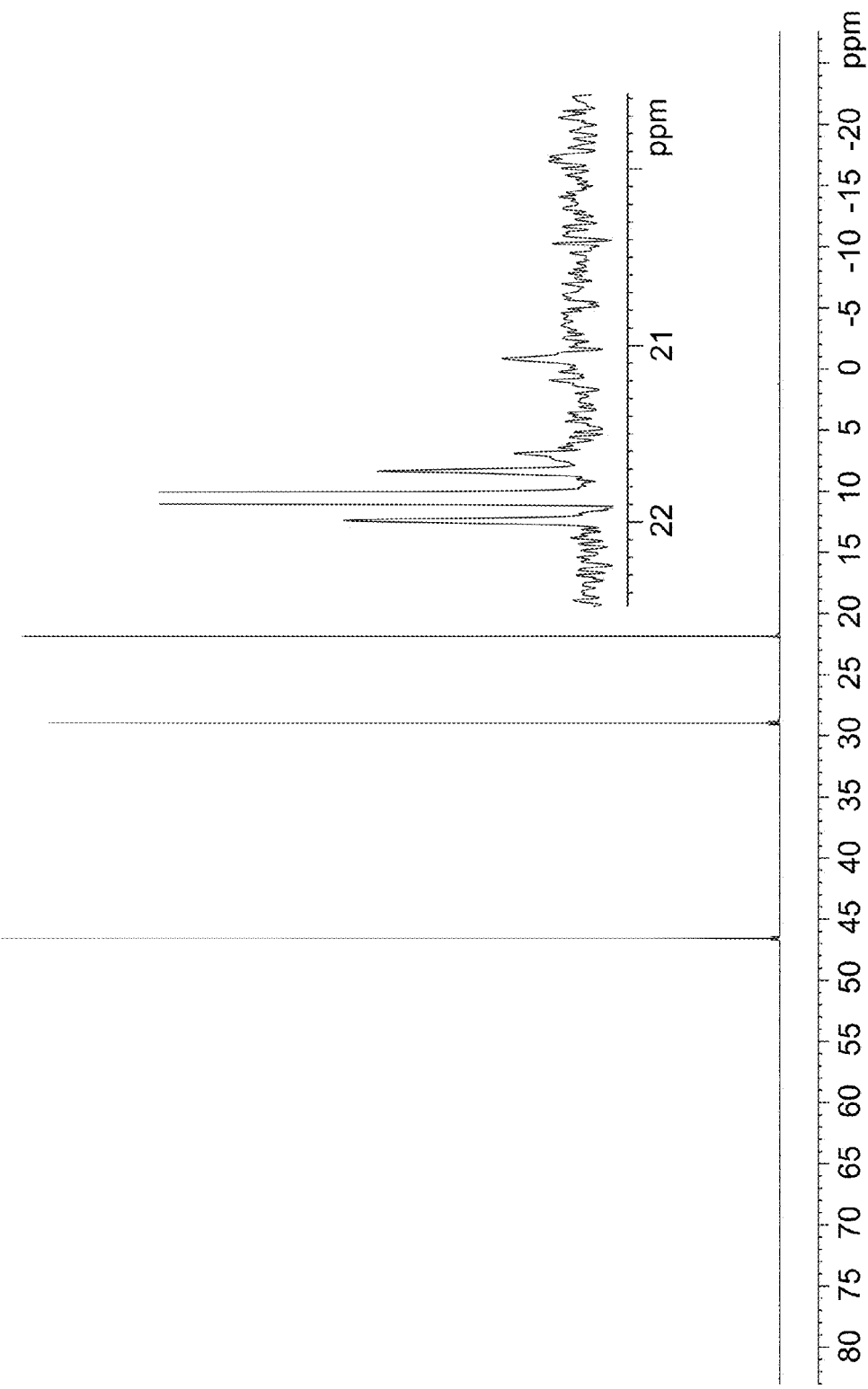
FIG. 8 presents a $^{13}$C-NMR spectrum of highly isotactic poly-propylene produced in the presence of the catalyst system Lig$^{20}$TiBn$_2$/MAO, as described herein, with the inset showing an enlargement of the methyl region (around 22 ppm).

The degree of isotacticity was evaluated by the melting transition of the polypropylene, and by $^{13}$C NMR analysis of the peak of the methyl group, at the pentad level, wherein the mmmm pentad represents an isotactic sequence, and an r relationship signifies a deviation from ideal isotacticity (See, for example, FIG. 8).

For all polymers exhibiting a high degree of isotacticity, a ratio of 2:2:1 of the [mmmr], [mmrr], and [mrrm] pentad peaks was found, which corresponds to an enantiomorphic site control of isoselectivity.

Thus, as can be seen, for example, in FIG. 8, peaks in the vicinity of the mmmm pentad are $^{13}$C satellites, which are much higher than the mmmr and mmrr stereoerror pentads. Mrrm pentad is hardly observed.

No regioerror or chain-end peaks could be detected in the obtained spectra, which signify polymers with very high degree of regio-regularity and high molecular weight.

It was generally found that for polymers samples with high enough molecular weights, a higher percent of the [mmmm] was also reflected in a higher melting transition. For the polymers with the highest melting transitions, [mmmm]≥99.5% was measured. These values are among the highest ever reported for isotactic polypropylene prepared by any catalyst, and correspond to one stereo-error every one thousand repeat units.

Molecular weight analysis of the obtained polypropylene samples showed high molecular weights (which in most cases exceeded $M_w=100,000$ and in certain cases was higher than $M_w=1,000,000$), and narrow molecular weight distributions.

Due to high MW and high isotacticity, many of the samples exhibited low solubility and could not be analyzed by GPC at high temperatures.

I.a. Liquid, Solvent-Less Polymerization (of Neat Propylene): Polymerization of Neat Propylene Using Ti-Catalysts Having a Salan Ligand with Methylaminoethylamine Skeleton:

A stainless steel reactor equipped with an inner glass sleeve and a magnetic stir-bar was charged with a dibenzyltitanium complex of the series $Lig^{1-12}TiBn_2$ and 500 equivalents of MAO and was cooled with a liquid nitrogen bath. A measured quantity of propylene (see, Table 1) was condensed, the reactor was sealed, and was allowed to warm to room temperature. The quantity of propylene was determined by substracting the weight of the reactor prior to propylene addition from the weight of the reactor including the total weight of condensed propylene. The polymerization was pursued for 13-14 hours. The total weight of the monomer and formed polymer was measured, and the remaining monomer was released. The polymer was treated with acidified methanol solution (5% HCl solution) and petroleum ether. The insoluble polymers were obtained by filtration and were dried in air. Data are presented in Table 1.

bath. A measured volume of propylene was condensed, the reactor was sealed, and was allowed to warm to room temperature. The polymerization was pursued for 13-14 hours. The total weight of the monomer and formed polymer was measured, and the remaining monomer was released. The polymer was treated with acidified methanol solution (5% HCl solution) and petroleum ether. The insoluble polymers were obtained by filtration and were dried in air. Data are presented in Table 2.

TABLE 2

| Pre-catalyst | Monomer (g) | Polymer (g) | $T_m$ (° C.) | ΔH (J/g) | Mw (g/mol) | Mw/Mn | [mmmm] (%) |
|---|---|---|---|---|---|---|---|
| $Lig^{18}TiBn_2$ | 5.84 | 2.03 | 160.9 | 91.9 | 97,000 | 5.6 | 98.90 |
| $Lig^{19}TiBn_2$ | 9.78 | 2.89 | 163.7 | 93.2 | 60,000 | 5.3 | |
| $Lig^{20}TiBn_2$ | 7.03 | 2.57 | 166.9 | 92.8 | 45,500 | 3.1 | |
| $Lig^{22}TiBn_2$ | 8.69 | 0.49 | 162.4 | 80.1 | | | |
| $Lig^{25}TiBn_2$ | 9.02 | 2.03 | 150.5 | 106.9 | 320,000 | 1.60 | 92 |

I.b. Solution Polymerization:

Selected catalysts were employed in polymerization of propylene in solution, according to the general procedure described hereinabove. Toluene (50 mL) was used as a solvent, and the polymerization conditions included the concentration of the pre-catalyst, and the ratio of co-catalyst to pre-catalyst. All reactions were performed at room temperature. The solution polymerizations enabled the evaluation of catalyst activity. In certain cases, extremely high activities were recorded, and the rates of polymerizations may be diffusion-controlled, as instantaneous formation of polymer was found upon addition of pre-catalyst to a toluene solution containing the pre-catalyst and propylene. The activity values in those cases include the formal time elapsing until the quencher was added (methanol), and should represent a lower limit of activity. The degree of tacticity obtained by those catalysts in solution, as evident in the melting transitions of the resulting polypropylene, was in some cases higher than that obtained in liquid, solventless polymerization of propylene.

Data are presented in Table 3, for Ti-catalysts having a Salan ligand with methylaminoethylamine skeleton and in

TABLE 1

| Pre-catalyst | Monomer (g) | Polymer (g) | $T_m$ (° C.) | ΔH (J/g) | Mw (g/mol) | Mw/Mn | [mmmm] (%) |
|---|---|---|---|---|---|---|---|
| $Lig^1TiBn_2$ | 8.85 | 0.54 | 154.8 | 36.2 | | | 87 |
| $Lig^2TiBn_2$ | 7.42 | 0.29 | 136.7 | 5.2 | | | 61.6 |
| $Lig^3TiBn_2$ | 9.71 | 0.51 | 139.9 | 34.1 | | | 83.8 |
| $Lig^4TiBn_2$ | 6.68 | 3.15 | 139.1 | 85.9 | 1,034,000 | 1.83 | |
| $Lig^7TiBn_2$ | 7.12 | 1.32 | 160.1 | 99.8 | | | 98.4 |
| $Lig^8TiBn_2$ | 9.12 | 1.53 | 162.6 | 96.5 | 147,000 | 2.5 | |
| $Lig^9TiBn_2$ | 8.47 | 2.70 | 163.8 | 93.4 | 52,000 | 3.0 | 99.36 |
| $Lig^{11}TiBn_2$ | 8.69 | 0.49 | 162.4 | 80.1 | 124,000 | 2.0 | |

Polymerization Of Neat Propylene Using Ti-Catalysts Having a Salan Ligand with Chiral Aminomethylpyrrolidine Bridge:

A stainless steel reactor equipped with an inner glass sleeve and a magnetic stir-bar was charged with a dibenzyltitanium complex of the series $Lig^{18-25}TiBn_2$ and 500 equivalents of MAO and was cooled with a liquid nitrogen Table 4, for Ti-catalysts having a Salan ligand with chiral aminomethylpyrrolidine skeleton.

It can be seen that the results are highly reproducible. It can further be seen that the activities recorded are high and attained at very short times, indicating a lack of an induction period.

TABLE 3

| Pre-catalyst | Amount of pre-catalyst | Equiv MAO | Time sec. | Activity (g mmol$^{-1}$ h$^{-1}$) | Polymer (g) | $T_m$ (° C.) | $\Delta H$ (J/g) | Mw (g/mol) | Mw/Mn | [mmmm] (%) |
|---|---|---|---|---|---|---|---|---|---|---|
| Lig$^2$TiBn$_2$ | 7 mg [10 μmol] | 500 | 1620 | 87.3 | 0.39 | 139.5 | 77.6 | 773,000 | 1.65 | |
| Lig$^7$TiBn$_2$ | 7 mg [10 μmol] | 500 | 20 | 17,100 | 0.95 | 161.9 | 123.1 | 296,000 | 1.21 | 96.50 |
| Lig$^8$TiBn$_2$ | 8 mg [10 μmol] | 500 | 30 | 5,160 | 0.43 | 164.3 | 64.3 | 356,500 | 2.8 | 98.90 |
| Lig$^9$TiBn$_2$ | 9 mg [10 μmol] | 500 | 30 | 11,760 | 0.98 | 166.2 | 174.0 | 39,000 | 2.1 | 99.35 |
| Lig$^{11}$TiBn$_2$ | 8 mg [10 μmol] | 500 | 3600 | 53 | 0.53 | 166.5 | 89.2 | 59,000 | 2.3 | 99.55 |
| Lig$^{12}$TiBn$_2$ | 9 mg [10 μmol] | 500 | 14400 | 6 | 0.23 | 154.7 | 24.7 | 276,000 | 4.0 | 95.16 |

TABLE 4

| Pre-catalyst | Amount of pre-cat | Equiv MAO | Time (min) | Activity (g mmol$^{-1}$ h$^{-1}$) | Polymer (g) | $T_m$ (° C.) | $\Delta H$ (J/g) | Mw (g/mol) | Mw/Mn | [mmmm] (%) |
|---|---|---|---|---|---|---|---|---|---|---|
| Lig$^{18}$TiBn$_2$ | 8 mg [10 μmol] | 500 | 1 | 2,040 | 0.34 | 159.5 | 126.2 | 35,000 | 3.6 | 99.12 |
| Lig$^{19}$TiBn$_2$ | 8 mg [10 μmol] | 500 | 1 | 10,740 | 1.79 | 165.5 | 120.3 | 40,000 | 2.75 | 99.49 |
| Lig$^{20}$TiBn$_2$ | 9 mg [10 μmol] | 500 | 1 | 8,840 | 1.49 | 168.8 | 72.8 | 48,000 | 2.2 | 99.60 |
| Lig$^{23}$TiBn$_2$ | 8 mg [10 μmol] | 500 | 10 | 156 | 0.26 | 166.1 | 43.8 | 80,000 | 2.3 | 99.05 |

Polymerization of Propylene in Toluene Solution (Formation of the Pre-Catalyst In Situ):

A toluene solution of TiBn$_4$ (4 mg, 10 μmmol) was added to a toluene solution of the ligand precursor Lig$^{20}$H$_2$ (7 mg, 10 μmmol), followed by saturation of the solution with propylene (33.5 psig), and then injection of about 500 equivalents (0.29 gram) of MAO. The polymerization was performed at room temperature and was stopped after 2 hours by injection of methanol and release of the remaining propylene. The polymer was treated with acidified methanol solution (5% HCl solution), filtered and dried on the air.

The total weight of resulting polymer is 1.34 gram. (Activity: 67 grams mmol$^{-1}$h$^{-1}$).

II. Polymerization of Propylene by Salan-Zirconium and Salan-Hafnium Systems:

The zirconium and hafnium Salan-based catalytic systems were found to be suitable catalysts for propylene polymerization upon activation with the appropriate co-catalysts.

II.a. LIQUID, SOLVENTLESS POLYMERIZATION

Polymerization of Neat Propylene Using Zr-Catalysts:

The polymerization processes were conducted as described hereinabove for solventless polymerization with Ti-catalysts, employing the dibenzylzirconium complexes Lig$^{1,7}$ZrBn$_2$ and 500 equivalents of MAO. Data are presented in Table 5.

TABLE 5

| Pre-catalyst | Monomer (g) | Polymer (g) | $T_m$ (° C.) | $\Delta H$ (J/g) | [mmmm] |
|---|---|---|---|---|---|
| Lig$^1$ZrBn$_2$ | 9.14 | 4.64 | 126 | 8.5 | 59 |
| Lig$^7$ZrBn$_2$ | 9.03 | 2.99 | 139.9 | 2.8 | 68 |

Polymerization Of Neat Propylene Using Hf-Catalysts:

The polymerization processes were conducted as described hereinabove for Ti-catalysts, while employing the dibenzylhafnium complexes Lig$^1$HfBn$_2$ (see, Table 6) and Lig$^{30-34}$HfBn$_2$ (see, Table 7), and 500 equivalents of MAO.

TABLE 6

| Pre-catalyst | Monomer (g) | Polymer (g) | $T_m$ (° C.) | $\Delta H$ (J/g) | [mmmm] (%) |
|---|---|---|---|---|---|
| Lig$^1$HfBn$_2$ | 8.54 | 0.72 | 146.6 | 37.9 | 71 |

TABLE 7

| Pre-catalyst | Monomer (g) | Polymer (g) | $T_m$ ($\Delta H$) (° C., J/g) |
|---|---|---|---|
| Lig$^{30}$HfBn$_2$ | 9.33 | 0.31 | 132 (23) |
| Lig$^{31}$HfBn$_2$ | 8.94 | 0.17 | 156 (69.9) |
| Lig$^{32}$HfBn$_2$ | 6.83 | 0.10 | 154.1 (51.7) |
| Lig$^{34}$HfBn$_2$ | 8.47 | 0.18 | 158.2 (70.7) |
| Lig$^{33}$HfBn$_2$ | 7.72 | 0.05 | 154.4 (36.8) |

II.b. Solution Polymerization:

Polymerization of Propylene in Toluene Solution Using Zr-Catalysts:

Solution polymerization processes were performed according to the general procedure described hereinabove, by injecting a toluene solution of the zirconium pre-catalyst to a solution of propylene (33.5 psig) dissolved in 380 mL of toluene and containing 500 equivalents of MAO, and performing the reaction at room temperature. The polymerizations were stopped by injection of methanol and release of the remaining propylene. Data are presented in Table 8.

TABLE 8

| Pre-catalyst | Amount of pre-catalyst | MAO Equiv | Time | Activity (g mmol$^{-1}$ h$^{-1}$) | Polymer (g) | $T_m$ (° C.) | ΔH (J/g) | [mmmm] % |
|---|---|---|---|---|---|---|---|---|
| Lig$^7$ZrBn$_2$ | 8 mg [10 μmol] | 500 | 2 h | 29 | 0.58 | 96.5 | 20.8 | 68 |

Polymerization of Ethylene

Polymerization of ethylene was exemplified in toluene solution. Polymerization processes were performed by injecting a toluene solution of a titanium pre-catalyst to a solution of ethylene (33.5 psig) dissolved in 70 mL of toluene and containing 0.29 gram (500-19000 equivalents) of MAO at different temperatures. The polymerizations were stopped by injection of methanol and release of the remaining ethylene. Data are presented in Table 9.

TABLE 9

| Pre-Catalyst | Amount of pre-catalyst (mg [mmol]) | Equiv MAO (0.29 g) | Temp (° C.) | Time (hours) | Activity (g mmol$^{-1}$ h$^{-1}$) | Polymer (g) | $T_m$ (ΔH) (° C., J/g) |
|---|---|---|---|---|---|---|---|
| Lig$^9$TiBn$_2$ | 3 mg [3 μmol] | 1500 | 0 | 2 | 335 | 2.23 | 129.89 (120.53) |
| Lig$^9$TiBn$_2$ | 0.22 mg [0.24 μmol] | 19000 | 0 | 4 | 475 | 0.456 | 132.87 (104.73) |
| Lig$^{20}$TiBn$_2$ | 3 mg [3 μmol] | 1500 | 0 | 1 | 264 | 0.88 | 133.9 (90.1) |
| Lig$^{20}$TiBn$_2$ | 0.22 mg [0.24 μmol] | 19000 | 0 | 1 | 763 | 0.183 | 133.53 (107.58) |
| Lig$^{20}$TiBn$_2$ | 0.22 mg [0.24 μmol] | 19000 | 70 | 1 | 5,400 | 1.29 | 133.37 (135.07) |
| Lig$^3$TiBn$_2$ | 9 mg [10 μmol] | 500 | 0 | 4 | 170 | 6.79 | 133.03 (103.80) |

Copolymerization of Ethylene- 1-hexene

A glass reactor equipped with a magnetic stir-bar was charged with 500 equivalents of MAO, 3 mL of 1-hexene and 50 mL of toluene. Ethylene was passed through the reaction mixture at atmospheric pressure for 20 minutes. The polymerization process started by injection of 10 μmol of catalyst Lig$^{20}$TiBn$_2$. The polymerization was stopped after 1 hours, by injection of methanol and release of the remaining ethylene. The polymer was treated with acidified methanol solution (5% HCl solution), filtered and dried in air. The total weight of the resulting polymer was 2.82 grams (Activity: 282 g mmol$^{-1}$ h$^{-1}$).

Figure 9:
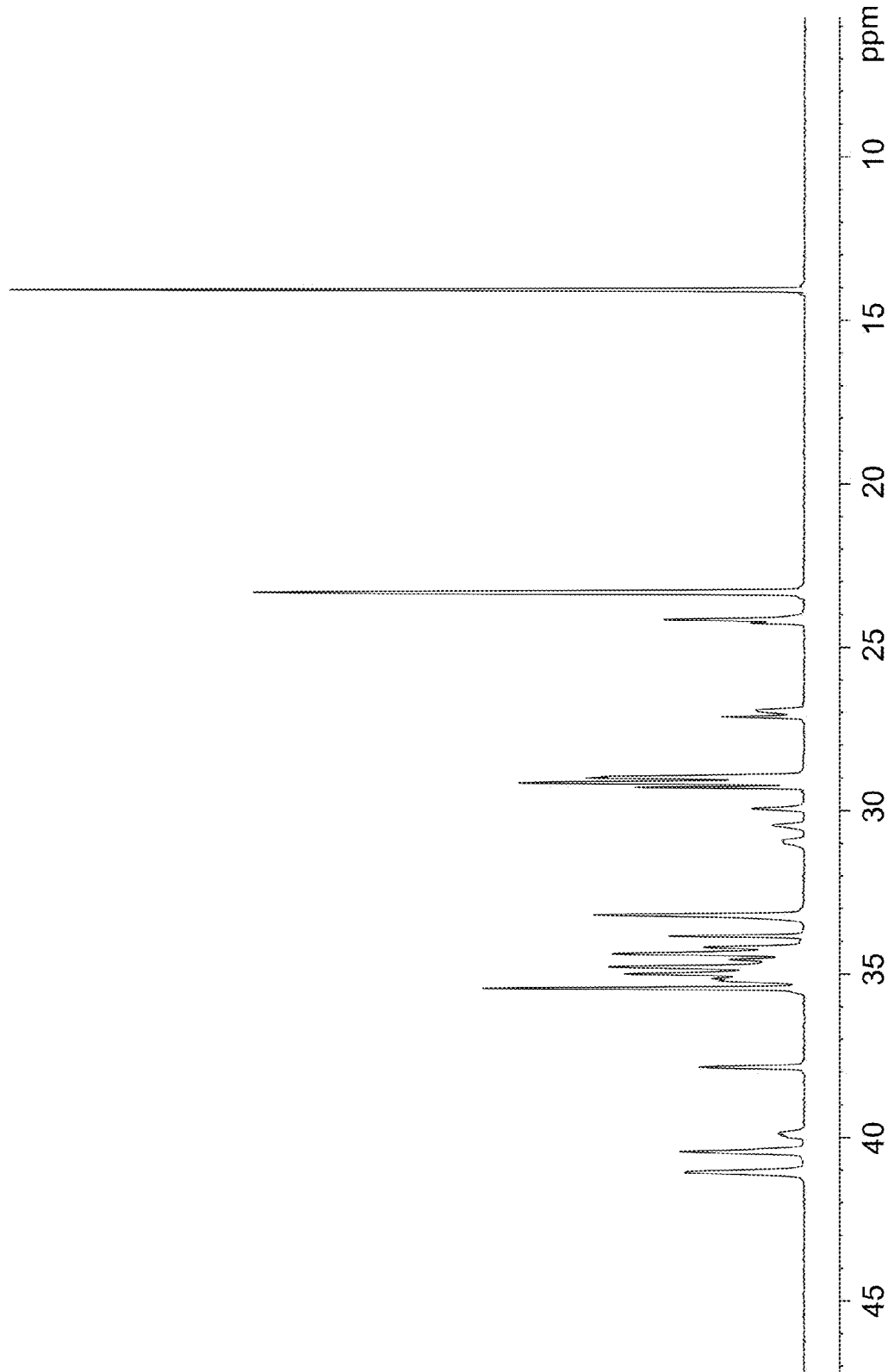
FIG. 9 presents a $^{13}$C-NMR spectrum of a copoly-(ethylene-1-hexene) produced in the presence of an exemplary catalyst system, Lig$^{20}$TiBn$_2$/MAO, as described herein.

FIG. 9 presents the $^{13}$C NMR spectrum of the obtained polymer, and indicate the formation of random ethylene/1-hexene copolymers.

Polymerization of 1-butene

Neat, solventless polymerization of 1-butene was performed with Ti-catalyst. A stainless steel reactor equipped with an inner glass sleeve and a magnetic stir-bar was charged with a Lig$^9$TiBn$_2$ catalyst and 500 equivalents of MAO and was cooled by means of a liquid nitrogen bath. A measured quantity (as indicated in Table 10 and as determined for propylene supra) of 1-butene was condensed, the reactor was sealed, and was allowed to warm to room temperature. The polymerization was pursued for 13-14 hours. The total weight of the monomer and formed polymer were measured, and the remaining monomer was released. The polymer was treated with acidified methanol solution (5% HCl solution) and petroleum ether. The insoluble polymers were obtained by filtration and were dried in air. Data are presented in Table 10.

TABLE 10

| PreCatalyst (amount) | Toluene (mL) | Temp (° C.) | Monomer (g) | Time (h) | Polymer (g) | Activity (g mmol$^{-1}$ h$^{-1}$) | Trans:cis | [mmmm] (%) |
|---|---|---|---|---|---|---|---|---|
| Lig$^{20}$ZrBn$_2$ (9 mg) | 20 | 60 | 1.0 | 6 | 0.99 | 17 | 1:0.43 | >99 |

Figure 10:
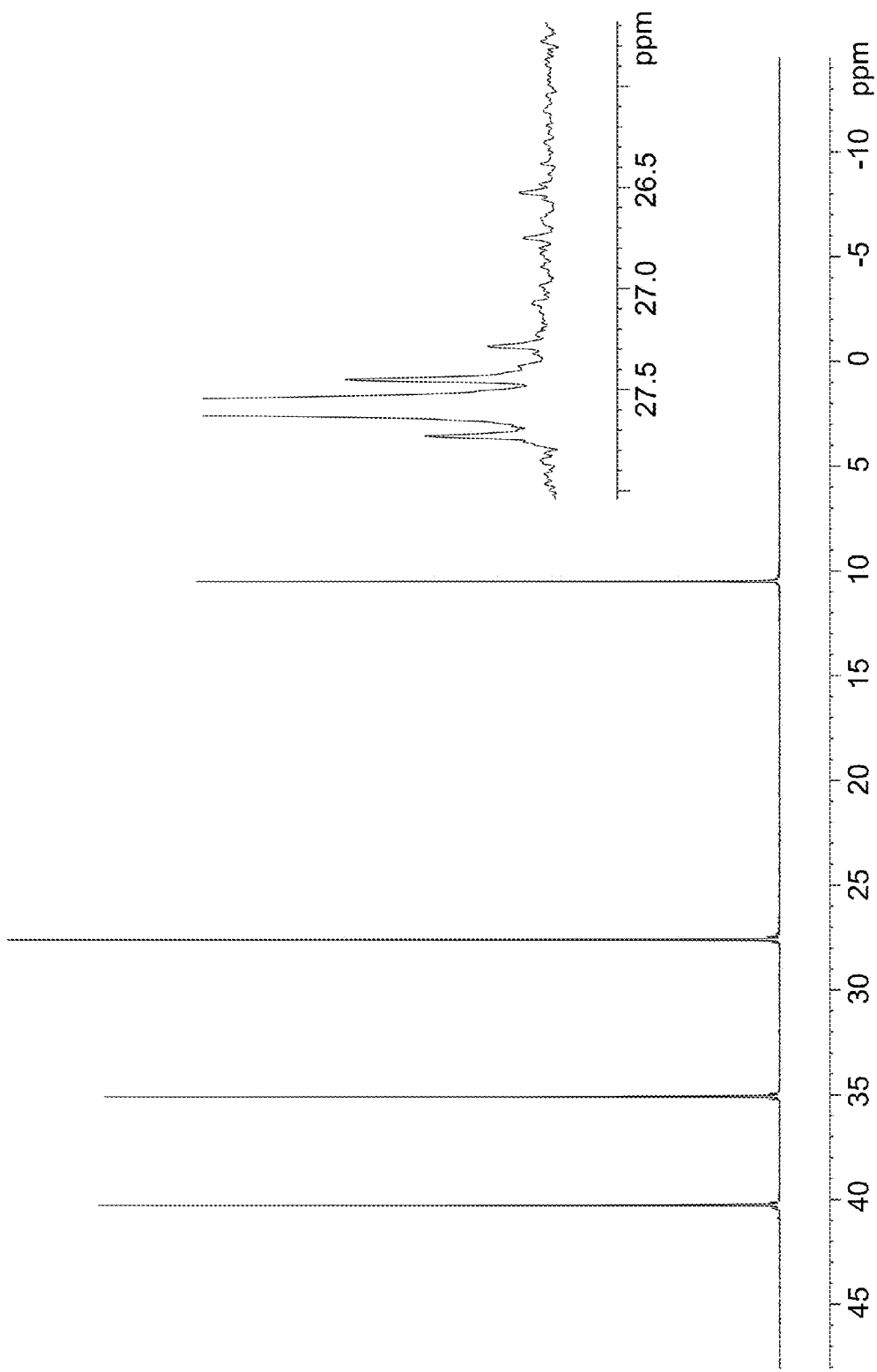
FIG. 10 presents a $^{13}$C-NMR spectrum of highly isotactic poly-1-butene produced in the presence of an exemplary catalyst system Lig$^9$TiBn$_2$/MAO, as described herein with the inset showing an enlargement of the methyl region (around 27 ppm)

FIG. 10 presents the $^{13}$C NMR spectrum of the obtained poly-1-butene, with the insertion showing the methyl region. Peaks in the vicinity of the mmmm pentad are $^{13}$C satellites, which are much higher than the mmrr and mrrm stereoerror pentads.

Polymerization of 1-hexene

Poly-(1-hexene) was obtained by liquid, solventless polymerization of 1-hexene with dibenzyl titanium complexes activated with MAO. A dibenzyltitanium complex Lig$^9$TiBn$_2$ (10 μmol) was dissolved in 1 mL of 1-hexene and the solution was added to a stirred solution of MAO (500 equivalents) in 4 mL 1-hexene. The resulting mixture was stirred at room temperature until the resulting polymer solution had become viscous. The polymer was treated with acidified methanol solution (5% HCl solution) and extracted with chloroform.

Polymerization of 1-hexene was similarly performed with Lig$^{31,32}$Hf(OtBu)$_2$. Data for all processes are presented in Table 11.

TABLE 11

| PreCatalyst | Amount precatalyst | condition | Time (h) | Polymer (g) | Activity (g mmol$^{-1}$ h$^{-1}$) | [mmmm] (%) |
|---|---|---|---|---|---|---|
| Lig$^9$TiBn$_2$ | 8 mg [10 µmol] | neat | o.n. | 1.76 | n/a | 98.7 |
| Lig$^9$TiBn$_2$ | 8 mg [10 µmol] | 50 mL toluene, RT | 3 | 0.586 | 19.5 | 99.4 |

Figure 11:
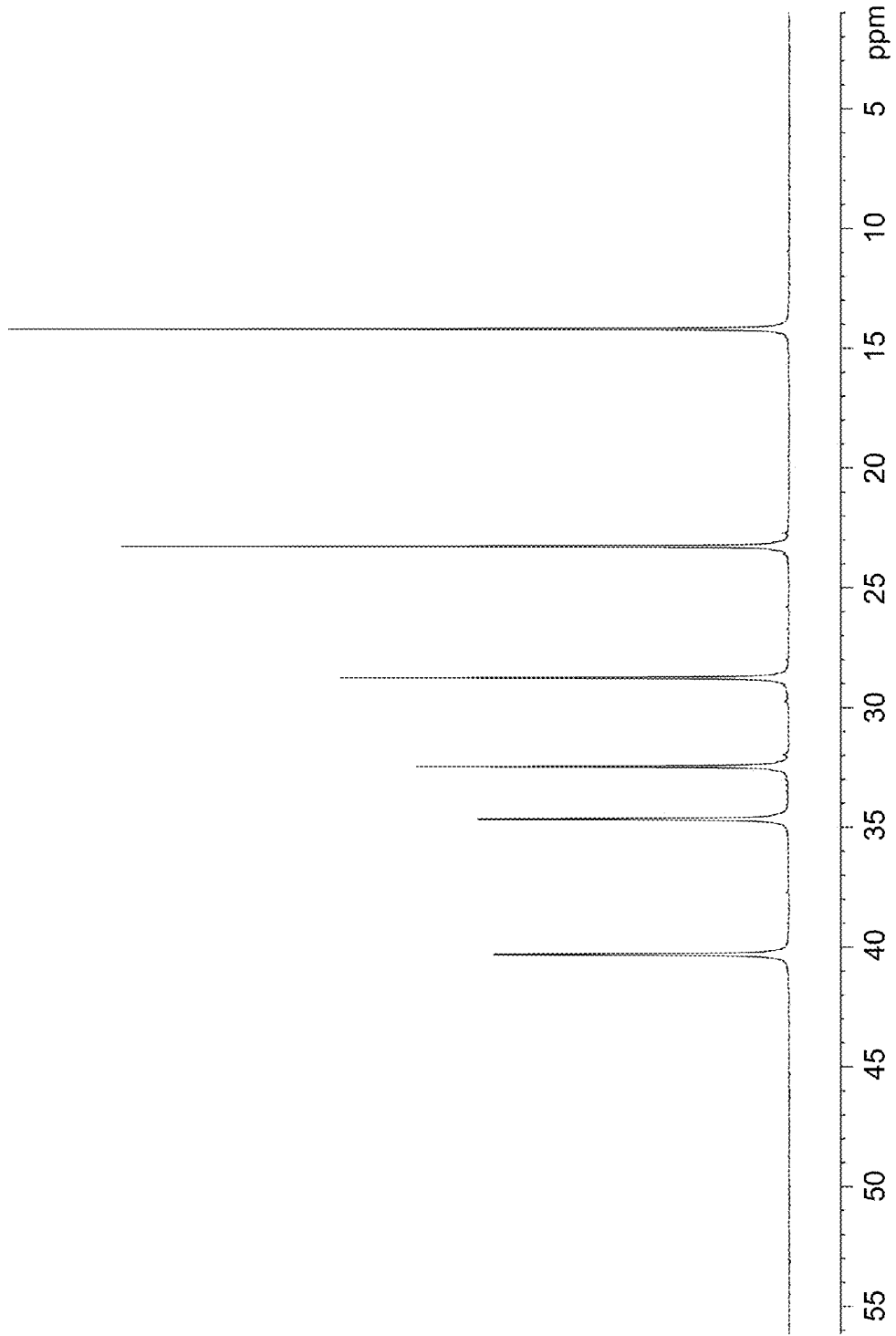
FIG. 11 presents a $^{13}$C-NMR spectrum of highly isotactic poly-1-hexene produced in the presence of an exemplary catalyst system, Lig$^9$TiBn$_2$/MAO, as described herein.

FIG. 11 presents the $^{13}$C NMR spectrum of the obtained poly-hexene, produced in the presence of a Lig$^9$TiBn$_2$/MAO catalyst system, and indicating the formation of a highly isotactic polymer.

Polymerization of 1,5-Hexadiene

Polymerization of 1,5-hexadiene was exemplified in toluene solution. A dibenzylzirconium complex Lig$^{20}$ZrBn$_2$ (10 µmol) was dissolved in 0.5 mL of toluene and the solution was added to a stirred and heated (to 60° C.) solution of MAO (500 equiv), including 1 gram of 1,5-hexadiene in 20 mL toluene. The resulting mixture was stirred for 6 hours. The polymer obtained (PMCP—poly(1,3-methylenecyclopentane) was treated with acidified methanol solution (5% HCl solution), filtered and dried in air. An optically active polymer was obtained, having [α]$^d$ of +47.2. Other data are presented in Table 12.

TABLE 12

| PreCatalyst | Amount precatalyst | Time | Polymer (g) | Activity (g mmol$^{-1}$ h$^{-1}$) | Mw/Mn | [mmmm] (%) |
|---|---|---|---|---|---|---|
| Lig$^9$TiBn$_2$ | 7 mg [10 µmol] | 3 min. | 1.94 | 3,900 | | >99 |
| Lig$^{31}$Hf(OtBu)$_2$ | 9 mg [10 µmol] | 15 h | 0.29 | 3 | 11,100 | 73 |
| Lig$^{32}$Hf(OtBu)$_2$ | 10 mg [10 µmol] | 15 h | 0.45 | 3 | 10,500 | 82 |

Figure 12:
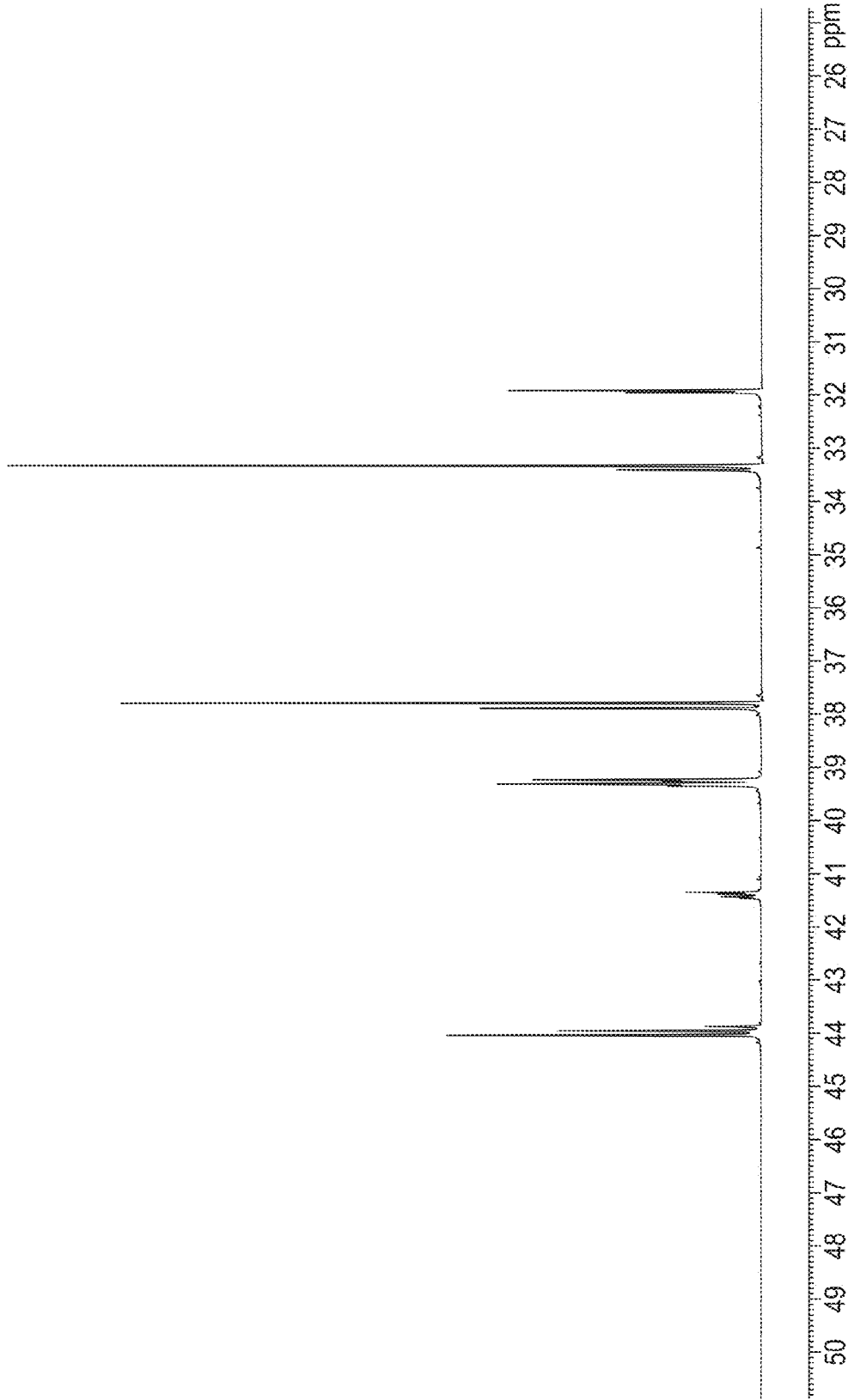
FIG. 12 presents a $^{13}$C-NMR spectrum of optically active poly-methyl-cyclopentane produced in the presence an exemplary catalyst system, Lig$^{20}$ZrBn$_2$/MAO, as described herein.

FIG. 12 presents the $^{13}$C NMR spectrum of the obtained poly-methyl-cyclopentane, produced in the presence of a Lig$^{20}$ZrBn$_2$/MAO catalyst system, and indicating the formation of an optically active isotactic polymer.

Polymerization of vinylcyclohexane

Polymerization of vinylcyclohexane was performed in toluene solution as follows. A dibenzyltitanium complex Lig$^{20}$TiBn$_2$ (10 µmol) was dissolved in 0.5 mL of toluene and the solution was added to a stirred solution of MAO (500 equiv) and 1 gram vinylcyclohexane in 20 mL toluene. The resulting mixture was stirred for 1 hour. The poly-VCH was treated with acidified methanol solution (5% HCl solution), filtered and dried in air. Data are presented in Table 13.

TABLE 13

| Pre-Catalyst | Amount of precat (mg [mmol]) | Time | Activity (g mmol$^{-1}$ h$^{-1}$) | Polymer (g) | % mmmm |
|---|---|---|---|---|---|
| Lig$^{20}$TiBn$_2$ | 10 mg [10 µmol] | 1 hour | 58.3 | 0.583 | >99 |

Figure 13:
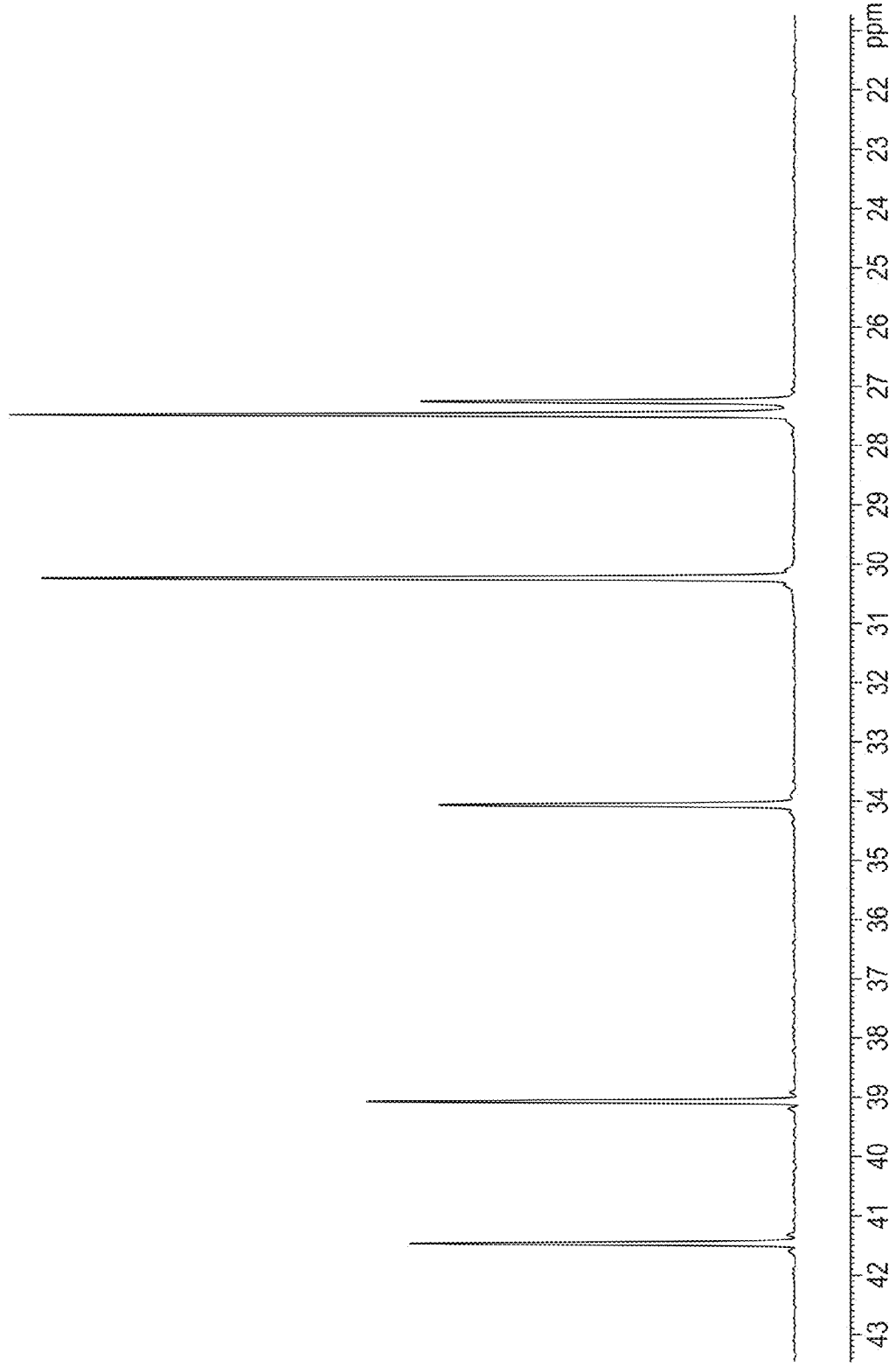
FIG. 13 presents a $^{13}$C-NMR spectrum of highly isotactic poly-vinyl-cyclohexane produced in the presence of an exemplary catalyst system, Lig$^{20}$TiBn$_2$/MAO, as described herein.

FIG. 13 presents the $^{13}$C NMR spectrum of the obtained poly-vinyl-cyclohexane, produced in the presence of a Lig$^{20}$TiBn$_2$/MAO catalyst system, indicating the formation of a highly isotactic polymer.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents, patent applications, priority documents and testing procedures mentioned in this specification are herein incorporated in their entirety by reference into the specification, to the extent they are not inconsistent with this specification. In addition, citation or identification of any reference in this application shall not be construed as an admission that such reference is available as prior art to the present invention. To the extent that section headings are used, they should not be construed as necessarily limiting.

What is claimed is:

1. A process of polymerizing an alpha-olefin, the process comprising contacting the alpha-olefin with a catalyst system which comprises:

(i) a pre-catalyst comprising a group 4 element being in coordination with a Salan ligand, said Salan ligand comprising two substituted or unsubstituted phenol moieties and a sequential diamino-containing skeleton unit linking said phenol moieties, wherein said sequential diamino-containing skeleton unit is non-symmetric and said pre-catalyst is devoid of a symmetry element; and (ii) a co-catalyst, thereby polymerizing the alpha-olefin.

2. The process of claim 1, wherein said pre-catalyst is represented by general Formula II:

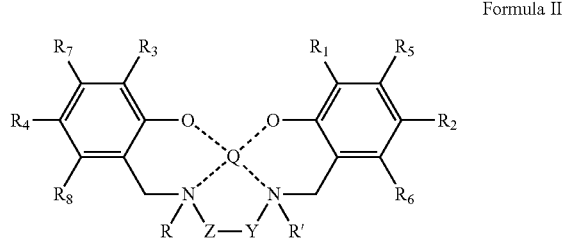

Formula II wherein:

Q is MXn, whereas M is a group 4 element; X is a labile group; and n is 0, 1, 2, 3 or 4;

Z and Y are each independently a substituted or unsubstituted alkylene chain being from 1 to 5 carbon atoms in length, such that Z and Y form together an alkylene chain that is 2 to 10 carbon atoms in length;

each of $R_1$-$R_8$ is independently selected from the group consisting of hydrogen, alkyl, cycloalkyl, aryl, halogen, alkoxy, aryloxy, heteroalicyclic, heteroaryl, and nitro, provided that at least one of $R_1$-$R_4$ is other than hydrogen; and each of R and R' is independently selected from the group consisting of hydrogen, alkyl, cycloalkyl and aryl, provided that at least one of R and R' is hydrogen; and provided that when R and R' are the same, Y is different from Z; and (ii) a co-catalyst, thereby polymerizing the alpha-olefin.

3. The process of claim 2, wherein each of $R_1$-$R_4$ is independently halogen.

4. The process of claim 2, wherein at least one of $R_1$-$R_4$ is a bulky substituent.

5. The process of claim 4, wherein said bulky substituent comprises a bulky rigid group.

6. The process of claim 4, wherein $R_1$ is adamantyl.

7. The process of claim 2, wherein Z is selected from the group consisting of (CRaRb), (CRaRb)(CRcRd) and (CRaRb)(CRcRd)(CReRf), and Y is selected from the group consisting of (CRgRh), (CRgRh)(CRiRj) and (CRgRh)(CRiRj)(CRkRp), wherein each of Ra-Rp is independently selected from the group consisting of hydrogen, alkyl, cycloalkyl, aryl, halogen, alkoxy, aryloxy, and/or at least two of Ra-Rp, R' and R form together a five-or six-membered, aromatic or non-aromatic ring.

8. The process of claim 2, wherein R' is hydrogen.

9. The process of claim 8, wherein R is alkyl.

10. The process of claim 1, wherein said alpha-olefin is propylene.

11. A process of polymerizing an alpha-olefin, the process comprising contacting the alpha-olefin with a catalyst system which comprises:

(i) a pre-catalyst comprising a group 4 element being in coordination with a Salan ligand, said Salan ligand comprising two substituted or unsubstituted phenol moieties and a sequential diamino-containing skeleton unit linking said phenol moieties, wherein said sequential diamino-containing skeleton unit is non-symmetric and said pre-catalyst is devoid of a symmetry element; and (ii) a co-catalyst, thereby polymerizing the alpha-olefin, wherein said pre-catalyst is represented by general Formula II:

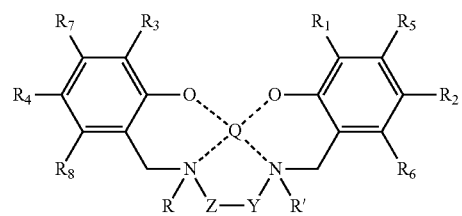

Formula II wherein:

Q is MXn, whereas M is a group 4 element; X is a labile group; and n is 0, 1, 2, 3 or 4;

Z and Y are each independently a substituted or unsubstituted alkylene chain being from 1 to 5 carbon atoms in length, such that Z and Y form together an alkylene chain that is 2 to 10 carbon atoms in length;

each of $R_1$-$R_4$ is independently halogen;

each of $R_5$-$R_8$ is independently selected from the group consisting of hydrogen, alkyl, cycloalkyl, aryl, halogen, alkoxy, aryloxy, heteroalicyclic, heteroaryl, and nitro; and each of R and R' is independently selected from the group consisting of hydrogen, alkyl, cycloalkyl and aryl, provided that at least one of R and R' is hydrogen; and provided that when R and R' are the same, Y is different from Z.

12. A process of polymerizing an alpha-olefin, the process comprising contacting the alpha-olefin with a catalyst system which comprises:

(i) a pre-catalyst comprising a group 4 element being in coordination with a Salan ligand, said Salan ligand comprising two substituted or unsubstituted phenol moieties and a sequential diamino-containing skeleton unit linking said phenol moieties, wherein said sequential diamino-containing skeleton unit is non-symmetric and said pre-catalyst is devoid of a symmetry element; and (ii) a co-catalyst, thereby polymerizing the alpha-olefin, wherein said pre-catalyst is represented by general Formula II:

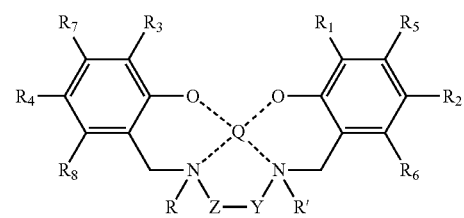

Formula II wherein:

Q is MXn, whereas M is a group 4 element; X is a labile group; and n is 0, 1, 2, 3 or 4;

Z and Y are each independently a substituted or unsubstituted alkylene chain being from 1 to 5 carbon atoms in length, such that Z and Y form together an alkylene chain that is 2 to 10 carbon atoms in length;

each of $R_1$-$R_8$ is independently selected from the group consisting of hydrogen, alkyl, cycloalkyl, aryl, halogen, alkoxy, aryloxy, heteroalicyclic, heteroaryl, and nitro, provided that at least one of $R_1$-$R_4$ is a bulky substituent which comprises a bulky rigid group; and each of R and R' is independently selected from the group consisting of hydrogen, alkyl, cycloalkyl and aryl, provided that at least one of R and R' is hydrogen; and provided that when R and R' are the same, Y is different from Z.

13. A process of polymerizing an alpha-olefin, the process comprising contacting the alpha-olefin with a catalyst system which comprises:

(i) a pre-catalyst comprising a group 4 element being in coordination with a Salan ligand, said Salan ligand comprising two substituted or unsubstituted phenol moieties and a sequential diamino-containing skeleton unit linking said phenol moieties, wherein said sequential diamino-containing skeleton unit is non-symmetric and said pre-catalyst is devoid of a symmetry element; and (ii) a co-catalyst, thereby polymerizing the alpha-olefin, wherein said pre-catalyst is represented by general Formula II:

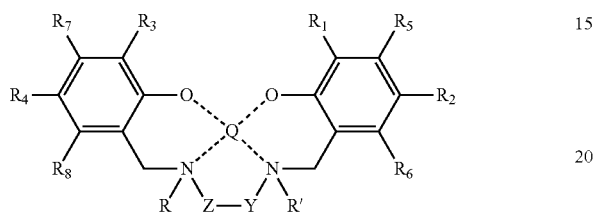

Formula II wherein:

Q is MXn, whereas M is a group 4 element; X is a labile group; and n is 0, 1, 2, 3 or 4;

Z and Y are each independently a substituted or unsubstituted alkylene chain being from 1 to 5 carbon atoms in length, such that Z and Y form together an alkylene chain that is 2 to 10 carbon atoms in length;

$R_1$ is adamantyl;

each of $R_2$-$R_8$ is independently selected from the group consisting of hydrogen, alkyl, cycloalkyl, aryl, halogen, alkoxy, aryloxy, heteroalicyclic, heteroaryl, and nitro; and each of R and R' is independently selected from the group consisting of hydrogen, alkyl, cycloalkyl and aryl, provided that at least one of R and R' is hydrogen; and provided that when R and R' are the same, Y is different from Z.

* * * * *